US008859273B2

(12) United States Patent
Sigg et al.

(10) Patent No.: US 8,859,273 B2
(45) Date of Patent: *Oct. 14, 2014

(54) METHODS OF USING HCN GENES TO TREAT CARDIAC ARRHYTHMIAS

(75) Inventors: Daniel Sigg, St. Paul, MN (US); James A. Coles, Jr., Columbia, MD (US); Erica TenBroek, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 474 days.

This patent is subject to a terminal disclaimer.

(21) Appl. No.: 11/022,172

(22) Filed: Dec. 22, 2004

(65) Prior Publication Data

US 2007/0218034 A1 Sep. 20, 2007

Related U.S. Application Data

(60) Provisional application No. 60/532,764, filed on Dec. 24, 2003.

(51) Int. Cl.
*C12N 15/00* (2006.01)
*A61K 48/00* (2006.01)
*C07H 21/04* (2006.01)
*A61K 38/17* (2006.01)

(52) U.S. Cl.
CPC ......... *A61K 38/177* (2013.01); *C12N 2840/203* (2013.01); *A61K 48/005* (2013.01); *C12N 2750/14143* (2013.01)
USPC ..................... 435/320.1; 424/93.21; 536/23.1

(58) Field of Classification Search
CPC .................. A60K 48/005; C12N 2750/14143; C12N 15/86; C12N 2840/203; C12N 2799/022; C12N 2502/1329; C12N 2502/1358; C12N 2510/00; C12N 5/065; C07K 14/4705
USPC ...................... 435/320.1; 424/93.2; 514/44 R
See application file for complete search history.

(56) References Cited

U.S. PATENT DOCUMENTS

| | | | | |
|---|---|---|---|---|
| 5,580,777 | A * | 12/1996 | Bernard et al. | ............... 435/456 |
| 6,162,796 | A | 12/2000 | Kaplitt et al. | |
| 6,214,620 | B1 | 4/2001 | Johns et al. | |
| 6,376,471 | B1 | 4/2002 | Lawrence et al. | |
| 6,451,594 | B1 | 9/2002 | Chien et al. | |
| 6,506,379 | B1 | 1/2003 | Clackson et al. | |
| 6,551,821 | B1 | 4/2003 | Kandel et al. | |
| 6,979,532 | B2 * | 12/2005 | Jansen et al. | ...................... 435/4 |
| 2002/0022259 | A1 | 2/2002 | Lee et al. | |
| 2002/0025577 | A1 | 2/2002 | Goldspink | |
| 2002/0155101 | A1 | 10/2002 | Donahue | |
| 2002/0187948 | A1 | 12/2002 | Rosen et al. | |
| 2003/0082153 | A1 | 5/2003 | Epstein | |
| 2003/0118988 | A1 | 6/2003 | Kandel et al. | |
| 2003/0166593 | A1 | 9/2003 | Chien et al. | |
| 2003/0204206 | A1 | 10/2003 | Padua et al. | |
| 2004/0068299 | A1 | 4/2004 | Laske et al. | |
| 2004/0068312 | A1 | 4/2004 | Sigg et al. | |

FOREIGN PATENT DOCUMENTS

| | | | |
|---|---|---|---|
| GB | WO02/02630 | * | 1/2002 |
| WO | WO 99/36538 | | 7/1999 |
| WO | WO 02/19966 A | | 3/2002 |
| WO | WO 02/50300 | | 6/2002 |
| WO | WO/02/087419 | * | 11/2002 |
| WO | WO 02/087419 | | 11/2002 |
| WO | WO 02/087419 A | | 11/2002 |
| WO | WO 02/098286 | | 12/2002 |

OTHER PUBLICATIONS

Zhang et al Circulation, 2002; 106(10): 1294-9.*
Mocini et al, Ital Heart J. 2005; 6(3): 267-71.*
Ecke et al Goodman & Gilman's The Pharmacological basis of Therapeutics, McGraw-Hill, New York, NY. pp. 77-101.*
Verma and Somia (1997) Nature 389: 239-242.*
Verma et al Annu Rev Biochem. (2005), 74:711-38.*
Opalinska et al. Nature Reviews Drug Discovery 2002.*
Ngo et al., 1994, The protein Folding Problem and Tertiary Structure Prediction, pp. 491-495.*
Gepstein Expert Opinion Biol Ther, 5(12); 1531-1537, 2005.*
Menasché et al Thromb Haemost. Oct. 2005;94(4):697-701.*
Ishii et al Journal of Physiology, 2001, 537, 93-100.*
Brondyk W Promega Notes Magazine No. 51, 1995, p. 10.*
Rosen, M.R., Recreating the Biological Pacemaker, The Anatomical Record Part A, 2004, vol. 180A, pp. 1046-1052.
Rosen, M.R., Biolotical Pacemaking: In Our Lifetime?, Heart Rhythm, 2005, vol. 2, No. 4, pp. 418-428.
Benson, D.A. et al. Nucl. Acids. Res. 25:1-6 (1997).
Biel, M. et al, Trends Cardiovasc. Med. 12:206-213 (2002).
Discher, D.J. et al., J. Biol. Chem. 273:26087-26093 (1998).
Edelberg, J., Heart 86:559-562 (2001).
Fozzard, H.A. et al. eds, The Heart and Cardiovascular System. Scientific Foundations Raven Press, NY (1986).
Guzman, R.J. et al., Circ. Res. 73:1202-1207 (1993).
Han, X. et al., Proc. Natl. Acad. Sci. 92:9747-9751 (1995).
Hardy, S. et al., J. of Virology 71:1842-1849 (1997).
Jiang, A. et al., J. Virol. 72:10148-10156 (1998).
Klugherz, B.D., et al., Hum. Gene Ther. 13(3):443-54 (2002).
Kurata, Y. et al., Am. J. Physiol. Heart Circ. Physiol. 283:H2074-H2101 (2002).
Lapointe, M.C. et al., Am. J. Physiol. Heart Circ. Physiol. 283:H1439-45 (2002).
Lesso, H. and Li, R.A., J.of Biol. Chem. 278 (25): 22290-22297 (2003).
Much, B. et al., J. Biol. Chem. 278: 43781-43786 (2003).
Prentice, H. et al., Cardiovascular Res. 35:567-574 (1997).
Sakhuja, K. et al., Human Gene Therapy 14:243-254 (2003).

(Continued)

*Primary Examiner* — Anoop Singh
(74) *Attorney, Agent, or Firm* — Mueting, Raasch & Gebhardt, P.A.

(57) ABSTRACT

The subject invention is directed to methods of treating cardiac pacing dysfunction by administering HCN genes, alone or in combination with other genes.

2 Claims, 24 Drawing Sheets

(56) References Cited

OTHER PUBLICATIONS

Sambrook, J. et al., Molecular Cloning: A Laboratory Manual, Section 1, Cold Spring Harbor Laboratory Press (1989).
Sartiani, L. et al., Journal of Physiology 545(1):81-92 (2002).
Silva, J. and Rudy, Y., Circ. Res. 92:261-263 (2003).
Stieber, J., et al., J. Biol. Chem. 278 (36):33672-33680 (2003).
Ulens, C. and Tytgat, J., J. Biol. Chem. 276(9):6069-6072 (2001).
Weitz, D. et al., Neuron 36: 881-889 (2002).
Xu, S.Z. and Beech, D.J., Circ. Res. 88:84-87 (2001).
Zhang, H. et al., Am. J. Physiol. Heart Circ. Physiol. 279:H397-H421 (2000).
Zheng, J. et al., Neuron 36:891-896 (2002).
Zhong, H. et al., Nature 420:193-196 (2002).

* cited by examiner

METHODS OF USING HCN GENES TO TREAT CARDIAC ARRHYTHMIAS

CROSS-REFERENCES TO RELATED APPLICATIONS

The present application claims priority under Title 35, United States Code, §119 to provisional application U.S. Patent application Ser. No. 60/532,764 filed Dec. 24, 2003.

FIELD OF INVENTION

The present invention relates to compositions and methods for treating cardiac (brady-)arrhythmias, and more particularly to systems and methods involving the application of gene and cell therapy to treat cardiac pacing dysfunction.

REFERENCE TO SEQUENCE LISTING

Included with the present specification is one compact disc. The compact disc contains one file named Sequence Listing.txt which is 100,420 bytes in size and was created on Dec. 22, 2004. The material contained on the compact disc included with the present specification is hereby incorporated-by-reference.

BACKGROUND OF THE INVENTION

In a normal human heart, cardiac contraction is initiated by the spontaneous excitation of the sinoatrial ("SA") node that is located in the right atrium. The electrical current generated by the SA node travels to the atrioventricular ("AV") node where it is then transmitted to the bundle of His and Purkinje network, which branches in many directions to facilitate coordinated contraction of the left and right ventricles.

The cellular basis for the aforementioned electrical impulse is the action potential (AP). The AP is conventionally divided into five phases (phases 0-4) in which each phase is defined by the cellular membrane potential and the activity of potassium, sodium, chloride, and calcium ion channel proteins that affect that potential. These channels, embedded in cell membranes, allow for electrical impulses to occur as they permit charged ions to rush through them. Propagation of electrical activity from an individual cardiac cell to surrounding cardiac tissue takes place through gap junctions, small pore-like structures that connect cardiac muscle cells to each other. The role of ion channels in cardiac electrical conduction is analogous to electrical conduction in other tissues such as skeletal muscle.

Some channels or gates have their own "non-provoked" rhythmic excitation also known as automaticity. The generation of cardiac automaticity is based on a complex interplay between at least four different channels of cationic (positive ion) nature: T- and L-type calcium channels, a cation channel named $I_f$, and potassium channels. The $I_f$ channel has been termed the pacemaker channel. $I_f$ channels have unique properties such as: 1) $I_f$ channels open upon membrane hyperpolarization; 2) $I_f$ channels allow for mixed cation current (Na+ and K+); 3) cyclic AMP (cAMP-cyclic adenosine monophosphate which serves as an intracellular messenger molecule) binds to the cytoplasmic site of the channel thereby accelerating its activation kinetics and shifting the voltage dependence of the cell to more positive voltages; and lastly 4) $I_f$ channels are susceptible to blockade by extracellular Cs+ (cesium ion). The genes responsible for the $I_f$ channel currents have recently been identified and belong to the HCN (hyperpolarization-activated cyclic nucleotide-gated) family. Four different isoforms have been identified in vertebrates (HCN1, HCN2, HCN3 and HCN4) and all except HCN3 have been found in the heart. HCN3 is specifically expressed in neurons.

HCN channels directly interact with intracellular cAMP so that an increase in cAMP levels results in increased If and more positive activation potentials. This increase thereby accelerates the heart rate (HR) in response to sympathetic stimulation. In contrast, muscarinic stimulation slows the heart rate in part due to a decrease in cAMP levels and a resulting reduction of $I_f$ and more negative activation potentials. Ludwig, A. et al.; "Two pacemaker channels from human heart with profoundly different activation kinetics." EMBO J. (1999) 18 (9):2323-2329. The importance of the HCN genes in regulating heart rate has recently been shown in a patient who suffered from mutation in his HCN4 gene. This mutation consisted of a complete deletion of the C-terminus of the gene which included the cAMP binding domain. This patient suffered from symptomatic bradycardia and an electronic pacemaker needed to implanted. These mutations were recreated in vitro experiments, and the mutated channel was expressed in a cell line. The mutated HCN4 channel was completely inresponsive to cAMP. See, J Clin Invest. 2003 May:111(10):1537-45.

HCN1 is primarily expressed in the brain and shows little dependence on cAMP. HCN1 is also expressed in the rabbit SA node and displays properties of brain h-channels in that it has a short AP. HCN2 and HCN4 are predominantly expressed in the heart, as well as in the brain, and produce currents similar to $I_f$. HCN1 is the fastest activating channel (25-300 ms), followed by HCN2 and HCN3 (180-500 ms), and lastly HCN4 (a few hundred ms to seconds). All four subunits induce pacemaker current similar to $I_f$ if the units are expressed in heterologous expression systems. In addition, the four isoforms can interact with one another to form tetramers (couplings whereby the two isomers join to create a functionally different structure). The heteromerization of the isoforms changes pacemaker electrophysiology via altered activation kinetics (e.g., allows for modulation (increase or decrease) of heart rate). (Much B et al. J of Biol Chem; 44 (31): 43781-43786). While the exact stoichiometry of the heteromerized HCN channels has not been described yet, it is considered that these channels may form heteromers with a 3:1 ratio, but ratios of 1:1 or 1:3 are also possible as the HCN channels are known to form tetramers. In related rod photoreceptor cyclic nucleotide-gated channels, an asymmetrical stoichiometry of the two subunits present in the tetramers of 3:1 was determined. Zhong H et al. Nature 2002; 420: 193-196. Weitz D et al. Neuron 2002; 36: 881-889. Zheng J et al. Neuron 2002; 36: 891-896.

To avoid misunderstandings due to different naming of the same proteins, isoform nomenclature for the mouse brain is as follows: HCN1 corresponds to HAC2 (mBCNG-1), HCN2 corresponds to HAC1 (mBCNG-2) and HCN3 corresponds to HAC3 (mBCNG4).

In certain diseased states, the heart's ability to pace properly is compromised. For example, failure of SA nodal automaticity, resulting in an insufficient number of electrical impulses emanating from the SA node, is the most common cause of bradyarrhythmias (heart rhythm that is too slow). If slowing is enough so that the resultant heart rate is insufficient to meet the body's demand, symptoms result. Symptomatic bradycardia originating from the sinus node is part of a clinical syndrome characterized by brady- and tachyarrhythmias originating from a diseased sinus node, commonly referred to as sick sinus syndrome. Clinically, sick sinus syndrome is a very common problem and accounts for approximately 70% of all pacemaker implants in the general population. Other bradyarrhythmic disease states due to slowed or absent impulse propagation include the various degrees of AV block (e.g. $1^{st}$, $2^{nd}$, or $3^{rd}$). Tachyarrhythmias (heart rhythm that is too fast) and fibrillation are also a concern. These conditions present major problems ranging from cost of treatment to diminished quality of life and even death.

Currently, bradyarrhythmias are most commonly treated by the implantation of (exogenously driven) electronic pacemaker. While improving the lives of many patients, implantable pacemakers have a limited lifetime and consequently may expose a patient to multiple surgeries to replace the implantable pacemaker. Biological methods of influencing the pacing rate of cardiac cells, however, have recently been developed, including the use of various drugs and pharmacological compositions. Developments in genetic engineering have resulted in methods for genetically modifying cardiac cells to influence their intrinsic pacing rate. For example, U.S. Pat. No. 6,214,620 describes a method for suppressing excitability of ventricular cells by over-expressing (e.g. $K^+$ channels) or under-expressing certain ion channels (e.g. $Na^+$ and $Ca^{2+}$ channels). PCT Publication No. WO 02/087419 describes methods and systems for modulating electrical behavior of cardiac cells by genetic modification of inwardly rectifying $K^+$ channels (specifically, $I_{K1}$) in quiescent ventricular cells.

Of particular import to those who suffer from bradyarrhythmias due to insufficient production of $I_f$, PCT Publication No. WO 02/098286 describes methods for regulating pacemaker function of cardiac cell via modulation of HCN channels (HCN 1, 2, or 4 isoforms). See also U.S. Patent Application No. 2002/0187948, PCT Application No. WO 02/087419 A2, U.S. Patent Application Publication No. US 2002/0155101A1 and U.S. Pat. No. 6,214,620.

Still, there is a need to improve current methods of using HCN to treat cardiac patients and create pacemaker current capable of being turned on, off and modulated as well as having the capability to react to physiological stimuli to ultimately restore physiological heart rates in patients suffering from arrhythmias.

SUMMARY OF THE INVENTION

The present invention is directed to methods of using HCN genes, variants or subunits thereof to treat a cardiac pacing dysfunction. The various isoforms of HCN that include HCN1, HCN2, HCN3 and HCN4, and modified HCN genes (e.g. truncated HCN4) may be combined to induce a pacemaker current and treat a patient in need thereof In addition, HCN genes can be combined with other types of genes including genes that promote beta-adrenergic receptors or genes that suppress $I_{k1}$ current to treat cardiac pacing dysfunction.

Specifically, genes that suppress or block $I_{K1}$ may be combined with HCN genes including variants or subunits of the HCN isoforms. This combination may prevent an instable cycle length created by the HCN gene alone. Further, one or more HCN genes may be combined together with other channel-focused genes that encode beta-adrenergic receptors to create biopacemakers with physiological heart rate and rate responses. Modifying the ratios and doses of the aforementioned genes can modify the gene-based biological pacemaker to induce different pacemaker currents.

The subject invention includes a method of using HCN3 alone or in combination with other isoforms of HCN and/or other genes to treat cardiac pacing dysfunction. The subject invention further includes a method of using a truncated HCN4 gene alone or in combination with other isoforms and/or variants of HCN and/or other genes to treat cardiac pacing dysfunction.

Genes may be delivered to the heart via a construct that is transfected into a cell in vitro, or via gene therapy in vivo. The HCN gene induces a slow depolarizing diastolic pacemaker current in atrial, ventricular or conductive tissue.

Further, genes may be introduced into cells via a viral vector or comparable delivery system. The genes can be transfected into target cells such as endogenous cardiac cells (e.g., atrial or ventricular myocytes, cells of the conduction system including SAV, AVN and Purkinje system, cardiac fibroblasts, etc.), stem cells (e.g. autologous, allogeneic or xenogeneic adult, fetal or embryonic stem cells), myoblasts or other cells. Endogenous cells such as atrial or ventricular cells are transfected using local delivery of a genetic therapy via catheter, direct injection, or equivalent delivery means. Other cells may be transfected outside of the body and then delivered to the heart using a catheter or equivalent means. For example, genetically modified cells may be delivered to the heart via self-fixating scaffolds.

Finally, by altering the molecular composition of the gene construct (e.g., adding certain promoters or regulatory elements to the HCN gene), the location, amount and characteristics of induced pacemaker current may be modified. Consequently, methods of subject invention may be specific for targeted cells instead of accidentally influencing, for example, a non-cardiac cell (e.g., a brain cell). Also, the pacemaker current can be regulated by controlling the expression of the transfected gene using, for example, pharmaceuticals that are directed towards the promoters of the transfected gene.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following description taken in conjunction with the accompanying drawings, in which.

DETAILED DESCRIPTION OF THE INVENTION

Figure 1:
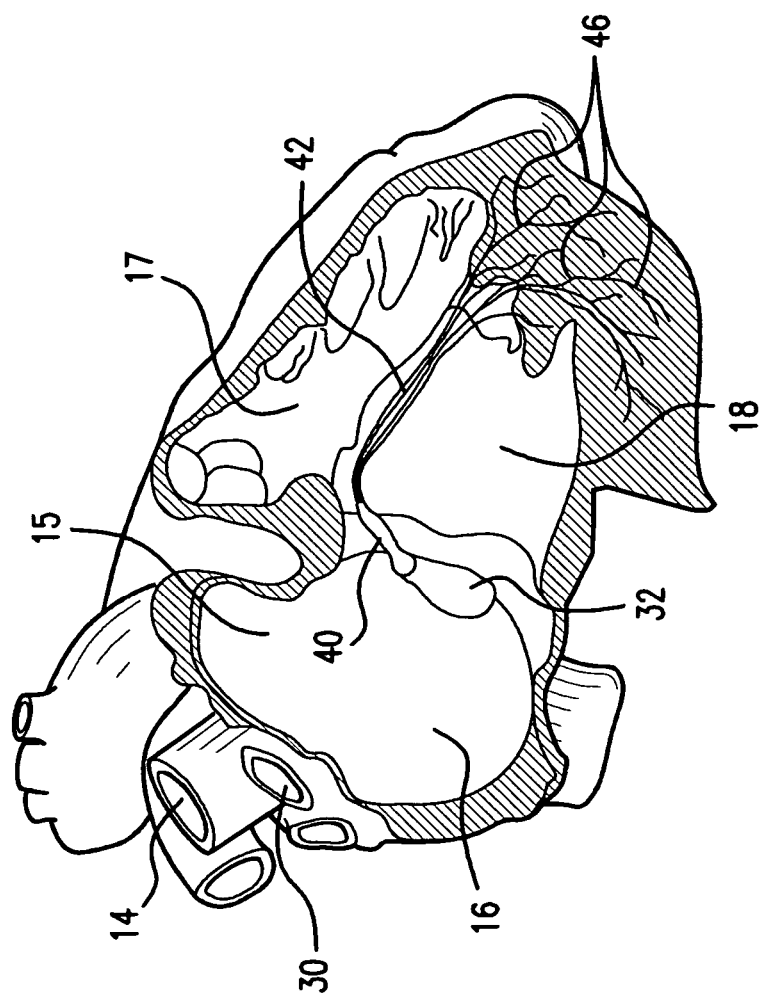
FIG. 1 is a diagram of a human heart.

The subject invention is directed to methods of treating patients with cardiac dysfunction by administering one or more HCN genes or variants thereof, alone or in combination with other genes.

Definitions

The following definitions are provided to facilitate an understanding of the invention.

"AAV" is an adeno-associated virus vector. These viruses cause no known disease in humans, hold long-term expression, and theoretically integrate at specific sites.

"AdV" is an adenovirus vector. These viruses cause the common cold. They have efficient entry into most cell types and can infect non-dividing cells. For gene therapy, these vectors are made replication-deficient by specifically deleting viral genes (e.g., E1, E2, E3 and/or E4). These genetically engineered vectors do not cause the common cold, although immune reactions to viral genes expressed in host cells can be observed.

"cDNA" includes all nucleic acids that share the arrangement of sequence elements found in native mature messenger ribonucleic acid (RNA) species, where sequence elements are exons (e.g., sequences encoding open reading frames of the encoded polypeptide) and 3' and 5' non-coding regions. Normally mRNA species have contiguous exons, with the intervening introns removed by nuclear RNA splicing, to create a continuous open reading frame encoding the polypeptide of interest.

"Channel protein" or "Ion channel protein" refers to proteins that transport ions across cell membranes.

"Chromosomes" are DNA molecules and their associated proteins. A gene is a unit of inheritance which occupies a specific locus on a chromosome and which has a specific sequence of nitrogenous bases. A genome is the total set of genes carried by an organism or cell.

"Construct" is a recombinant nucleic acid, generally recombinant DNA that has been generated for the expression of a specific nucleotide sequence(s), or is to be used in the construction of other recombinant nucleotide sequences.

"DNA," deoxyribonucleic acid, has a sugar group (deoxyribose) with the following nucleotide bases: adenine (A), guanine (G), thymine (T), and cytosine (C). RNA, ribonucleic acid, has ribose as the sugar group, and the same nucleotide bases, except uracil (U) replaces thymine. A single strand of DNA has a sequence of bases A, G, T, and C. When forming a DNA double-helix, for example, this secondary structure is held together by hydrogen bonds between bases on the neighboring strands. Note that in such base pairing, A always bonds to T and C always bonds to G.

"Coding sequence" refers to a nucleic acid sequence that is transcribed (in the case of DNA) and translated (in the case of mRNA) into a polypeptide, in vitro or in vivo, when placed under control of the appropriate regulatory sequences.

"Gap junction" refers to small pore-like proteins that connect cardiac muscle cells to each other.

"Gene" is a piece of DNA that encodes genetic traits and information.

"Gene cloning" is the process of identifying the gene responsible for a particular disease and synthesizing copies of it for use in treatment.

"Gene expression" describes the process by which a gene's coded information is converted into the structures present and operating in the cell. Expressed genes include those that are transcribed into mRNA and then translated into protein and those that are transcribed into RNA but not translated into protein (e.g., transfer and ribosomal RNAs).

"Gene therapy" is a technique for correcting genetic problems by introducing a "correct" copy of the gene into the patient's cells to compensate for their own defective gene. An alternative definition for "gene therapy" is the introduction of recombinant DNA into mammalian cells with the goal of modulating protein function (e.g., by expressing, replacing or suppressing a protein) for therapeutic purposes.

"Genome" is the complete set of genes in the chromosomes of each cell.

"Lentivirus" is a virus, such as HIV, that incorporates its passenger genes into non-dividing cells.

"Liposome" is a cationic lipid that is an artificially produced non-viral molecule vector that may transmit DNA to a cell. Sometimes this method is called facilitated DNA.

"Messenger ribonucleotide acid" or "mRNA" refers to RNA that serves as a template for protein synthesis.

"Nucleic acid" is a linear polymer of nucleotides (as in an oligomer, but longer) linked by 3',5' phosphodiester linkages.

"Nucleoside" is a purine or pyrimidine base linked glycosidically to ribose or deoxyribose.

"Nucleotide" is a phosphate ester of a nucleoside.

"Oligonucleotide" is a linear sequence of nucleotides, or mers, joined by phosphodiester bonds.

"PCR," or "polymerase chain reaction," is a system for in vitro amplification of DNA wherein two synthetic oligonucleotide primers, which are complimentary to two regions of the target DNA (one for each strand) to be amplified, are added to the target DNA in the presence of excess deoxynucleotides and Taq polymerase, a heat stable DNA polymerase. In a series of temperature cycles, the DNA is repeatedly denatured, annealed to the primers, and a daughter strand extended from the primers. As the daughter strands act as templates in subsequent cycles, amplification occurs in an exponential fashion. Since "traditional" PCR is a semi-quantative method at best, more recently, real-time (RT) PCR has been developed to allow quantification of RNA or DNA.

"Plasmid DNA" is circular DNA molecules typically found in bacteria.

"Polynucleotide" is an oligonucleotide, nucleotide, and fragments or portions thereof, as well as to peptide nucleic acids (PNA), fragments, portions or antisense molecules thereof, and DNA or RNA of genomic or synthetic origin which can be single- or double-stranded, and represent the sense or antisense strand.

"Promoter" is a minimal nucleotide sequence sufficient to direct transcription in a recombinant cell. "Promoter" is also meant to encompass those elements sufficient for promoter-dependent gene expression controllable for cell-type specific, tissue-specific or inducible by external signals or agents. Such elements may be located in the 5' or 3' regions of the native gene (e.g., enhancer elements).

"Regulatory gene or agent" is a gene with the primary function of controlling the rate of synthesis of the products of one or several other genes or pathways.

"Retrovirus" is a class of viruses that infects cells by inserting its own DNA into the genetic material of a host cell.

"Stem cells" are cells having the ability to divide for indefinite periods in culture and to give rise to specialized cells. Adult stem cells are undifferentiated cells found in a differentiated tissue that can renew itself and, with certain limitations, differentiate to yield all the specialized cell types of the tissue from which it originated. For example, adult resident cardiac stem cells have been identified. Bone marrow stromal cells are stem cells found in bone marrow that generate bone, cartilage, fat, and fibrous connective tissue. Mesenchymal stem cells are cells from the immature embryonic connective tissue. A number of cell types come from mesenchymal stem cells, including cardiac myocytes. Another example of adult stem cells are skeletal muscle progenitor cells. Embryonic stem cells are primitive, undifferentiated cells from the embryo that have the potential to become a wide variety of specialized cell types.

"Transformation", "transduction" or "transfection" refers to a permanent or transient genetic change induced in a cell following incorporation of a new nucleic acid (e.g., DNA or RNA exogenous to the cell). Genetic change can be accomplished either by incorporation of the new nucleic acid into the genome of the host cell, or by transient or stable maintenance of the new DNA as an episomal element.

"Transformed cell", "transfected cell" or "transduced cell" refers to a cell into which (or into an ancestor of which) has been introduced, by means of recombinant DNA techniques, a DNA molecule encoding a protein of interest.

"Transgene" is a gene that has other DNA inserted into it.

"Vector" refers to a means of transfecting cells with genetic material either in vivo or in vitro. Many such vectors are modified viruses.

The Cardiac Conduction System

FIG. 1 is a schematic diagram of a right side of a heart having an anterior-lateral wall peeled back to present a portion of a heart's intrinsic conduction system and chambers of a right atrium ("RA") 16 and a right ventricle ("RV") 18. Pertinent elements of the heart's intrinsic conduction system, illustrated, in FIG. 1, include a SA node 30, an AV node 32, a bundle of His 40, a right bundle branch 42, left bundle branches (not shown) and Purkinje fibers 46. SA node 30 is shown at a junction between a superior vena cava 14 and RA 16. An electrical impulse initiated at SA node 30 travels rapidly through RA 16 and a left atrium (not shown) to AV node 32. At AV node 32, the impulse slows to create a delay before passing on through a bundle of His 40, which branches, in an interventricular septum 17, into a right bundle branch 42 and a left bundle branch (not shown) and then, apically, into Purkinje fibers 46. Following the AVN delay, the impulse travels rapidly throughout RV 18 and a left ventricle (not shown). Flow of the electrical impulse described herein creates an orderly sequence of atrial and ventricular contraction and relation to efficiently pump blood through the heart. When a portion of the heart's intrinsic conduction system becomes dysfunctional, efficient pumping is compromised, potentially leading to symptoms which range from mild to life-threatening.

Typically, a patient, whose SA node 30 has become dysfunctional, may have an implantable pacemaker system implanted wherein lead electrodes are placed in an atrial appendage 15. The lead electrodes stimulate RA 16 downstream of dysfunctional SA node 30 and the stimulating pulse travels on to AV node 32, bundle of His 40, and Purkinje fibers 46 to restore physiological contraction of the heart. If a patient has a dysfunctional AV node 32, however, pacing in atrial appendage 15 will not be effective, since it is upstream of a block caused by the damage. In this situation, multiple chamber pacemaker system may be implanted (e.g. one pacemaker lead in the atrium, one in the ventricle), allowing for coordinated electromechanical activation of atria and ventricles.

Pacing at the bundle of His 40 provides the advantage of utilizing the normal conduction system of the heart to carry out ventricular depolarizations. In other words, stimulation provided at the bundle of His will propagate rapidly to the entire heart via the right bundle 42, the left bundle (not shown), and the Purkinje fibers. This provides synchronized and efficient ventricular contraction that is not replicated when the pacing is performed from the apex of the right ventricle because the electrical activity propagates via slowly conducting myocardial tissue as opposed to the rapidly conducting Purkinje network. By implanting biological pacemakers in or close to areas of physiological conduction (e.g. SAN, atrial septum, AVN, HIS bundle, Purkinje system), this principle could be applied to the current invention.

On the cellular level, electrical wave propagation occurs when cardiac cells allow a controlled flow of ions across the membranes through ion channels. This ion movement across the cell membrane results in changes in transmembrane potential (i.e., depolarization), which is a trigger for cell contraction. The heart cells can be categorized into several cell types (e.g. atrial, ventricular, etc.) and each cell type has its own characteristic variation in membrane potential. For example, ventricular cells have a resting potential of ~85 mV. In response to an incoming depolarization wave front, these cells fire an action potential with a peak value of ~20 mV and then begin to repolarize, which takes ~350 ms to complete. In contrast, SA nodal cells do not have a stable resting potential and instead begin to spontaneously depolarize when their membrane potential reaches ~−50 mV. Cells, such as SA nodal cells, that do not have a stable resting transmembrane potential, but instead increase spontaneously to the threshold value, causing regenerative, repetitive depolarization, are said to display automacity.

Cardiac muscle cells are structurally connected to each other via small pore-like structures known as gap junctions. When a few cardiac cells depolarize, they act as a current source to adjacent cells causing them to depolarize as well; and these cells in turn impose on further adjacent cells, and so on. Once depolarization begins within a mass of cardiac cells, it spreads rapidly by cell-to-cell conduction until the entire mass is depolarized causing a mass of cardiac cells to contract in a coordinated fashion.

The cells in the SA node are specialized pacemaker cells and have the highest firing rate. Depolarization from these cells spreads across the atria. Since atrial muscle cells are not connected intimately with ventricular muscle cells, conduction does not spread directly to the ventricle. Instead, atrial depolarization enters the AV node, and after a brief delay, is passed on to the ventricles via the bundle of His and Purkinje network, initiating cellular depolarization along the endocardium. Depolarization then spreads by cell-to-cell conduction throughout the entire ventricular mass.

The SA node's unique cells include a combination of ion channels that endow it with its automacity. Some of the unique features of the SA node cells, relative to other myocardial cells, include the absence of Na$^+$ channels ($I_{Na}$) and inwardly rectifying K$^+$ ($I_{K1}$) channels. In the absence of sodium current, the upstroke of SA node action potential is primarily mediated by L-type Ca$^{2+}$ channels ($I_{CaL}$). SA node cells do not have a stable resting potential because of their unique distribution of ion channels (e.g. lack of $I_{K1}$, HCN expression). Consequently, they begin to depolarize immediately after the repolarization phase of the action potential is complete. The maximum diastolic potential for SA node cells is approximately −50 mV compared to −78 mV and −85 mV for atrial and ventricular cells, respectively. The slow depolarization phase is partially mediated by activation of the hyperpolarization-activated cyclic nucleotide channels ($I_f$ current) and T-type Ca$^{2+}$ channels and deactivation of slow and rapid potassium channels ($I_{Ks}$ and $I_{Kr}$, respectively), in conjunction with a lack of $I_{K1}$ current which serves in non-automatic atrial and ventricular cardiac myocytes as a membrane potential stabilizing current. The rate of pacemaker discharge in the SA node in a normally functioning heart is approximately in the range of about 60 to 100 beats per minute at rest.

In a heart with dysfunctional SA node pacemaker function, the other structures of the heart with intrinsic pacemaking activity can take over the pacing function. The ectopically-driven escape rhythm produced by these structures, however, is slow (bradycardia) and normally not sufficient to support normal circulation (symptomatic bradycardia). A symptomatic bradycardia can manifest itself as syncope (temporary loss of consciousness) which may be life-threatening.

A method of the present invention includes genetically modifying the atrial cells, ventricular cells or cells of the cardiac conduction system, such as the Purkinje fibers, to modify the electrophysiology and pacing rate to resemble more closely the electrophysiology and pacing rate of the specialized pacemaker cells of the troubled SA or AV nodes. FIGS. 14 through 17 depict HCN3 and HCN4 single cell patch-clamp electrophysiology data for cells transduced with constructs containing HCN3, HCN4 and HCN4 truncated ("HCN4tr").

Native cells could also be transduced in a similar fashion. Subsequently their previously stable resting potential would be characterized by slow repeated phase 4 depolarizations and ultimately leading as the dominant pacemaker site of the heart. Similarly, cells could be stably transduced with the constructs described in FIGS. 14-17, and then transplanted to the myocardium. These cells could, once electrically coupled to native cardiac cells, depolarize the native cells and induce biological pacemaking as described with the more classical gene therapy approach. If the transplanted cells are of a cardiac phenotype (such as c-kit positive cardiac stem cells), then these cells could act as pacemaker cells themselves since they would express the necessary ion channel proteins for action potential generation as well as electrical coupleing (e.g. gap junction channel proteins).

Selection of Gene Construct

The human SA node does not consist of a group of uniform sinoatrial node cells embedded in atrial muscle. Instead, the SA node is a heterogeneous tissue with multiple cells types and a complex structure. From the periphery to the center of the SA node, there is a gradient in action potential shape, pacemaking, ionic current densities and connexin expression. In short, the SA node is a complex structure that, when afflicted with any level of dysfunction, may need to be augmented or replaced with several different types of genetic therapy to address the various problematic ion channels.

As previously noted, the HCN isoforms (e.g., HCN2 by itself instead of coupled to HCN4 in a functional heteromer) have different activation kinetics that consequently result in different HR ranges. Therefore, to simulate the complex SA node and its complex current, a variety of transfected genes may be required in a gene or cell therapy aimed at pacing dysfunction. Such a variety of genes can be obtained by using any one of the four different HCN isoforms, combinations of HCN isoforms in the form of heteromers or as multiple independent isoforms, or combinations of an HCN isoform or heteromer with other genes that affect heart rate. The heteromerization of the isoforms changes pacemaker electrophysiology via altered activation kinetics (e.g., allows for modulation (increase or decrease) of heart rate). Much B et al. J of Biol Chem; 44 (31): 43781-43786. While the exact stoichiometry of the heteromerized HCN channels has not been described yet, it is considered that these channels may form heteromers with a 3:1 ratio, but ratios of 1:1 or 1:3 are also possible as the HCN channels are known to form tetramers. In related rod photoreceptor cyclic nucleotide-gated channels, an asymmetrical stoichiometry of the two subunits present in the tetramers of 3:1 was determined. See, Zhong H et al. Nature 2002; 420: 193-196; See also, Weitz D et al. Neuron 2002; 36: 881-889 and Zheng J et al. Neuron 2002; 36: 891-896.

HCN3, or subunits thereof, is delivered to the heart in order to induce a slow depolarizing diastolic pacemaker current in atrial, ventricular or conductive tissue. See SEQ ID NO: 3. While HCN3 has not previously been considered as a gene therapy for pacing dysfunction, HCN3 can be used in a biopacemaker because, in part, HCN3 has similar kinetics to HCN2 (which is found in the heart). In fact, the homology between the two genes is approximately 86%. More importantly, the small current that is associated with HCN3 is significant in allowing for precise manipulation of biopacemaker current. Much et al., *Role of Subunit Heteromerization and N-Linked Glycosylation in the Formation of Functional Hyperpolarization-activated Cylic Nucleotide-Gated Channels,* J. Biol. Chem. (2003) 278: 43781-43786. Furthermore, HCN3 is smaller in size than HCN1, HCN2 or HCN4. Consequently, it fits easily in a viral vector with limited "transgene carrying capacity" such as AAV. In addition, overexpression of HCN3 can strengthen the small current normally associated with the gene. Also, because HCN3 is not naturally present in the heart, but rather in the brain, a successful transfection of the gene into cardiac tissue is more readily identifiable than channels induced by, for example, HCN2, which are commonplace in cardiac tissue.

Various combinations of HCN genes (e.g., HCN3 and HCN4) may be delivered to the heart in order to induce a pacemaker current. See SEQ ID NOS: 1, 2 and 4. The HCN genes may work independently of one another or as functional heteromers. Different heteromers result in different voltage activation thresholds and channel kinetics that in turn result in different heart rate capacities. Other characteristic changes occur in the resultant AP associated with the transfected tissue. For example, certain HCN isoforms, such as HCN1, are not very responsive to cAMP whereas combining isoforms may result in a heteromeric channel which is more sensitive to cAMP.

Regarding heteromer formation, only one pair of channel subunits, HCN2 and HCN3, do not form a functional heteromer. HCN3 is resistant to forming heteromers. Therefore, as a consequence, expression is more predictable. Coexpression of HCN2 and HCN3 produces a current density less than that of cells that only express HCN2. The following combinations may all be used to vary the resultant current density: HCN1/HCN2, HCN1/HCN3, HCN1/HCN4, HCN2/HCN3, HCN2/HCN4 and HCN3/HCN4. When no heteromer is created, co-expression of two HCN genes still produces current levels that may be needed to obtain a desired pacemaker current. Coexpression of three or more subunits allows for further still more complicated channels with varying resultant pacemaker currents.

In mammalian hearts, different isoforms of HCN are being expressed. See review in Trends Cardiovasc Med. 2002 July; 12(5):206-12. For example, HCN2 is considered to be the primary isoform in atria and ventricles, while HCN4 is predominantly expressed in sinoatrial and atrioventricular nodal cells. Therefore, by administering an exogenous HCN isoform via gene therapy, it is very likely that heterodimer formation does occur in vivo. To proof this, we studied hyperpolarization activated (If) current in HL-5 cells, a cardiac cell line. See FIGS. 12 and 13. This cell line is a clone from HL-1 cells. In these cells, HCN expression has been shown, with the strongest signals for HCN2 mRNA, followed by HCN1 and little HCN3, and no HCN4. See, Journal of Physiology. 2002 545(1):81-92. Expression of HCN4 clearly changes the activation kinetics of If. See e.g., FIG. 12. The activation kinetics of endogenous HCN channels is distinct from HL-5 cells expressing HCN4-truncated. The resulting activation kinetics is also distinct from truncated HCN4 expressing HEK 293 cells. This suggests that heterodimer formation occurs also in vivo. This could be exploited therapeutically, for example by choosing different isoforms based on the specific delivery site (e.g. Purkinje system, AVN may require a different isoform than right atrial septum)

HCN genes or various combinations of HCN genes may also be combined with other genes and delivered to the heart in order to induce a pacemaker current. In addition, the non-HCN genes may be supplied independently of HCN genes. The non-HCN genes may, for example, increase the expression of a particular ion channel or suppress, in whole or in part, the expression of function of an ion channel. Such non-HCN genes can be made by traditional PCR-based amplification and known cloning techniques. Alternatively, such a gene or polynucleotide can be made by automated procedures that are well known in the art. Such a polynucleotide should include a start codon to initiate transcription and a stop codon to terminate translation.

One example of such a non-HCN gene encodes beta-adrenergic receptors (e.g., types 1 and 2) that increase HR when exposed to circulating catecholamines or norepinephrine that is released from sympathetic neurons. See SEQ ID NOS: 5-6.

Another example involves DNA that will suppress the KCNJ2 gene encoding for the inward potassium rectifier channel2.1 (Kir2.1) that regulates $I_{k1}$ current. See SEQ ID NO: 10. Voltage-gated potassium ($K_v$) channels represent the most complex class of voltage-gated ion channels from both functional and structural standpoints. Their diverse functions include regulating neurotransmitter release, heart rate, insulin secretion, neuronal excitability, epithelial electrolyte transport, smooth muscle contraction, and cell volume. This gene encodes a member of the potassium channel, voltage-gated, isk-related subfamily. This member is a small integral membrane subunit that assembles with the KCNJ2 gene product, a pore-forming protein, to alter its function. This gene is expressed in the heart and its mutations are associated with cardiac arrhythmia.

Figure 6:
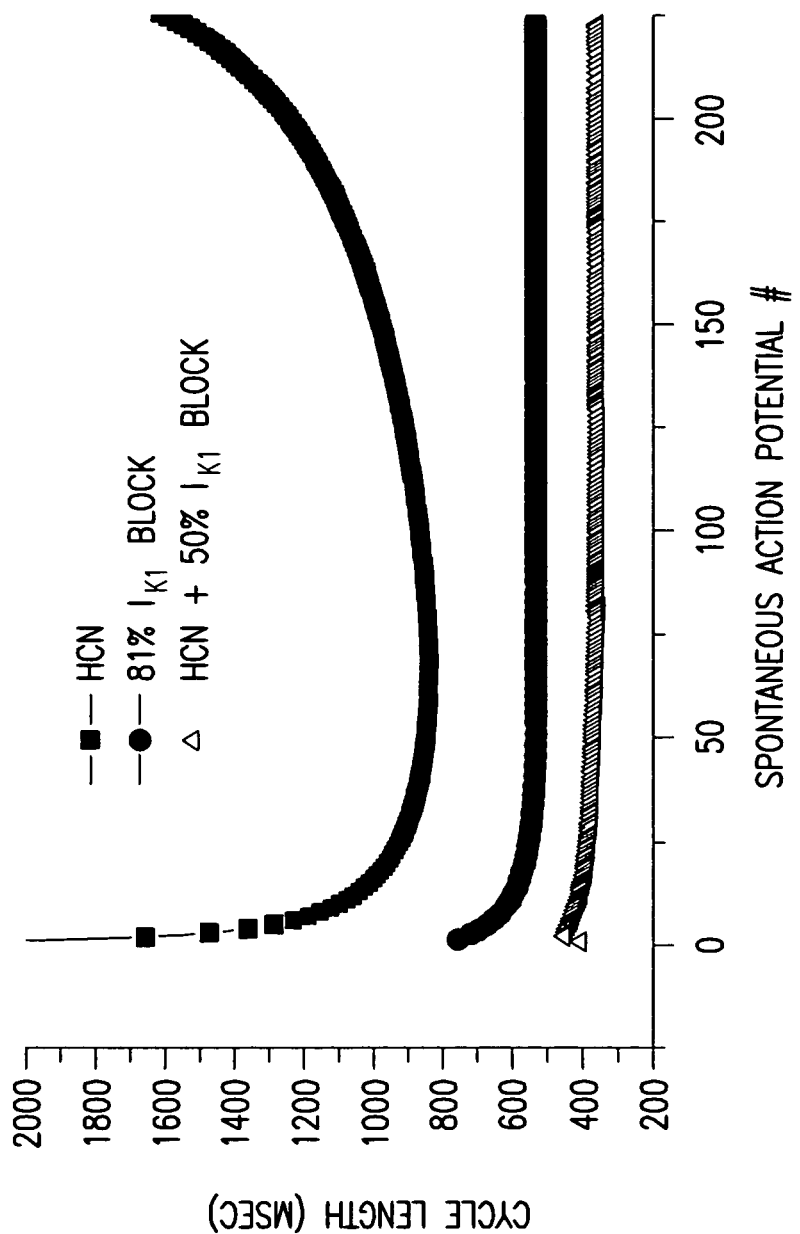
FIG. 6 is a recording of spontaneous action potential cycle lengths induced by HCN, $I_{k1}$-block and a combination HCN expression and $I_{k1}$-block.

The import of using this gene is expression of HCN in the ventricle leads to an unstable cycle length in silico. If $I_{k1}$ expression is decreased by about 50%, however, a stable cycle length (heart rate) is seen. See, FIG. 6. Moreover, if expression of $I_{K1}$ is further decreased to levels at or below 20%, then automaticity occurs in normal ventricular or atrial myocytes. This latter approach is described in detail in concurrently filed U.S. patent application claiming priority to U.S. Pat. App. Ser. No. 60/532,764. By combining the suppression of $I_{k1}$ with HCN expression, risks of action potential prolongation, increased dispersion of repolarization, ventricular tachycardia or fibrillation. and arrhythmogenesis may be further avoided. Therefore, a combination approach expression of HCN and suppression of $I_{K1}$ is beneficial.

Other regulatory proteins include muscarinic (M2) and/or (M3) receptors for enhanced parasympathetic control that can result in a decreased HR. See SEQ ID NOS: 11-12. Muscarinic receptors influence many effects of acetylcholine in the central and peripheral nervous system. The muscarinic cholinergic receptor 2 is involved in mediation of bradycardia and a decrease in cardiac contractility. The muscarinic cholinergic receptors belong to a larger family of G protein-coupled receptors. A typical control signal mediated via the vagus nerve leads to a local release of acetylcholine (Ach) in the sinoatrial and atrioventricular nodes. Ach then binds to the M2 receptor, activates an inhibitory G protein (Gαi), and essentially decreases the activity of adenylate cyclase, which directly leads to opening of K+ channels. In the sinoatrial node, vagal stimulation tends to flatten the diastolic depolarization, which then induces a slowing of heart rate (bradycardia, negative chronotropic effect), not only via the effects of reduced cAMP availability on if current (hyperpolarization activated cyclic nucleotide-gated channel), but also via activation of a potassium outward current. In the atrioventricular nodal tissue, vagal stimulation also activates an inhibitor G protein, which causes a slowing conduction velocity via a decreased calcium influx through L-type calcium channels. Clinically, the effects of vagal stimulation on the atrioventricular node are detected as increased atrioventricular nodal conduction times (e.g., prolonged PR interval).

In addition, the cells of the conduction system are genetically modified to increase the inward $Ca^{2+}$ current by delivering a bio-pacemaker composition to these cells. As a specific example, for the Purkinje fibers, the composition includes a coding sequence that encodes a T-type $Ca^{2+}$ channel resulting in the exogenous expression of T-type $Ca^{2+}$ channels. More specifically, as an example, genes that promote T-type calcium channel overexpression (e.g., CaV3.1) are another example of this additional gene. Alpha-1 subunits of Ca(2+) channels, such as CACNA1H, consist of 4 homologous repeat domains. Each domain has six transmembrane segments, a highly conserved pore loop, and a distinctive voltage sensor. The voltage dependence and fast inactivation of CACNA1H results in transient, or T-type, electrical currents. See SEQ ID NOS: 7-8. Exogenous expression of this channel will facilitate the depolarization characteristics of, for example, Purkinje fiber cells necessary to increase their intrinsic pacing rate.

Another suitable polynucleotide encodes human voltage-gated channel (KCND3). See SEQ ID NO: 14. This is one of the subunits responsible for $I_{to}$ (transient outward current). It is beneficial to suppress this gene (e.g., via siRNA, via dominant negative approaches, via ribozyme) to prolong action potential durations thereby mimicking the electrophysiology of SA nodal cells.

Yet another gene is the Human $K_V$ channel interacting protein 2, SEQ ID NO: 15. This presents another option for modulating $I_{to}$ by suppressing this protein.

Non-human protein examples include, but are not limited to, Rabbit minK-related peptide, SEQ ID NO: 9, and HCN1, SEQ ID NO: 24, Rat HCN1-HCN4, SEQ ID NOS: 16-19, Mouse HCN1-HCN4, SEQ ID NOS: 20-23 and Rainbow Trout HCN1, SEQ ID NO: 25.

Other suitable polynucleotides useful in connection with the invention can be obtained from a variety of sources including, without limitation, GenBank (National Center for Biotechnology Information (NCBI)), EMBL data library, SWISS-PROT (University of Geneva, Switzerland), the PIR-International database; the American Type Culture Collection (ATCC) (10801 University Boulevard, Manassas, Va. 20110-2209); National Center of Biotechnology Information (available online) and PubMed (available online), both associated with the National Library of Medicine and National Institute of Health; PubMed Controlling the Selected Gene Construct.

For site-specific expression of the transgene, tissue-specific promoters are made a part of the expression system. This tissue-specific expression significantly enhances the safety of the gene therapy as expression in non-target tissue becomes very unlikely.

For example, cardiac tissue specific promoters allow cardiac myocyte specific expression of the transgene of interest (including expression in stem cells with cardiac phenotype). As an example of one such promoter, a myosin heavy chain or myosin light chain promoter could be part of the expression system allowing transgene (e.g., HCN4) expression only in tissue containing this promoter (i.e., cardiac myocytes). Other examples of cardiac tissue specific promoters include, as examples, cardiac ankyrin repeat protein (U.S. Pat. No. 6,451,594), alpha-myosin heavy chain gene, beta-myosin heavy chain gene, myosin light chain 2 v gene a myosin light chain enhancer followed by either a myosin-heavy chain promoter or a viral promoter and a polynucleotide sequence (U.S. Published Patent Application 2002/025577 A1), myosin light chain 2a gene, cardiac alpha-actin gene, cardiac M2 muscarinic acetylcholine gene, ANF (ANP) atrial natriuretic factor (or peptide), cardiac troponin C, cardiac troponin I, cardiac troponin T or cardiac sarcoplasmic reticulum Ca-ATPase gene.

Specific promoters for the conductive system could also be employed if the site of the biological pacemaker is targeted at the cardiac conduction system. As an example, constructs of the present invention can be targeted to cells of the Purkinje network by methods known to those skilled in the art. Advantage can be taken of the expression of cell surface receptors unique to specific cells. For instance, one such receptor, preferentially expressed on the surface of Purkinje cells, is the cysteinyl leukotriene 2 receptor ($CysLT_2$). This receptor distinguishes Purkinje cells from neighboring cells such as ventricular cells and can be utilized to target constructs of the invention preferentially to Purkinje cells. In the practice of the present invention, however, any receptor specific to Purkinje cells may be utilized for specific targeting.

Targeted delivery requires the modification of the vehicle delivering the construct (which will be more fully developed below). Several methods for modification of such vehicles are possible. For example, viral protein capsids or proteins of the viral envelope may be biotinylated for subsequent coupling to a biotinylated antibody directed against a specific receptor or ligand via a strepavidin bridge.

Alternatively, the viral delivery vehicle may be genetically modified so that it expresses a protein ligand for a specific receptor. The gene for the ligand is introduced within the coding sequence of a viral surface protein by, for example, insertional mutagenesis, such that a fusion protein including the ligand is expressed on the surface of the virus. For details on this technique see Han et al., "Ligand-Directed Retroviral Targeting of Human Breast Cancer Cells," *Proc. Natl. Acad. Sci.*, 92:9747-9751 (1995). Viral delivery vehicles may also be genetically modified to express fusion proteins displaying, at a minimum, the antigen-binding site of an antibody directed against the target receptor. See e.g., Jiang et al., "Cell-Type-Specific Gene Transfer into Human Cells with Retroviral Vectors That Display Single-Chain Antibodies," *J. Virol.*, 72: 10148-10156 (1998).

An embodiment of the invention may also involve regulation of the transgene via regulatory elements such as drug-sensitive elements (e.g., a drug-inducible suppressor or promoter). Drug-responsive promoters may induce or suppress gene expression. For example, a tetracycline responsive element (TRE) that binds doxycycline is present within the promoter construct. When doxycycline is removed, transcription from the TRE is turned off in a highly dose-dependent manner. Examples of inducible drug-responsive promoters are the ecdysone-inducible promoter (U.S. Pat. No. 6,214,620) and rapamycin-dependent expression (U.S. Pat. No. 6,506,379). See Discher et al., J. Biol. Chem (1998) 273: 26087-26093; Prentice et al., Cardiovascular Res. (1997) 35: 567-576.

Other promoters, for example, would be sensitive to electrical stimulus that could be provided from, for example, an implantable device. Electrical stimulation can promote gene expression (U.S. Patent Application No. 2003/0204206 A1). This would allow for turning automaticity of the cells on and off, or modulating there between.

Delivering the Selected Gene Construct

The gene construct may be transfected into target cells such as endogenous cardiac cells (e.g., myocytes), stem cells, myoblasts or other cells. Endogenous cells such as atrial or ventricular cells or cells of the conduction system are transfected using local delivery of a genetic therapy via catheter, direct injection, or equivalent delivery means. Other cells may be transfected outside of the body and then delivered to the heart using a catheter or equivalent means. For example, as will be appreciated by those skilled in the art, cardiac myocardial cells derived from stem cells may be treated with the genetic procedures described herein and implanted into a region of the conduction system (e.g. Purkinje fiber) with a catheter or by direct injection to Purkinje fiber tissue.

The genetic construct can be delivered into a cell by, for example, transfection or transduction procedures. Transfection and transduction refer to the acquisition by a cell of new genetic material by incorporation of added nucleic acid molecules. Transfection can occur by physical or chemical methods. Many transfection techniques are known to those of ordinary skill in the art including, without limitation, calcium phosphate DNA co-precipitation, DEAE-dextrin DNA transfection, electroporation, naked plasmid adsorption, and cationic liposome-mediated transfection. Transduction refers to the process of transferring nucleic acid into a cell using a DNA or RNA virus. Suitable viral vectors for use as transducing agents include, but are not limited to, retroviral vectors, adeno associated viral vectors, vaccinia viruses, adenoviral viruses, epstein barr viruses, coxsackie viruses and sendai viruses.

The selection of a delivery means at the cellular level should address the length of desired expression. For example, where permanent pacing therapy is desired, an adeno-associated virus (AAV) encoding HCN4 and an additional AAV encoding regulatory receptor proteins, such as beta-adrenergic or muscarinic receptors, is implemented. AAVs have good long-term expression qualities because of their ability to integrate their genome into non-dividing cells in addition to their minimal immune response.

AAV vectors can be constructed using techniques well known in the art. Typically, the vector is constructed so as to provide operatively linked components of control elements. For example, a typical vector includes a transcriptional initiation region, a nucleotide sequence of the protein to be expressed, and a transcriptional termination region. Often, such an operatively linked construct will be flanked at its 5' and 3' regions with AAV ITR sequences, which are required viral cis elements. The control sequences can often be provided from promoters derived from viruses such as, polyoma, Adenovirus 2, cytomegalovirus, and Simian Virus 40. Viral regulatory sequences can be chosen to achieve a high level of expression in a variety of cells. Alternatively, ubiquitous expression promoters, such as the early cytomegalovirus promoter can be utilized to accomplish expression in any cell type. A third alternative is the use of promoters that drive tissue specific expression (addressed above). This approach is particularly useful where expression of the desired protein in non-target tissue may have deleterious effects. Thus, according to another preferred embodiment, the vector contains the proximal human brain natriuretic brain (hBNP) promoter that functions as a cardiac-specific promoter. For details on construction of such a vector. See, LaPointe et al., "Left Ventricular Targeting of Reporter Gene Expression In Vivo by Human BNP Promoter in an Adenoviral Vector," *Am. J. Physiol. Heart Circ. Physiol.*, 283:H1439-45 (2002).

Vectors may also contain cardiac enhancers to increase the expression of the transgene in the targeted regions of the cardiac conduction system. Such enhancer elements may include the cardiac specific enhancer elements derived from Csx/Nkx2.5 regulatory regions disclosed in the published U.S. Patent Application 2002/0022259.

Figure 10:
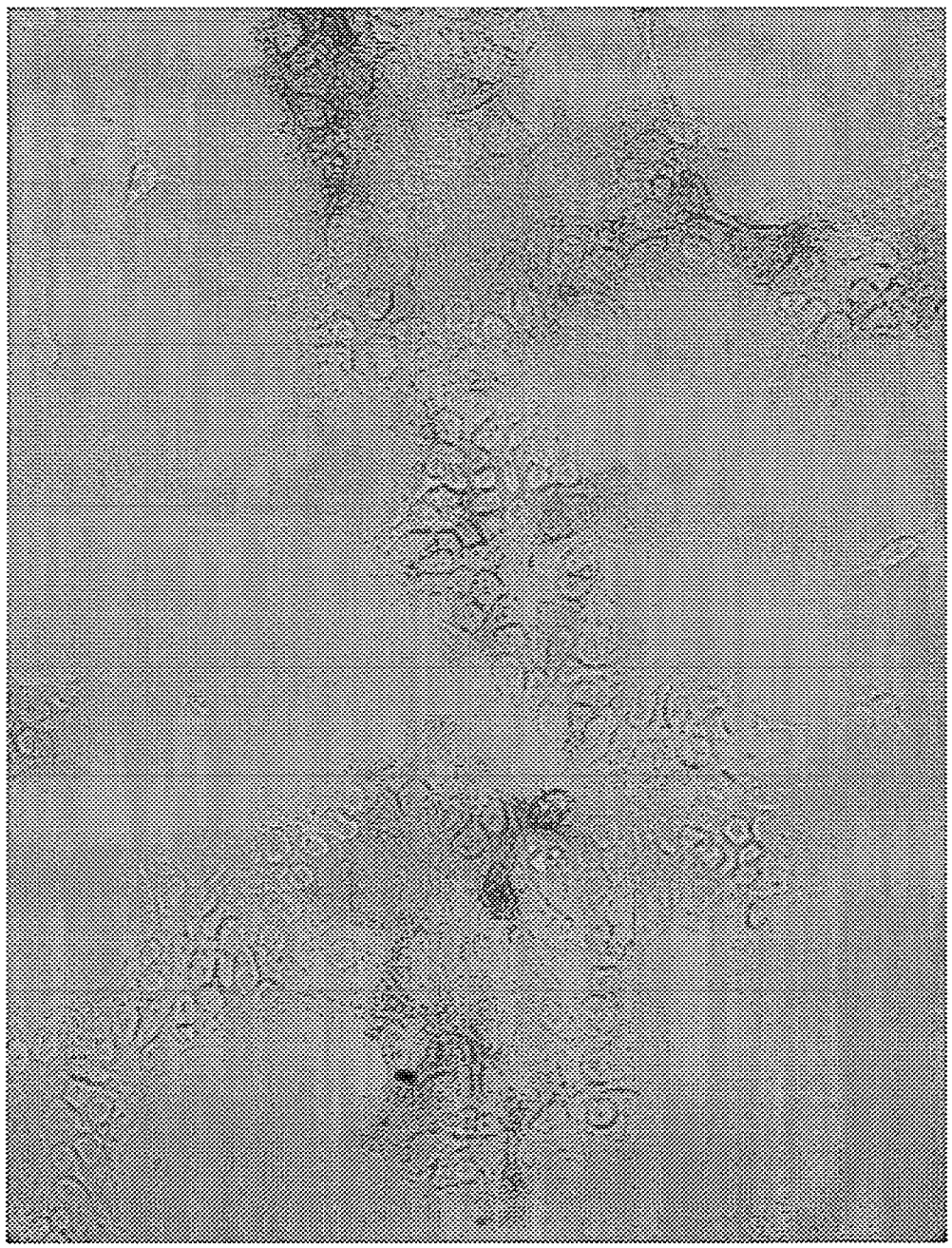
FIG. 10 depicts immunolabeling (c-myc antibody) of HEK 293 cells co-transduced cells with AAV1/2 HCN4tr and AAV1/2-eGFP.
Figure 11:
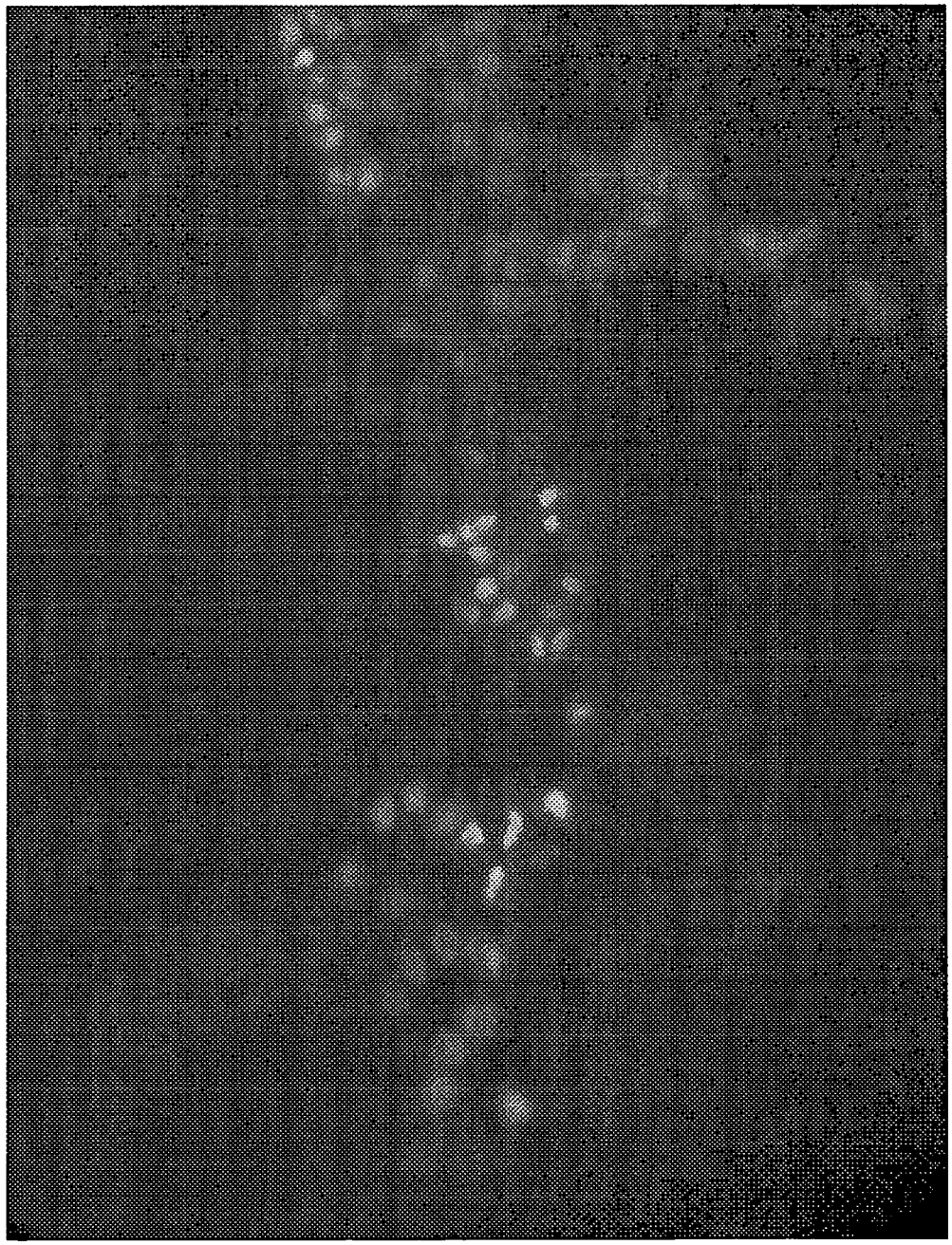
FIG. 11 depicts eGFP-labeling of the HEK 293 cells shown in FIG. 11 co-transduced cells with AAV1/2-HCN4tr and AAV1/2-eGFP.
Figure 12A:
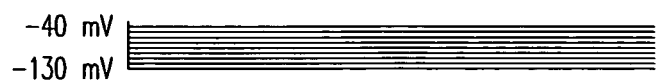
FIG. 12 depicts whole cell voltage clamp current traces of $I_f$ recorded from HL-5 cells.
Figure 12B:
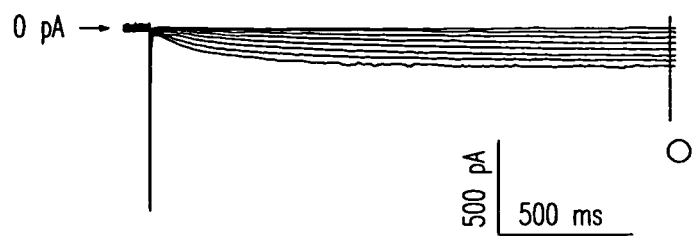
Figure 12G:
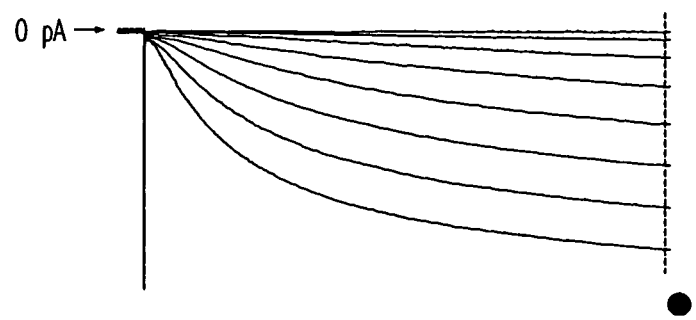
Figure 12D:
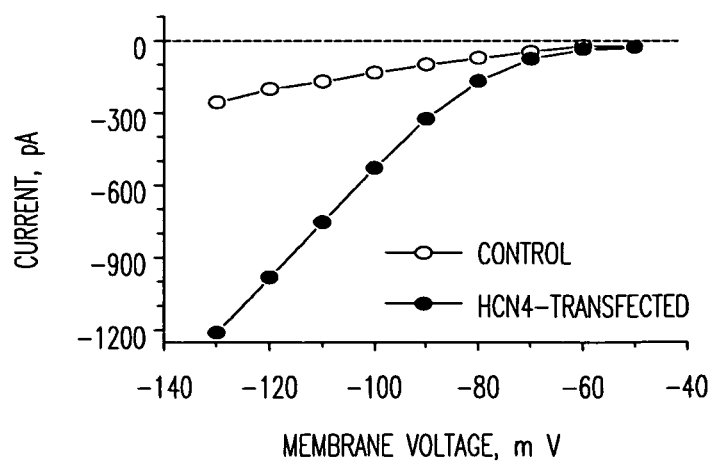

The subject invention may utilize an adeno-associated virus (AAV) but could also use a $2^{nd}$ or $3^{rd}$ generation adenovirus or others such as chimeric adeno-associated virus (AAV1/2) which is the chimeric product of AAV1 and AAV2 vectors. The AAV1 and AAV2 serotypes differ in composition of their capsid protein coat with resultant varying characteristics. The AAV2, for example, can be beneficial due to its known receptor binding and known approach for purification. AAV1 allows for good muscle transfection. Cross-packaging of a single AAV type 2 vector genome into multiple AAV serotypes enables transduction with broad specificity. AAV1/2 combines the advantages of these two vectors regarding, for example, purification and muscle transfection. FIG. 10 depicts an image of truncated HCN as expressed in cells that were transduced with constructs containing AAV1/2.

In one example of the invention, human HCN3 gene, SEQ ID NO: 3, can be cloned into a chimeric adeno-associated virus (AAV1/2) with the following sequence: AAV-CAG-humanHCN3-WPRE-BGHpolyA. A control vector encoding GFP is an adeno-associated virus (AAV1/2) with the following sequence: AAV-CAG-eGFP-WPRE-BGHpolyA. A CAG promoter (hybrid chicken B-actin/CMV enhancer) is used to achieve high transgene expression. Also, as a post-regulatory element, woodchuck postregulatory regulatory element (WPRE) can be used thereby allowing for increased transgene expression levels. Other common vectors are provided in U.S. Pat. Application No. US 2002/0155101A1. Suitable vectors can be obtained at GeneDetect.Com, 1455 Tallevast Road, Suite L8299, Sarasota, Fla. 34243 as well as other organizations known in the art.

Figure 3:
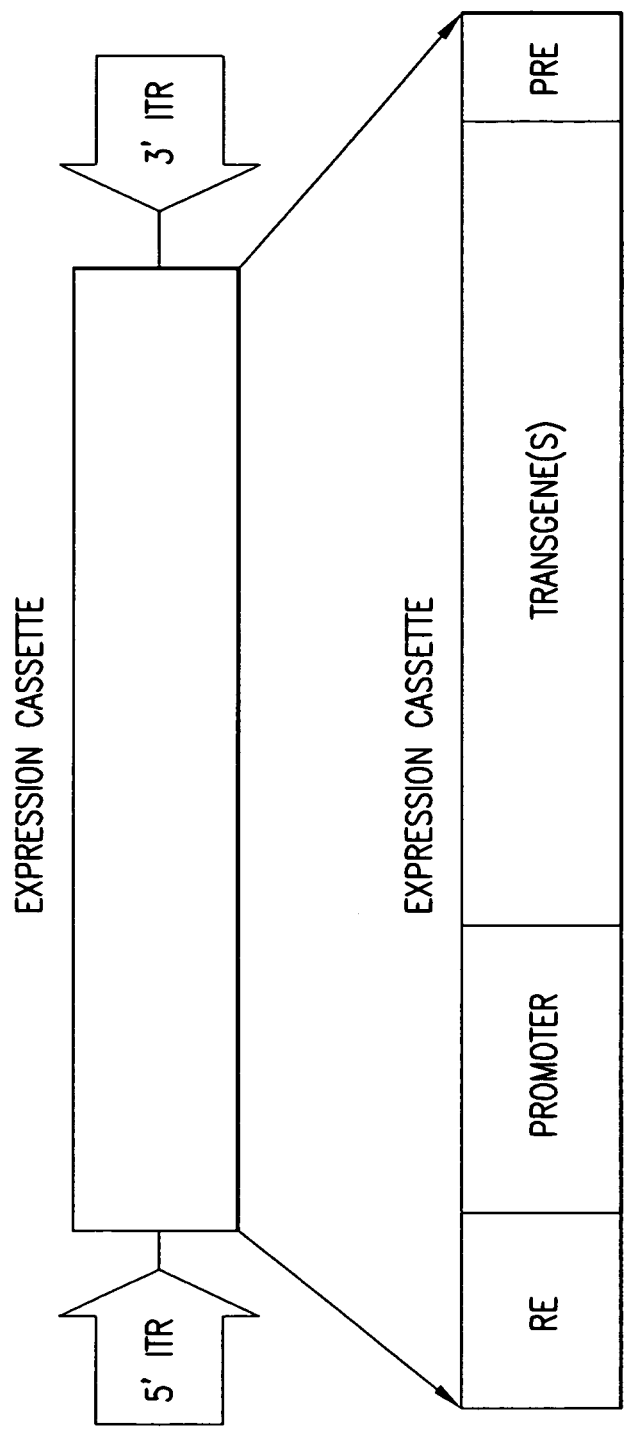
FIG. 3 depicts an example of a generic viral vector expression cassette that includes a promotor, regulatory elements and a transgene. ITR: Inverted terminal repeats; RE: Regulatory elements such as drug-sensitive elements; Promoter: Cardiac specific promoter, electrical promoter, constitutive promoter, other promoter; Transgene(s): HCNx plus beta-AR gene, HCNx plus HCNy, HCNx plus dominant negative Kir2.1 gene, other transgene; Note: based on packaging size of viral constructs, the viral vector could be an adeno-associated virus, a gutless virus, a lentivirus or different virus.
Figure 4:
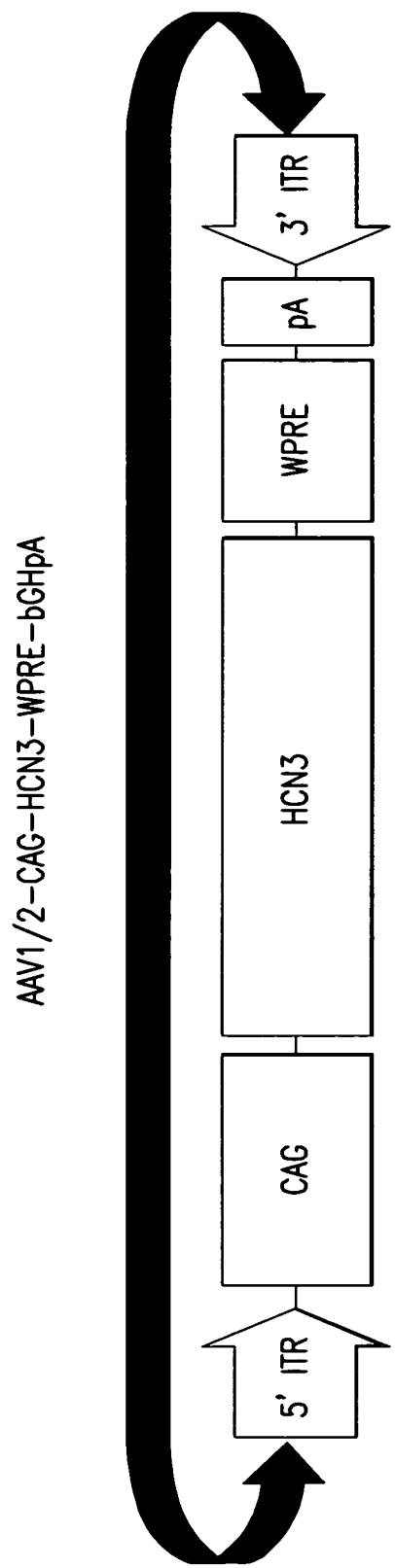
FIG. 4 depicts an example of a specific viral vector expression cassette that includes a promotor, regulatory element and the HCN3 gene for transfection. ITR: Inverted terminal repeats; CAG: chicken B-actin/CMV enhancer; hHCN3: human HCN3 gene, could be replaced with HCN1, HCN2 or HCN4 gene (may need to be truncated); WPRE: woodchuck post-regulatory enhancer; pA: BGHpA.
Figure 8:
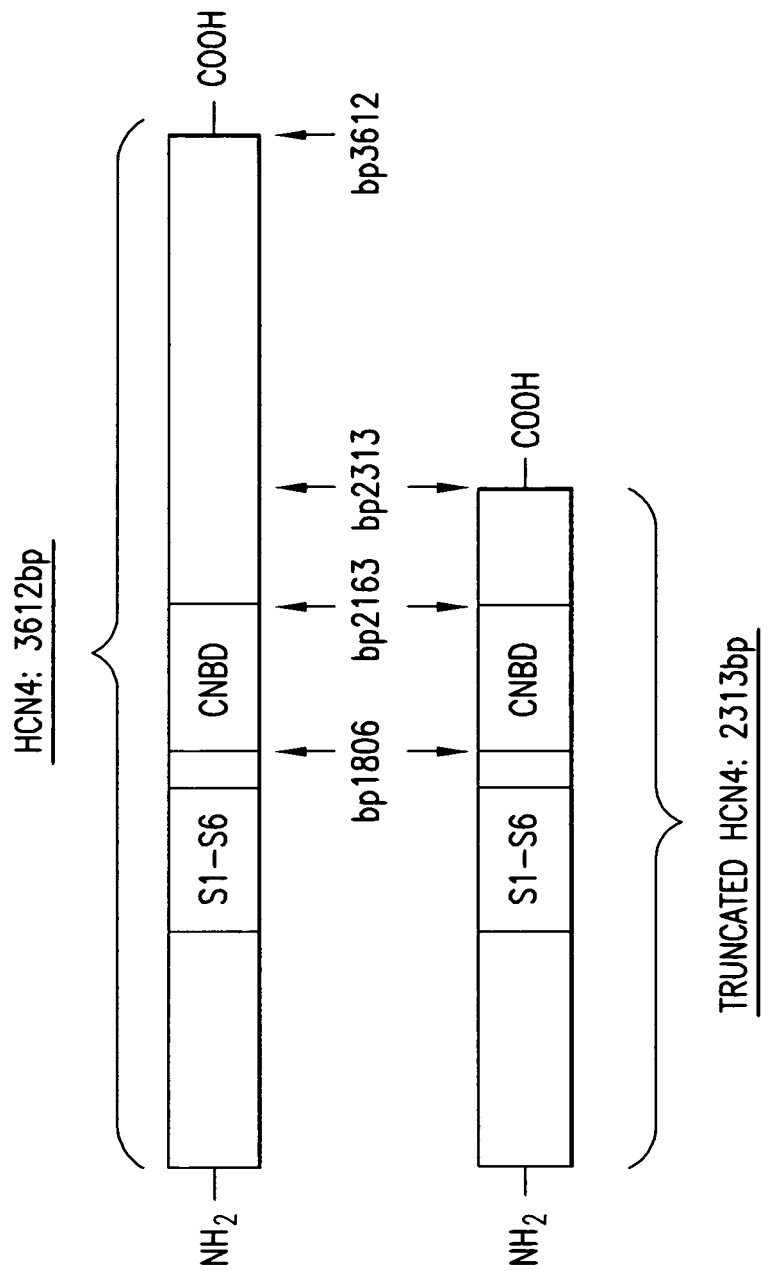
FIG. 8 depicts the complete length of native HCN4 compared to truncated HCN4.
Figure 9:
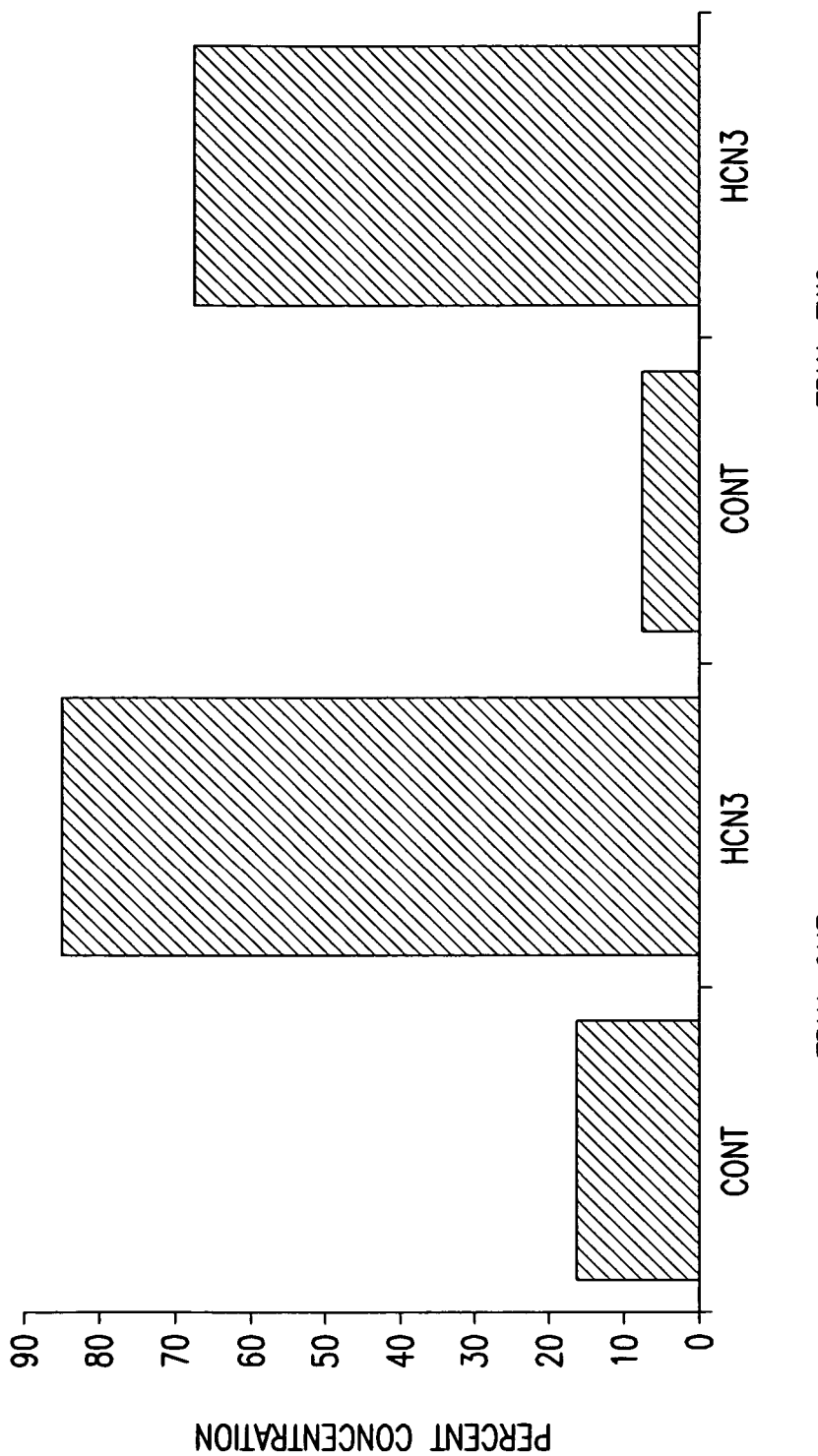
FIG. 9 depicts the expression data of two trials of HCN3 as transfected Human Embryonic Kidney (HEK) 293 cells by Quantitative Real-time Polymerase Chain Reaction (Q RT PCR).

When selecting a vector, using an AAV for example, a problem can arise if the HCN transgene does not fit into common AAV expression cassettes. Such problems are amplified when promoters and additional regulatory elements are included in the cassette. See, FIGS. 3 and 4. For example, when using GeneDetect's rAVE cassette, this problem is overcome with HCN3 (2,334 base pairs ("bp")) by removing a regulatory element (e.g., SAR) from the cassette. For HCN2 (2,670 bp), an additional element (e.g., WPRE) can be left out. For large genes such as HCN4 (3,612 bp), however, the transgene size must be further reduced by truncating the very large C-terminus. In one embodiment, truncation of the sequence occurs not before the cAMP binding site which still allows for a functional gene. For example, with HCN2, bp 2161-2670 may be truncated. Bp 1654-2010 is the cAMP binding site. As another example, with HCN3 bp 1813-2325 may be truncated. Bp 1306-1662 is the cAMP binding site. As an additional example, as depicted in FIG. 8, HCN4 may be truncated from base pair 3612 to base pair 2313. Here, base pairs 1807-2163 represent the cAMP binding site. As an additional example, with HCN1 the C-terminus, including the cAMP binding site, may also be truncated as this protein isoform demonstrates very little reponsiveness to cAMP binding.

Figure 2:
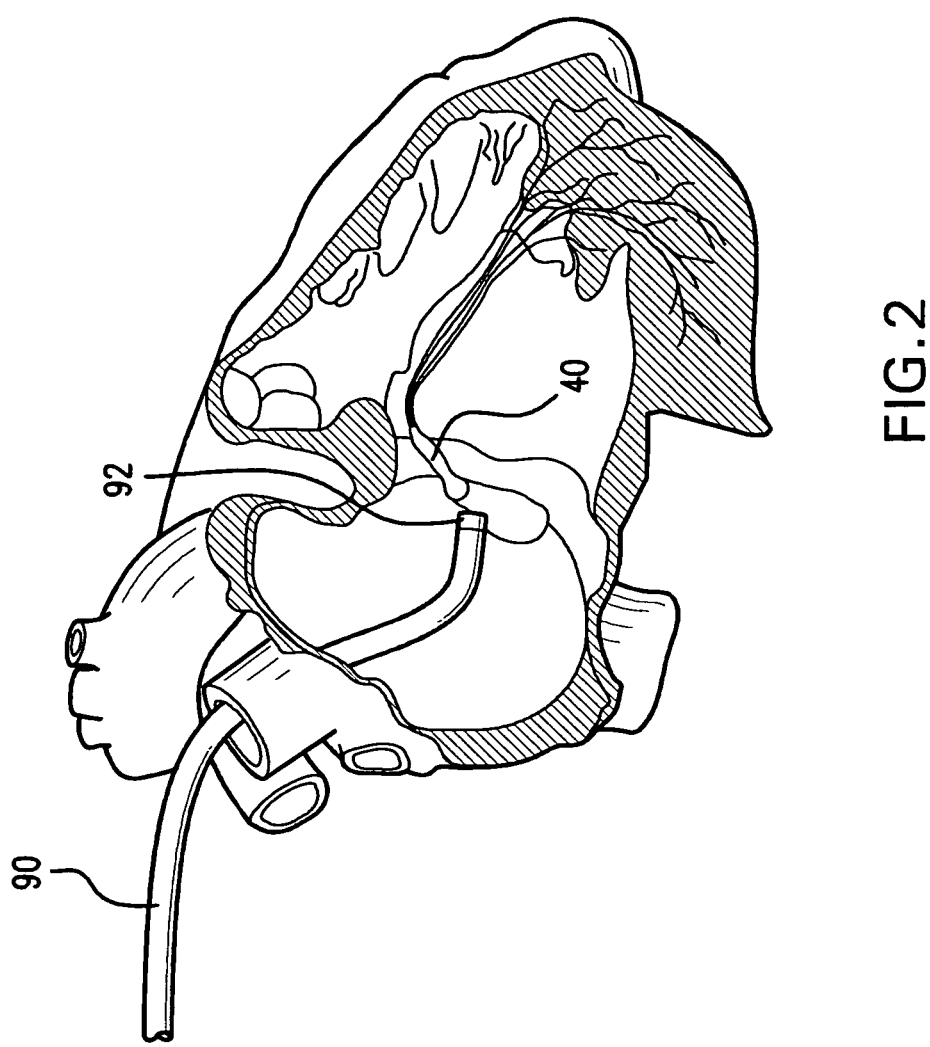
FIG. 2 is a diagram of the right side of a heart in which a guiding catheter is positioned for delivery of the genetic construct of the invention.

At the macro level (i.e., non-cellular level), various catheter means may be employed to deliver the gene construct to the heart tissue. FIG. 2 shows a guide catheter 90 being positioned for delivery of the genetic construct of the invention. A venous access site (not shown) for the catheter 90 may be in a cephalic or subclavian vein. Means used for venous access are well known in the art and include the Seldinger technique performed with a standard percutaneous introducer kit. The guide catheter 90 includes a lumen (not shown) extending from a proximal end (not shown) to a distal end 92 that slideably receives the delivery system 80. The guide catheter 90 may have an outer diameter between approximately 0.115 inches and 0.170 inches and be of a construction well known in the art. The distal end 92 of the guide catheter 90 may include an electrode (not shown) for mapping electrical activity in order to direct the distal end 92 to an implant site near certain pacing areas in the heart. Alternatively, a separate mapping catheter may be used within the lumen of the guide catheter 90 to direct the distal end 92 to an application site near certain areas of the heart. This method is well known in the art. Other catheter means are described in commonly-assigned co-pending U.S. patent application Ser. Nos. 10/262,046, filed Oct. 2, 2002; and 10/423,116, filed Apr. 23, 2003, both of which are incorporated herein by reference.

In short, delivery of a genetic construct can be carried out according to any method known in the art (e.g., syringe injection). It is only necessary that the genetic construct reach a small portion of the cells that are targeted for gene manipulation (e.g. cells of the Purkinje fibers). The genetic construct may be injected directly into the myocardium as described by R. J. Guzman et al., Circ. Res., 73:1202-1207 (1993). The delivery step may further include increasing microvascular permeability using routine procedures, including delivering at least one permeability agent prior to or during delivery of the genetic construct. Perfusion protocols useful with the methods of the invention are generally sufficient to deliver the genetic construct to at least about 10% of cardiac myocytes in the mammal. Methods for targeting non-viral vector genetic constructs to solid organs, for example, the heart, have been developed such as those described in U.S. Pat. No. 6,376,471. Additional non-injection methods for gene delivery include, but are not limited to, polymer-based gene-delivery (e.g. via coated devices, via biodegradable scaffolds), gene delivery via cells attached to a device or to a biodegradable scaffold, gene delivery via vascular or transvascular delivery into selected myocardial regions, gene delivery via aid of electroporation or gene delivery via other means.

As an example of solution concentrations and dosage levels, concentrations of $1 \times 10^7$ to $1 \times 10^{13}$ parts gene construct per 100 microliters of solution of phosphate buffered saline may be used in dosages of 20-200 microliters. Also, 1:1 concentrations of different HCN isoforms and other genes may be used (e.g., HCN4 and genes encoding beta-adrenergic receptors). Still, other concentrations and dosage levels will be apparent to those skilled in the art as the effective dose of the gene construct will be a function of the particular expressed gene(s), the particular cardiac arrhythmia to be targeted, the desired heart rate (e.g., 60-90 beats per minute at rest and appropriate modulation of heart rate during stress or exercise as well as during sleep), the patient and his or her clinical condition, weight, age and sex. Other examples include administering several dosages in several locations. For example, a primary biological pacemaker in the atrial septum may be utilized, and in case of AVN conduction block, a backup pacemaker (with a lower intrinsic rate) in the ventricle (e.g. myocardial cells of Purkinje system).

Verification of Enhanced Pacemaker Current

Methods for detecting modulation of the cells of the conduction system of the heart by electrophysiological assay methods relates to any conventional test used to determine the cardiac action potential characteristics, such as action potential duration (APD). Briefly, a standard electrophysiological assay includes the following steps: providing a mammalian heart (in vivo or ex vivo), delivering to the heart a genetic construct or modified cells of the invention, transferring the genetic construct and/or modified cells into the heart under conditions which can allow expression of an encoded amino acid sequence, and detecting the increase of electrical properties in the cells of the heart to which the genetic construct and/or modified cells were delivered, wherein at least one property is the pacing rate of the cells, relative to a baseline value. Baseline values will vary with respect to the particular target region chosen in the conduction system.

Additionally, modulation of cardiac electrical properties obtained with the methods of the invention may be observed by performing a conventional electrocardiogram (ECG) before and after administration of the genetic construct of the invention and inspecting the ECG results. ECG patterns from a heart's electrical excitation have been well studied. Various methods are known for analyzing ECG records to measure changes in the electrical potential in the heart associated with the spread of depolarization and repolarization through the heart muscle. A preferred method of monitoring the proper function of a biological pacemaker may be via an implantable pacemaker/defibrillator or an implantable loop-recorder (e.g. Medtronic's Reveal™). Other methods include placement of endocardial mapping electrode catheters to various locations in the heart, and record an intrinsic local electrical signal (EGM). These procedures require venous or arterial access to the endocardium of the atrial or ventricular tissue. These mapping catheters can be used in conjunction with analog or digital systems which range from simple electrophysiological assessments (e.g. GE Prucka system) to more complex electroanatomical maps of the heart (e.g. Carto or Endocardial Solutions systems). Such mapping procedures are well known in the art.

For whole-cell voltage-clamp experiments, using the following as an example, experiments may be conducted at room temperature using traditional instrumentation known in the art such as, but without limitation, an Axon Instruments 200A amplifier and Nikon Inverted Microscope (100T). Borosilicate glass microelectrodes (1-3 Megaohms) can be sealed to the lipid bilayer membrane of cells and the transmembrane currents at various holding potentials can be measured via a small rupture within the seal. The cells can be bathed in an extracellular-like solution that may include, but is not limited to, the following reagents and concentrations (in millimolar): NaCl (110), MgCl2 (0.5), KCl (30), CaCl2 (1.8), Hepes (5), and pH=7.4 (w/NaOH). Likewise, the microelectrode inner lumen may contain, but is not limited to, the following reagents and concentrations (in millimolar): NaCl (10), MgCl2 (0.5), KCl (130), EGTA (1), Hepes (5), and pH=7.4 (w/KOH).

The voltage clamp protocol involves a holding potential of −40 mV (1 second) and then conducting sweeps (3 second duration) in −10 mV steps from −40 mV to −140 mV. The last step of the protocol is either holding it at −40 mV or at −140 mV for 1 second.

Figure 5:
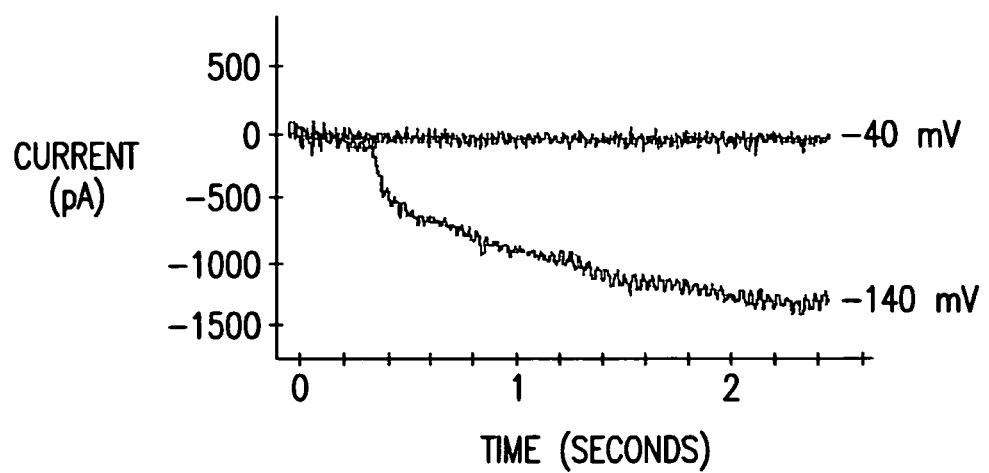
FIG. 5 is a recording of induced pacemaker current obtained from experiments using human embryonic kidney cells transfected with human HCN3 gene. Recordings were obtained from whole-cell patch clamp experiments.

FIG. 5 shows one example of the aforementioned patch clamp experimentation. The recordings were obtained from whole-cell patch clamp experiments using human embryonic kidney 293 (HEK 293) cells that were co-transfected with an adeno-associated virus encoding enhanced green fluorescent protein (AAV1/2-CAG-eGFP) and an adeno-associated virus encoding the human HCN3 gene (AAV1/2-CAG-HCN3). When the cells were hyperpolarized to −140 mV, a slowly activating inward current was detected that was characteristic of HCN channels. No inward current was detected in control cells (not transfected cells) or cells transfected only with AAV-eGFP when the voltage was held at −140 mV (data not shown).

Figure 7:
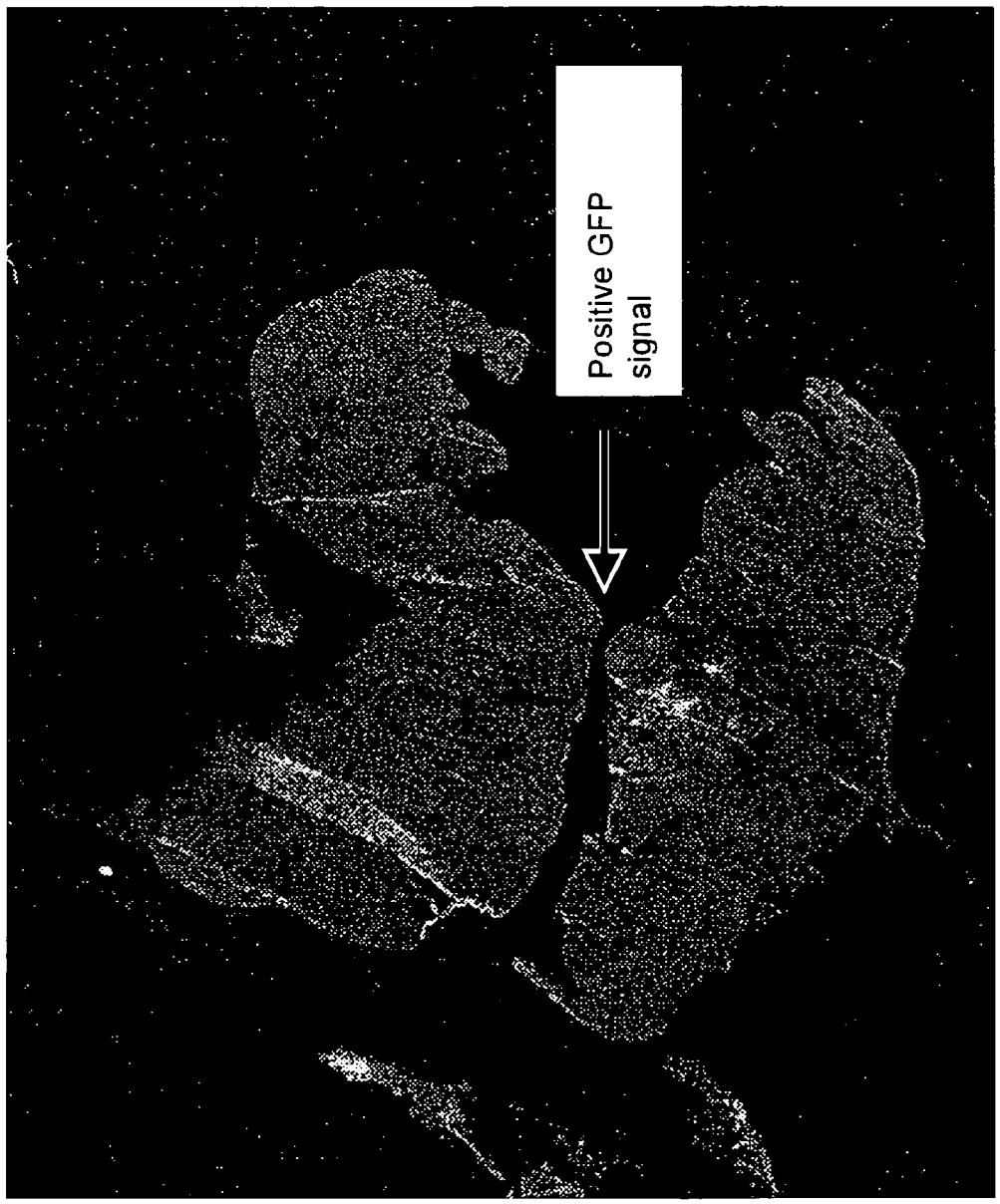
FIG. 7 depicts an image showing green fluorescent expression four weeks after injection of recombinant adeno-associated virus encoding enhanced green fluorescent protein (rAAV-eGFP) in canine myocardium.

FIG. 7 depicts a fluorescence microscopic image demonstrating positive GFP expression four weeks after injection of rAAV-eGFP into canine myocardium.

EXAMPLE I

HL-5 cells at passage 73 were cultured in gelatin-fibronectin coated 33 mm culture dishes. Cells were maintained in the medium (JRH Biosciences, Lenexa, Kans., USA), supplemented with 10% fetal bovine serum, 4 mM L-glutamine, 10 μM noradrenaline (norepinephrine; Sigma Aldrich, St. Louis, USA) and penicillin-streptomycin. The medium was changed every 24 h. HL-5 cells at different passages (from 75 to 98) were splitted when they reached a state of confluence. Dissociated cells were either re-plated for a new passage or used for patch clamp experiments. Some cells were transfected with rAAV-HCN4tr-cmyc. Cells were cultured at 37° C. under an atmosphere of 5% $CO_2$ and 95% air with approximately 95% humidity.

After dissociation from a culture dish, cells were plated on gelatin/fibronectin-coated coverslips for patch-lamp experiments. During an experiment HL-5 cells plated on a coverslip were transported to a chamber mounted on the stage of a Nikon microscope. The chamber was continuously superfused (~1 ml/min) with the Tyrode's solution, which contained (in mM): 140 NaCl, 5.4 KCl, 1.8 $CaCl_2$, 1 $MgCl_2$, 10 HEPES, and 10 glucose (pH 7.4 adjusted with NaOH). The whole-cell configuration of the patch-clamp technique (Hamill et al. 1981) was applied in the experiments. Briefly, glass electrodes (World Precision Instruments, Sarasota, Fla.) with 2-4 MΩ resistance were connected via a Ag—AgCl wire to an Axopatch 200A amplifier interfaced with a DigiData 1320 acquisition system. After forming a conventional "gigaohm" seal, electrode capacitance was compensated. Whole-cell configuration was achieved by rupturing the membrane with additional suction. Membrane capacitance and series resistance were compensated to reduce artifactual distortion. A perfusion system (Warner Instruments, Inc., Hamden, Conn., USA) was used to change the extracellular solution. Data were collected with the pCLAMP software (version 9.2, Axon Instruments, Foster City, Calif.). Experiments were conducted at room temperature (~23° C.).

Before electrical compensation, cell membrane capacitance ($C_m$) was measured in each patched cells with the pCLAMP program. During recordings, the cells were superfused with the modified Tyrode's solution to measure $I_f$. The bath solution contained (mM): NaCl 140; KCl 5.4; $CaCl_2$ 1.8; $MgCl_2$ 1; D-glucose 10; Hepes 10 (pH adjusted to 7.4 with NaOH) and supplemented with (mM): NiCl 2; $BaCl_2$ 2; CdCl 0.2; 4-aminopyridine 1 to eliminate $Ca^{2+}$ current (T- and L-type), inward rectifier $K^+$ current, $I_{K1}$ and transient outward $K^+$ current, $I_{tO}$, respectively. KCl was increased to 25 mM to amplify $I_f$. Pipette solution contained (mM): K-glutamate 130; KCl 15; NaCl 5; MgATP 5; $MgCl_2$ 1; EGTA 5; $CaCl_2$ 1; Hepes 10 (pH adjusted to 7.2 with KOH). $I_f$ currents were evoked by 2 to 6 s hyperpolarizing steps to potentials ranging from −50 to −130 mV from a holding potential of −40 mV. A single-exponential fit of the current traces evoked at different potentials allowed derivation of time constants (τ) of current activation. The initial delay of the current was excluded from the fitting.

The reversal potential of $I_f$ was evaluated by tail currents recorded by 1.2 s 'tail' steps to membrane potentials ranging from −80 to 0 mV in 10 mV step intervals followed a 2 s conditioning potential step to −120 mV. The holding potential was set at −40 mV. The amplitudes of tail currents were then plotted against the test potentials. The current-voltage (I-V) relationship was fitted with a linear regression equation and the intersection on the x-axis was the reversal potential of $I_f$. The activation of $I_f$ was calculated by tail currents elicited by 3 s 'tail' pulses to −120 mV followed 5 s conditioning pulses from −130 mV to −60 mV in 10 mV increments every 10 s. The holding potential was −40 mV. The amplitudes of tail currents were then normalized to the maximal current and plotted against the conditional pulses. Activation data were fitted by a Boltzmann function.

As shown in FIG. 12, current traces of $I_f$ recorded from HL-5 cells. A, the voltage-clamp protocol. B, superimposed $I_f$ traces were recorded from a non-transfected HL-5 cell. C, superimposed $I_f$ traces were recorded from a HCN4-transfected HL-5 cell. D, current-voltage relationships of $I_f$ were plotted according to the values measured at the places of the vertical dotted lines for the control (○) and HCN4-transfected (●) HL-5 cells. Test pulses from −50 mV to −130 mV in 10 mV increments were applied. The holding potential was −40 mV and stimulation rate was 0.2 Hz. The arrows in panel A and B indicate the zero current level. The dotted horizontal line in panel D indicates the zero current level.

Figure 13:
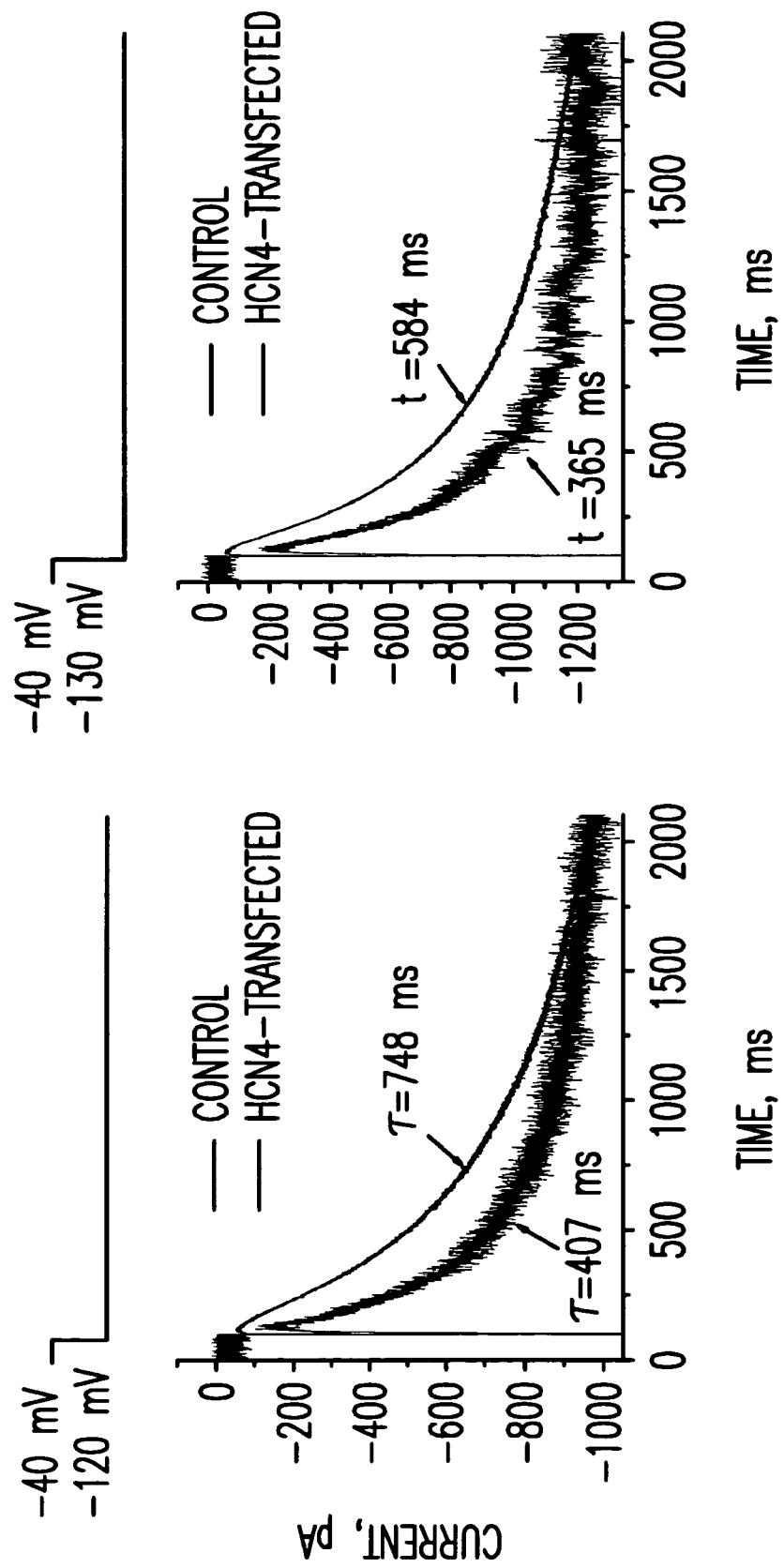
FIG. 13 depicts a comparison of activation kinetics of $I_f$ recorded in control and cardiac HL-5 cells transfected with rAAV-HCN4tr.
Figure 14:
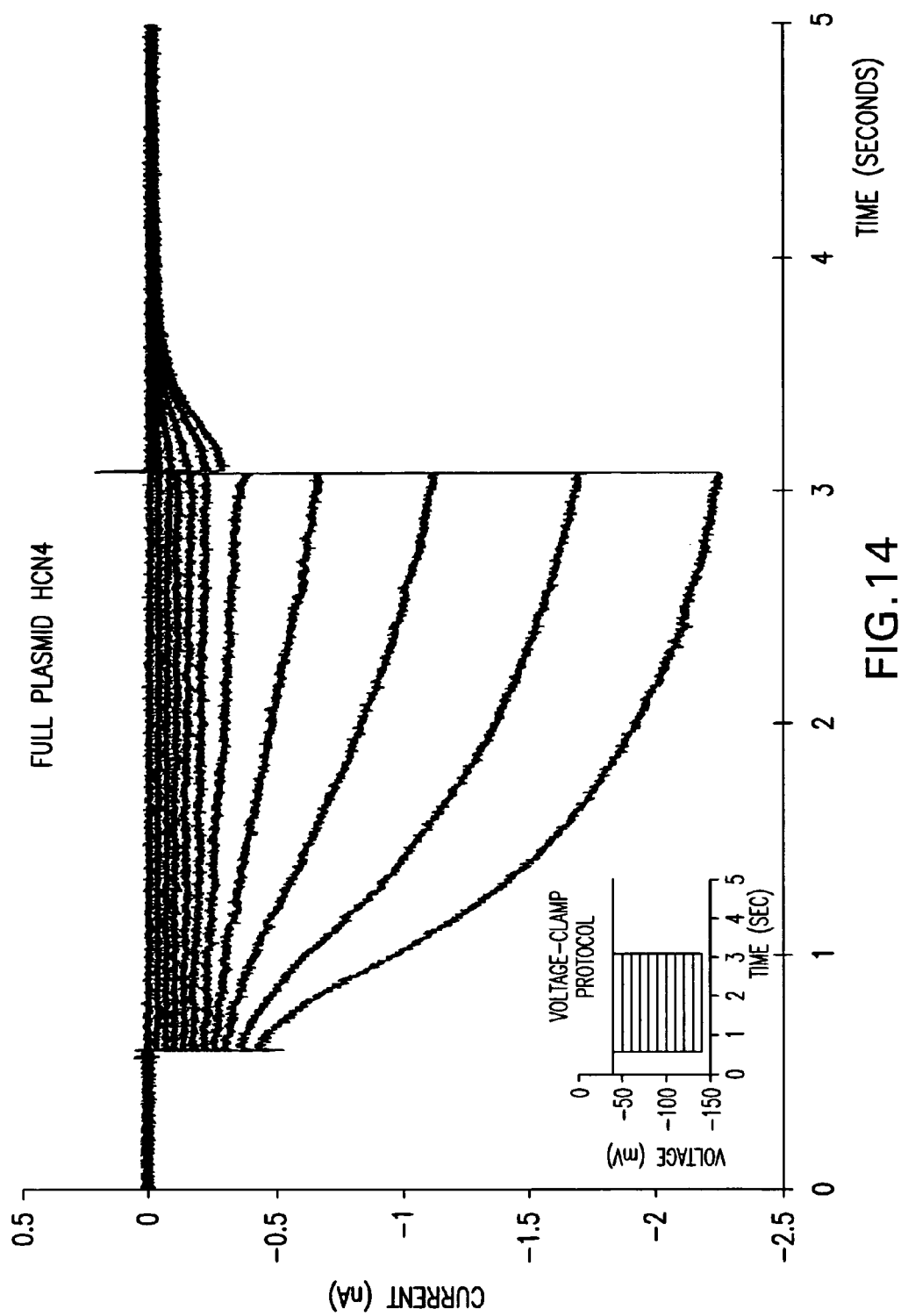
FIG. 14 depicts HCN4 whole cell voltage-clamp electrophysiology data recorded from HEK 293 cells transfected with full plasmid HCN4.
Figure 15:
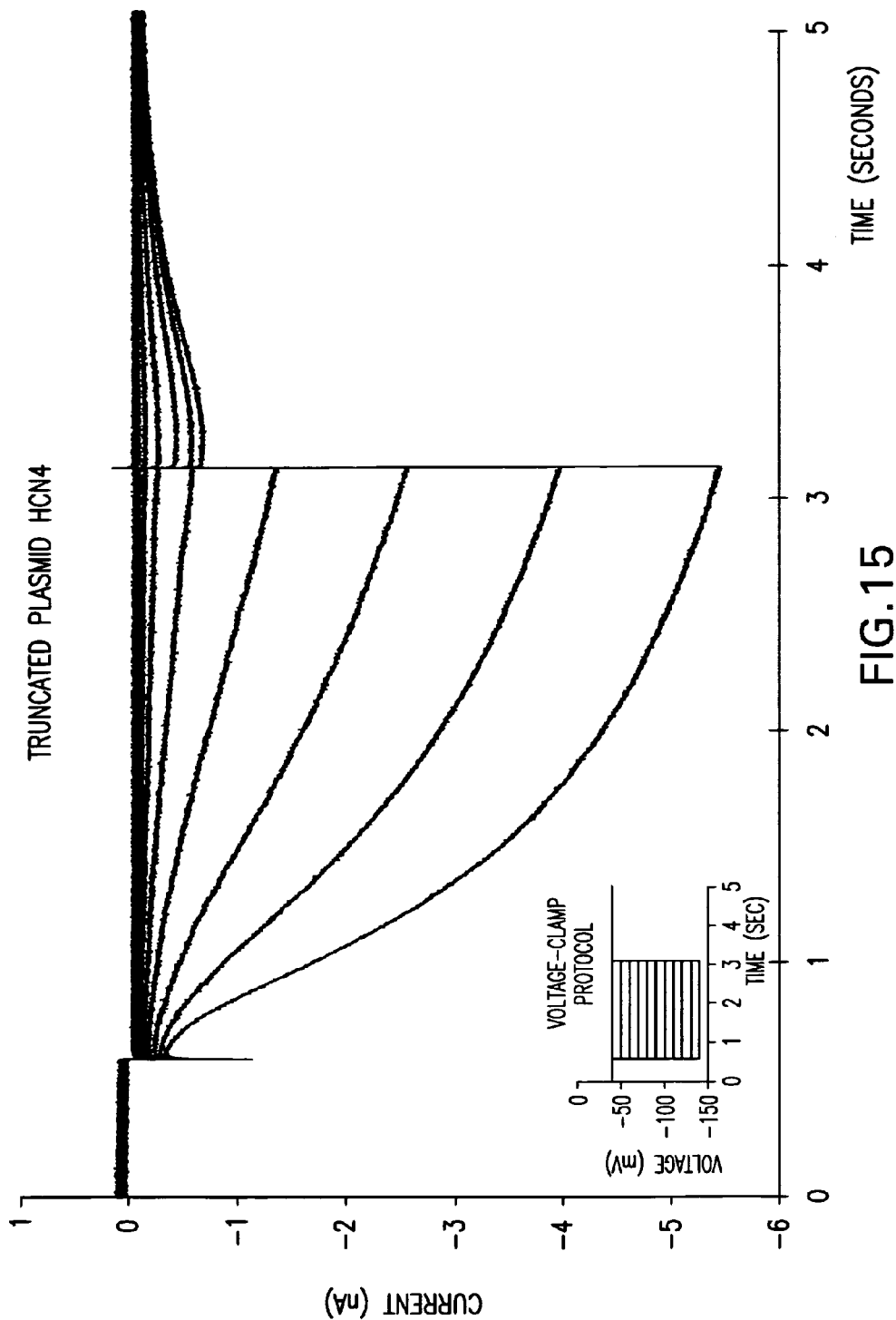
FIG. 15 depicts HCN4 whole cell voltage-clamp electrophysiology data recorded from HEK 293 cells transfected with truncated plasmid HCN4.
Figure 16:
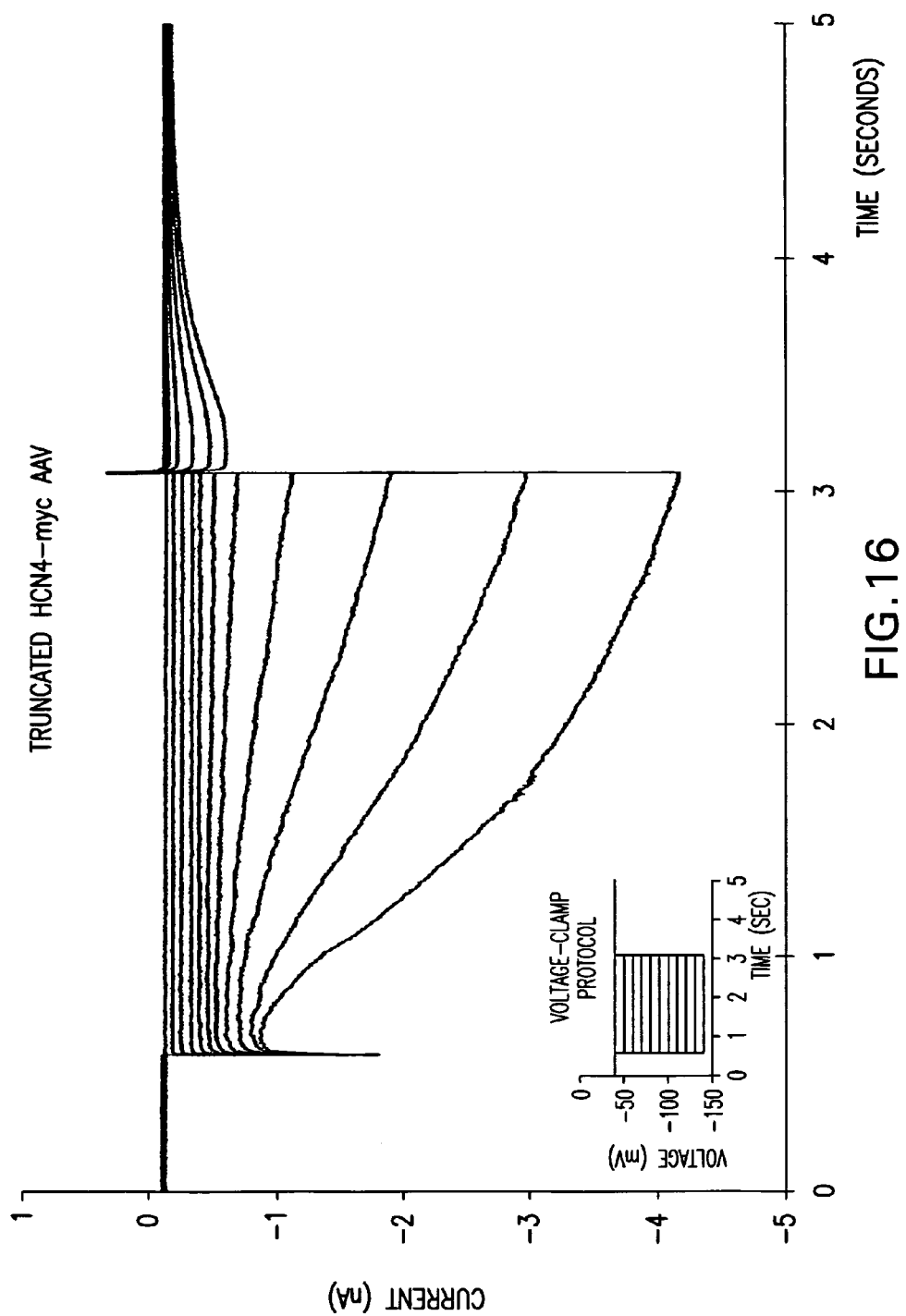
FIG. 16 depicts HCN4 whole cell voltage-clamp electrophysiology data recorded from HEK 293 cells transfected with truncated HCN4-myc AAV.
Figure 17:
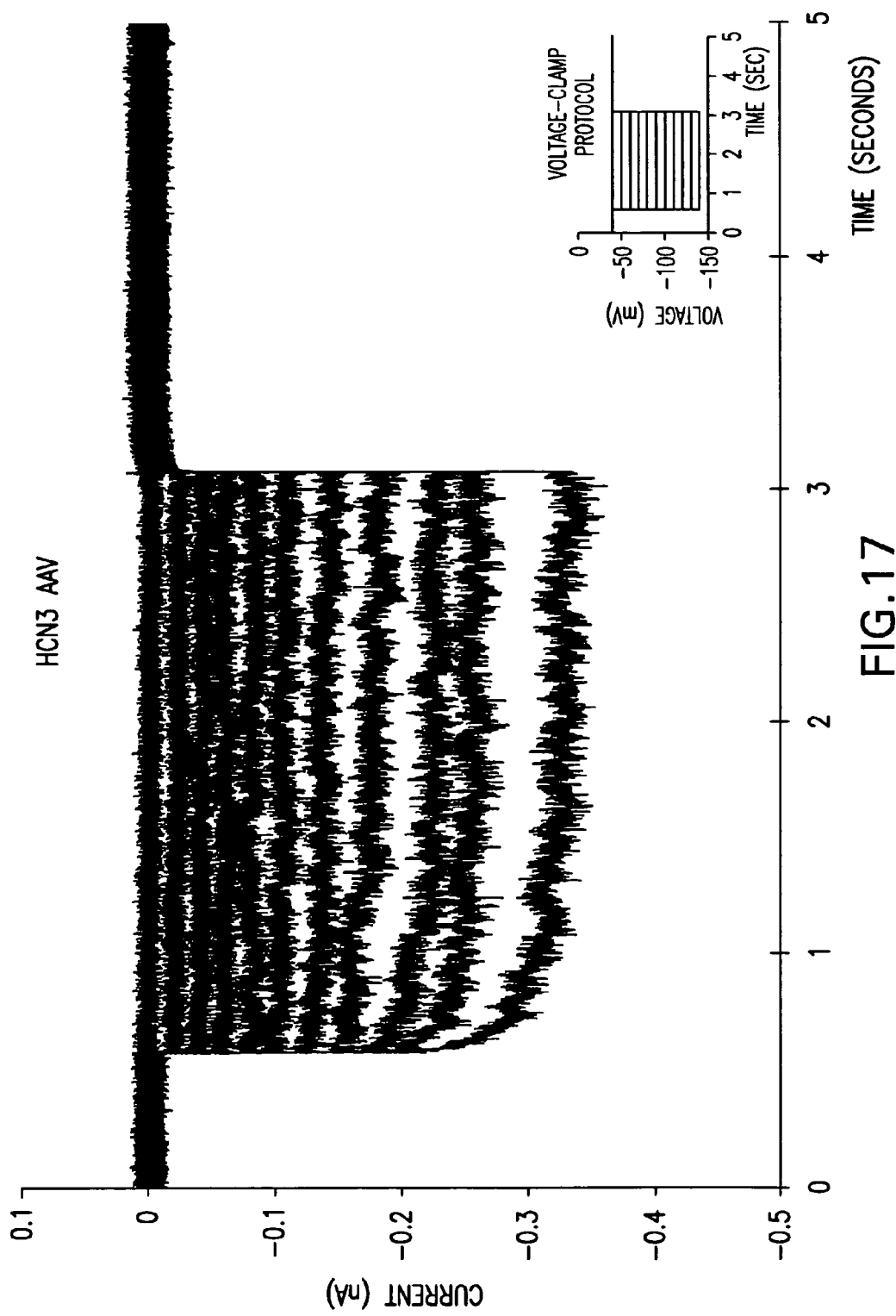
FIG. 17 depicts HCN3 whole voltage-clamp electrophysiology data recorded from HEK 293 cells transfected with HCN3 AAV.

FIG. 13 provides a comparison of activation kinetics of $I_f$ recorded in control and HCN4-transfected HL-5 cells (using rAAV-HCN4tr-cmyc). Superimposed current traces were elicited by test pulses (see the insets) from −40 mV to −120 mV (A) and from −40 mV to −130 mV (B) for the control (black trace) and HCN4-transfected (red trace) HL-5 cells. The maximal currents recorded from the control cell were normalized (by 5.4-fold for −120 mV and 5.1-fold for −130 mV) close to the maximal current of the HCN4-transfected cell. Time constants (τ) of activation of $I_f$ were fitted with the equation of single exponential decay.

Example II hHCN4-Channel Truncated Versus Full-Length hHCN4 Channel

Experiments were carried out to characterize the hHCN4-channel truncated 16 amino acids after the end of the cyclic nucleotide binding domain (CNBD). The truncated hHCN4 was compared to the full-length hHCN4 channel. See e.g., SEQ ID NOS. 4, 28 and 29. Electrophysiological experiments were carried out as described in Ludwig A., Zong X., Stieber J., Hullin R., Hofmann F. and Biel M., *Two Pacemaker Channels From Human Heart With Profoundly Different Activation Kinetics*, EMBO J 1999, 19 (9):2323-2329 and Stieber J., Thomer A., Much B., Schneider A., Biel M. and Hofmann F., *Molecular Basis For The Different Activation Kinetics of The Pacemaker Channels HCN2 and HCN4*, J Biol Chem 2003, 278 (36):33672-33680.

Using the FuGENE6 transfection reagent (Roche), HEK 293 cells were transiently transfected with one of the following cDNA constructs: (1) hHCN4 in the expression vector pcDNA3; (2) hHCN4 in the expression vector pIRES2-EGFP (bicistronic); (3) hHCN4, truncated 16 amino acids after the end of the CNBD, in the expression vector pcDNA3; or (4) hHCN4, truncated 16 amino acids after the end of the CNBD, in the expression vector pIRES2-EGFP (bicistronic).

HEK 293-cells were cultured in Quantum 286 complete medium (PAA Laboratories) on polylysated glass coverslips and kept at 37° C., 6% $CO_2$ until ready to use. Two to three days after transfection currents were recorded in the whole cell recording technique at a temperature of 22±1° C.

The bath solution contained the following constituents in mM: 120 NaCl, 20 KCl, 1 $MgCl_2$, 1.8 $CaCl_2$, 10 HEPES, 10 Glucose, pH adjusted to 7.4 with NaOH. The pipette solution contained (in mM): 10 NaCl, 30 KCl, 90 K-Asp, 1 $MgSO_4$, 5 EGTA, 10 HEPES, pH adjusted to 7.4 with KOH. Patch pipettes were pulled from borosilicate glass and had a resistance of 2-5 MΩ when filled with this pipette solution.

For determination of the effect of cAMP on the channels, 100 μM 8-Br-cAMP (Sigma) was added to the bath solution. Data were acquired using an Axopatch 200B amplifier and pClamp7-software (Axon Instruments) and low-pass filtered at 2 kHz with an 8-pole Bessel filter (LPBF-48DG, npi). Data were evaluated using the Origin 6.0 software (Microcal). All values are provided as mean ±SEM (standard error of the mean); 11-19 measurements (n) were evaluated per channel. Statistical differences were determined using Student's unpaired t-test; p-values <0.05 were considered significant.

To characterize the basic properties of the channels, the following was determined: (1) voltage-dependent activation curves with half-maximal activation ($V_{1/2}$); (2) voltage dependence of activation time constants T (activation kinetics) (both in the presence and absence of 100 µM cAMP); and (3) current—voltage relation with reversal potential ($E_{rev}$).

Figure 18:
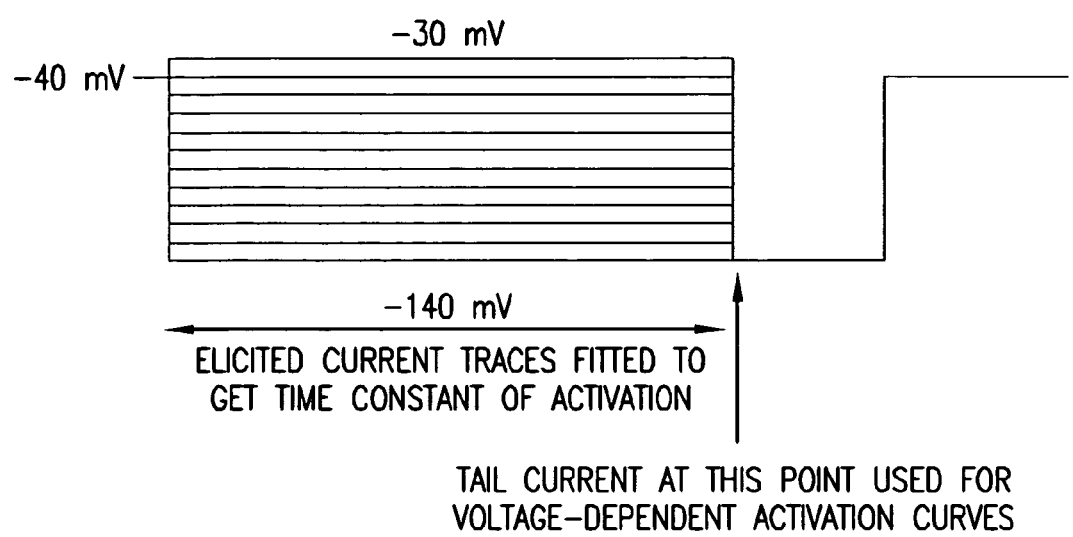
FIG. 18 depicts a pulse protocol for determining activation kinetics.

To determine activation curves and activation kinetics, a pulse protocol was used as shown in FIG. 18 where the holding potential was −40 mV and 10 mV-step pulses of 5 seconds duration from −140 mV to −30 mV, followed by a step to −140 mV for 2 seconds; 30 seconds between consecutive activation steps.

Figure 19:
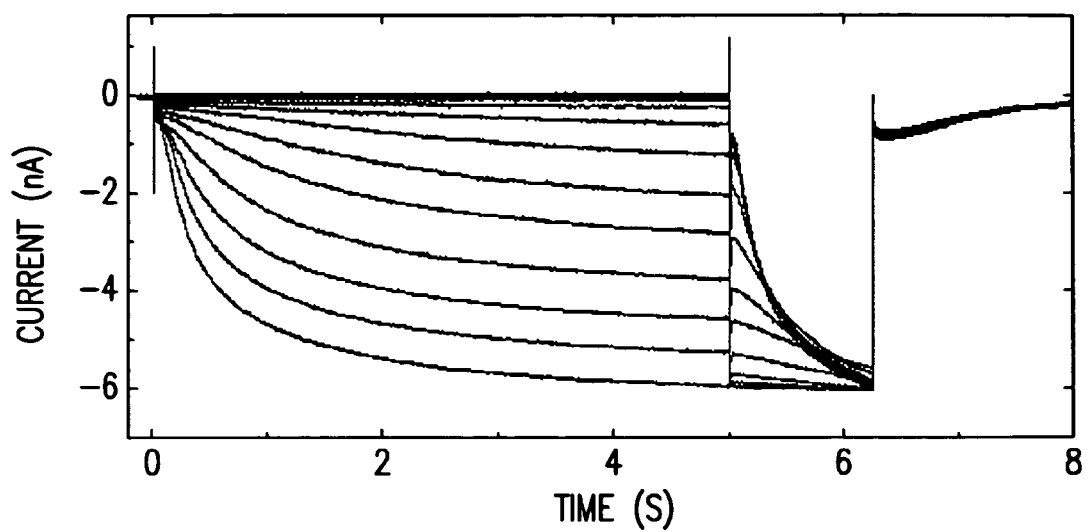
FIG. 19 depicts current recordings obtained using the protocol of FIG. 18 from truncated hHCN4 in pIRES2-EGFP.

With the protocol shown in FIG. 18, example current recordings were obtained from the truncated hHCN4 in pIRES2-EGFP and are shown in FIG. 19.

Time constants of activation ($\tau_{act}$) were obtained by fitting the current traces of the −140 to −90 mV steps after the initial lag with the sum of two exponential functions $$y = A_1 e^{(x/\tau 1)} + A_2 e^{(-x/\tau 2)},$$

where $\tau_1$ and $\tau_2$ are the fast and slow time constants of activation, respectively; $\tau_1$ is consequently referred to as $\tau_{act}$ since $A_1$ accounts for most of the current amplitude.

To obtain voltage-dependent steady-state activation curves, tail currents measured immediately after the final step to −140 mV were normalized by the maximal current ($I_{max}$) and plotted as a function of the preceding membrane potential. The curves were fitted with the Boltzmann function:

$$(I-I_{min})/(I_{man}-I_{min}) = (A_1-A_2)/(1+e^{(V-V1/2/K)}) + A_2,$$

where $I_{min}$ is an offset caused by a nonzero holding current and is not included in the current amplitude, V is the test potential, $V_{1/2}$ is the membrane potential for half-maximal activation, and K is the slope factor.

Figure 20:
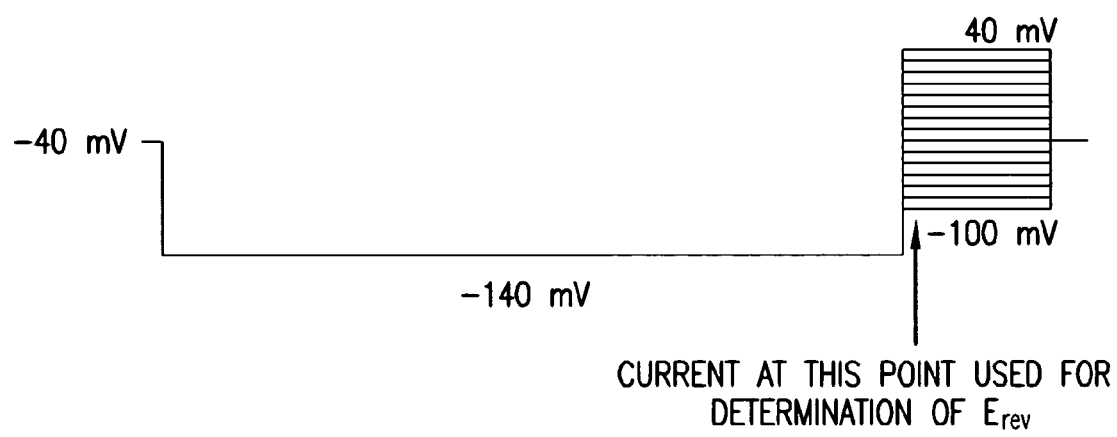
FIG. 20 depicts another pulse protocol for determining reversal potential.

To determine reversal potential, a pulse protocol was used as shown in FIG. 20 where the holding potential was −40 mV, the full activation of the channels held at −140 mV for 8 seconds, and 10 mV-step pulses to −100 mV to +40 mV and 30 seconds between consecutive activation steps.

Figure 21:
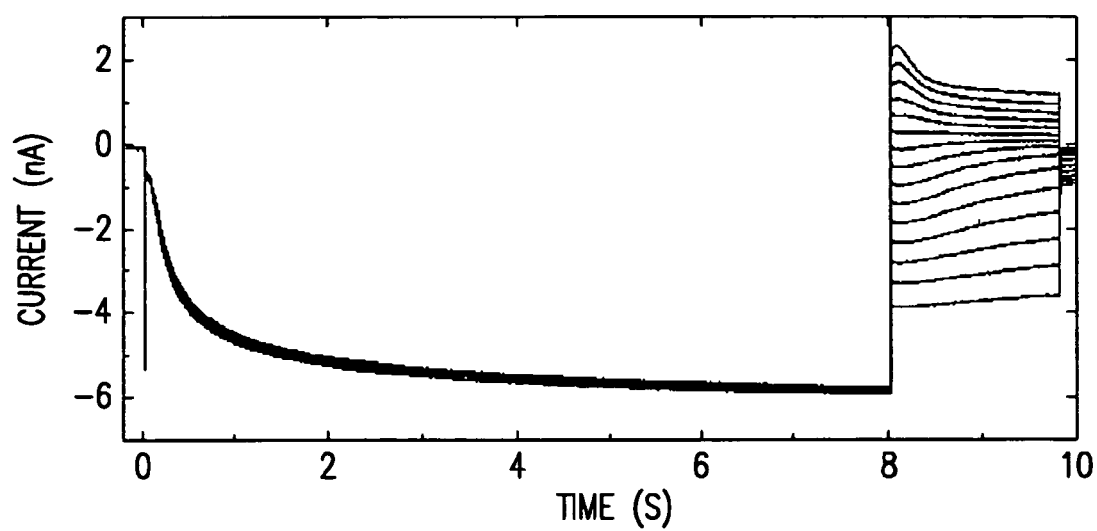
FIG. 21 depicts current recordings obtained using the protocol of FIG. 19 from truncated hHCN4 in pIRES2-EGFP.

With the protocol shown in FIG. 20, example current recording was obtained from the truncated hHCN4 in pIRES2-EGFP and is shown in FIG. 21.

To determine the reversal potential, the tail currents obtained immediately after the step to the test voltages were plotted against the voltage. Thus, $E_{rev}$ is the potential where the current is 0.

Figure 22:
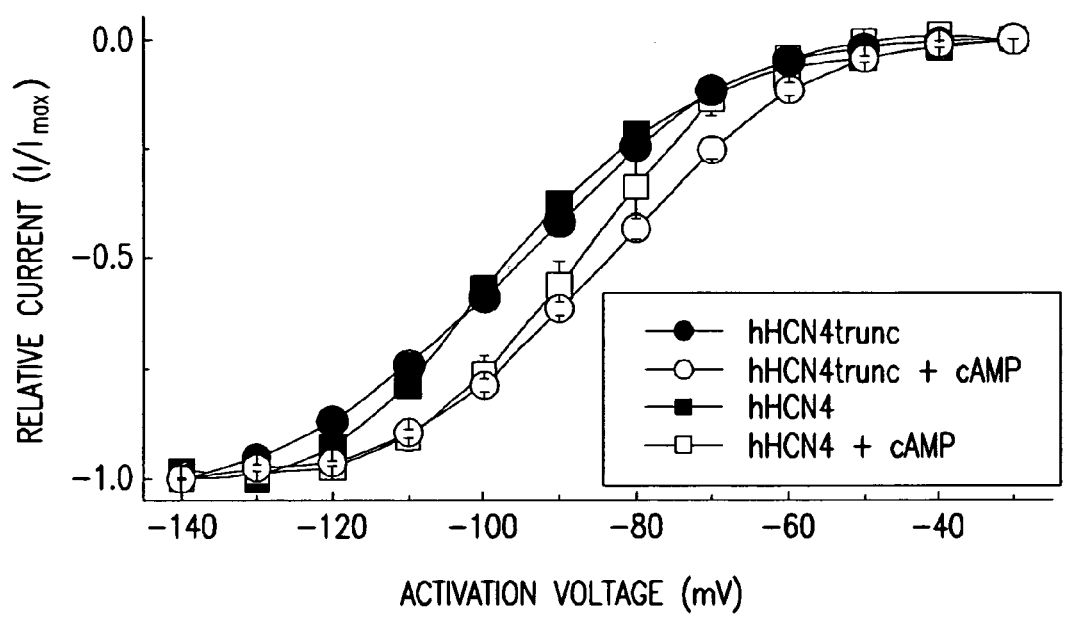
FIG. 22 depicts voltage-dependent activation curves for HCN4 and HCN4 truncated.

The voltage-dependent activation results are shown in FIG. 22. Generally, the truncated hHCN4-channel ("hHCN4trunc", black circles) is voltage-dependently activated like the full-length hHCN4 ("hHCN4", blue squares). $V_{1/2}$ (half-maximal activation or midpoint of activation) does not differ significantly between hHCN4 and hHCN4trunc, being about −96 mV for both. In addition, both channels are modulated by cAMP (open symbols) to the same extent, i.e. 100 µM cAMP induces a shift of the activation curve of ~13 mV towards more positive activation potentials. However, the slope factor k differs significantly, both between the two unmodulated and between the two cAMP-modulated curves. Thus, the slope of the full-length hHCN4 is slightly steeper than that of the truncated channel, implying that the truncated channel may be activated over a broader range of potentials. This is particularly important for the present invention because it suggests that the truncated human HCN4 channel is more responsive to cAMP at physiological voltages, thereby making it a more desirable gene candidate for a biological pacemaker therapy.

The following table gives the key parameters of the voltage-dependent activation:

|  | hHCN4, full length n = 19 | hHCN4, truncated n = 17 | Significance of difference (p-value) |
|---|---|---|---|
| unmodulated | | | |
| $V_{1/2}$ | −96.7 mV | −96.1 mV | p > 0.5 |
| SD | 4.01 | 3.44 | |
| SEM | | | |
| slope factor K | 11.0 | 14.3 | p < 0.001 |
| SD | 1.15 | 2.45 | |
| SEM | 0.31 | 0.71 | |
| cAMP - modulated | | | |
| $V_{1/2}$ | −83.7 mV | −83.2 mV | p > 0.5 |
| SD | 6.22 | 3.73 | |
| SEM | 2.54 | 1.18 | |
| slope factor K | 9.1 | 12.7 | p < 0.001 |
| SD | 1.33 | 2.11 | |
| SEM | 0.47 | 0.67 | |
| Shift induced by 100 µM 8-Br-cAMP: | | | |
| | +13.0 mV | +12.9 mV | |

Figure 23:
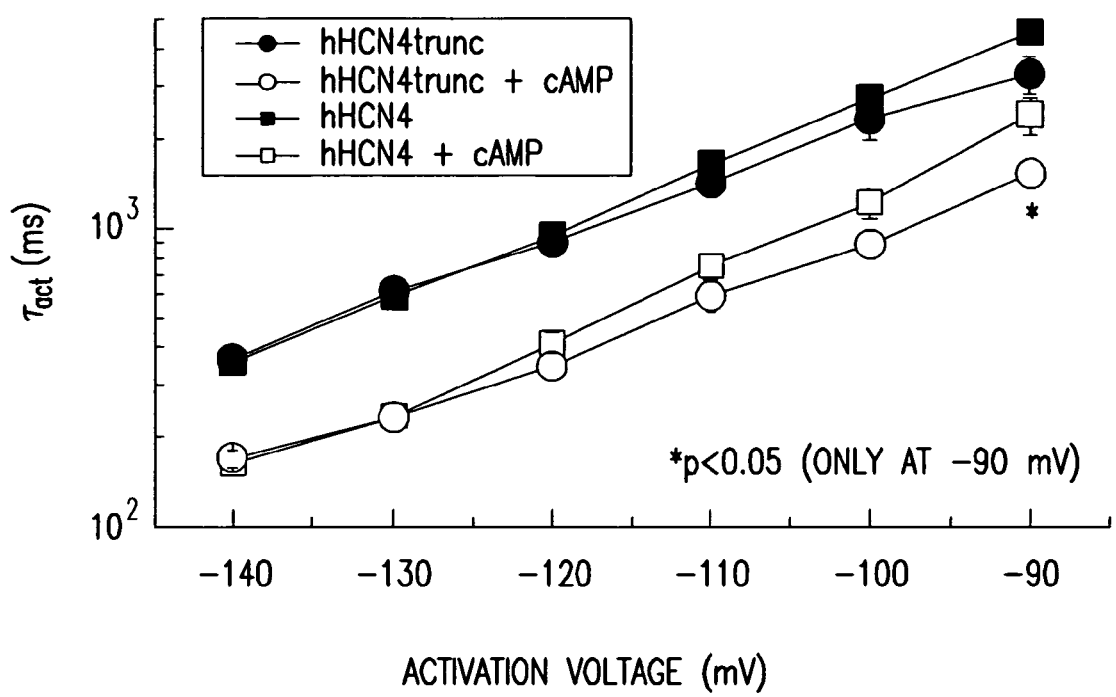
FIG. 23 depicts time constants of activation $\tau_{act}$ at certain activation voltages for HCN4 and HCN4 truncated.

Time constants of activation $\tau_{act}$ at activation voltages from −140 mV to −90 mV (note logarithmic scale of y-axis) are shown in FIG. 23. Both channels are modulated by cAMP, i.e., the time constants of activation over the whole range of potentials measured are shifted to smaller values. Therefore, the channels are 2- to 3-fold faster activated in the presence of cAMP. Comparing $\tau_{act}$ for each activation potential reveals that at potentials positive to −120 mV, the truncated hHCN4-channel tends to activate slightly faster than the full-length channel. This difference becomes significant only at −90 mV, both under nonmodulated and cAMP-modulated conditions.

Figure 24:
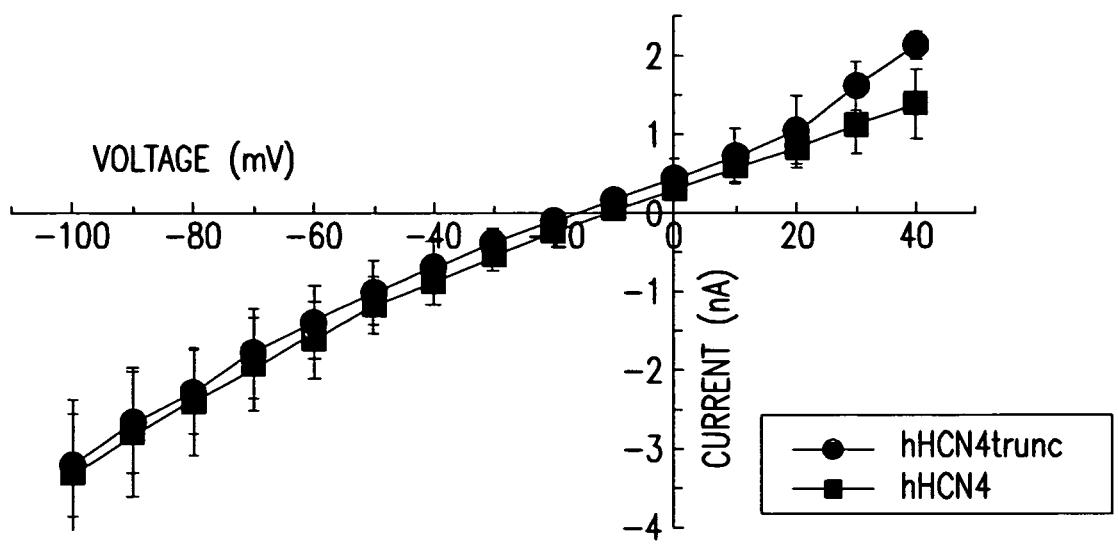
FIG. 24 depicts the reversal potential for both the full-length and truncated hHCN4.

As shown in FIG. 24, the reversal potential for both the full-length and truncated hHCN4 was determined in 20 mM extracellular potassium, without cAMP. It is −11.5 mV for hHCN4 and −16.2 mV for hHCN4trunc. The difference is not significant.

The human HCN4 channel, which is truncated 16 amino acids after the end of the cyclic nucleotide binding domain, can be well expressed in HEK 293-cells. The number of successfully transfected, i.e. HCN4-channel (current) and EGFP-(constructs in the pIRES2-EGFP-vector) expressing cells is approximately the same for all 4 tested constructs. Green-fluorescent cells can be well selected e.g. using excitation (filter) at λ=450-490 nm and detection at A=505-530 nm).

Both the full-length and truncated constructs display similar, HCN4-like currents. The currents are of comparable amplitude and can be modulated by cAMP to the same extent. cAMP shifts the activation curve of both channels about 13 mV to more positive activation potentials and accelerates the activation about 2-3-fold (voltage dependent).

There is a slight but significant difference between the full-length and truncated hHCN4-channels. The slope of the voltage-dependent activation curve is steeper for the full-length channel. This could mean that the truncated hHCN4 channel can be activated over a broader range of membrane potentials even though this is not reflected in the value of the midpoint of activation $V_{1/2}$ which is about −96 mV for both channels.

In addition to this difference in the voltage-dependent activation, there is a tendency for the truncated hHCN4-channel towards faster time constants of activation. This difference, however, is only significant at an activation potential of −90 mV.

All patents and publications referenced herein are hereby incorporated by reference. Referenced web sites are not incorporated by reference. It will be understood that certain of the above-described structures, functions and operations of the above-described preferred embodiments are not necessary to practice the present invention and are included in the description simply for completeness of an example embodiment or embodiments. In addition, it will be understood that specific structures, functions and operations set forth in the above-referenced patents and publications can be practiced in conjunction with the present invention, but they are not essential to its practice. It is therefore to be understood that within the scope of the claims, the invention may be practiced otherwise than as specifically described without actually departing from the spirit and scope of the present invention.

What is claimed is:

1. A nucleic acid construct comprising a heterologous regulatory sequence operably linked to the nucleotide sequence as set forth in SEQ ID NO: 28 encoding a human hyperpolarization-activated cyclic nucleotide-gated 4 (HCN4) truncated protein, wherein the human HCN4 is truncated 16 amino acids after the end of the coding sequence of the cyclic nucleotide binding domain (CNBD), and wherein expression of the human HCN4 truncated polynucleotide in an isolated cell results in a channel responsive to cAMP over a broader range of potentials than wild-type human HCN4.

2. An isolated purified cell comprising the construct of claim 1, wherein expression of the human HCN4 truncated polynucleotide in the cell results in a channel responsive to cAMP over a broader range of potentials than wild-type human HCN4.

* * * * *

SEQUENCE LISTING

```
<160> NUMBER OF SEQ ID NOS: 29

<210> SEQ ID NO 1
<211> LENGTH: 2673
<212> TYPE: DNA
<213> ORGANISM: Homo Sapiens
<220> FEATURE:
<221> NAME/KEY: gene
<222> LOCATION: (1)..(2673)
<223> OTHER INFORMATION: hyperpolarization activated cyclic
      nucleotide-gated potassium channel 1 (HCN1) (Accession: NM 021072)

<400> SEQUENCE: 1
atggaaggag gcggcaagcc caactcttcg tctaacagcc gggacgatgg caacagcgtc      60
ttccccgcca aggcgtccgc gacgggcgcg gggccggccg cggccgagaa gcgcctgggc     120
accccgccgg ggggcggcgg ggccggcgcg aaggagcacg gcaactccgt gtgcttcaag     180
gtggacggcg gtggcggcgg tggcggcggc ggcggcggcg gcgaggagcc ggcggggggc     240
ttcgaagacg ccgaggggcc ccggcggcag tacggcttca tgcagaggca gttcacctcc     300
atgctgcagc ccggggtcaa caaattctcc ctccgcatgt ttgggagcca gaaggcggtg     360
gaaaaggagc aggaaagggt taaaactgca ggcttctgga ttatccaccc ttacagtgat     420
ttcaggtttt actgggattt aataatgctt ataatgatgg ttggaaatct agtcatcata     480
ccagttggaa tcacattctt tacagagcaa acaacaacac catggattat tttcaatgtg     540
gcatcagata cagttttcct attggacctg atcatgaatt ttaggactgg gactgtcaat     600
gaagacagtt ctgaaatcat cctggacccc aaagtgatca agatgaatta tttaaaaagc     660
tggtctgtgg ttgacttcat ctcatccatc ccagtggatt atatctttct tattgtagaa     720
aaaggaatgg attctgaagt ttacaagaca gccagggcac ttcgcattgt gaggtttaca     780
aaaattctca gtctcttgcg tttattacga ctttcaaggt taattagata catacatcaa     840
tgggaagaga tattccacat gacatatgat ctcgccagtg cagtggtgag aatttttaat     900
ctcatcggca tgatgctgct cctgtgccac tgggatggtt gtcttcagtt cttagtacca     960
ctactgcagg acttcccacc agattgctgg gtgtctttaa atgaaatggt taatgattct    1020
tggggaaagc agtattcata cgcactcttc aaagctatga gtcacatgct gtgcattggg    1080
tatggagccc aagcccagt cagcatgtct gacctctgga ttaccatgct gagcatgatc    1140
gtcgggccca cctgctatgc catgtttgtc ggccatgcca ccgctttaat ccagtctctg    1200
gattcttcga ggcggcagta tcaagagaag tataagcaag tggaacaata catgtcattc    1260
cataagttac cagctgatat gcgtcagaag atacatgatt actatgaaca cagataccaa    1320
ggcaaaatct ttgatgagga aaatattctc aatgaactca atgatcctct gagagggggag    1380 atagtcaact tcaactgtcg gaaactggtg gctacaatgc ctttatttgc taatgcggat    1440
```

-continued

| | |
|---|---|
| cctaattttg tgactgccat gctgagcaag ttgagatttg aggtgtttca acctggagat | 1500 |
| tatatcgtac gagaaggagc cgtgggtaaa aaaatgtatt tcattcaaca cggtgttgct | 1560 |
| ggtgtcatta caaaatccag taaagaaatg aagctgacag atggctctta ctttggagag | 1620 |
| atttgcctgc tgaccaaagg acgtcgtact gccagtgttc gagctgatac atattgtcgt | 1680 |
| ctttactcac tttccgtgga caatttcaac gaggtcccgg aggaatatcc aatgatgagg | 1740 |
| agagcctttg agacagttgc cattgaccga ctagatcgaa taggaaagaa aaattcaatt | 1800 |
| cttctgcaaa agttccagaa ggatctgaac actggtgttt caacaatca ggagaacgaa | 1860 |
| atcctcaagc agattgtgaa acatgacagg gagatggtgc aggcaatcgc tcccatcaat | 1920 |
| tatcctcaaa tgacaaccct gaattccgca tcgtctacta cgaccccgac ctcccgcatg | 1980 |
| aggacacaat ctccaccggt gtacacagcg accagcctgt ctcacagcaa cctgcactcc | 2040 |
| cccagtccca gcacacagac cccccagcca tcagccatcc tgtcaccctg ctcctacacc | 2100 |
| accgcggtct gcagccctcc tgtacagagc cctctggccg ctcgaacttt ccactatgcc | 2160 |
| tcccccaccg cctcccagct gtcactcatg caacagcagc cgcagcagca ggtacagcag | 2220 |
| tcccagccgc cgcagactca gccacagcag ccgtccccgc agccacagac acctggcagc | 2280 |
| tccacgccga aaaatgaagt gcacaagagc acgcaggcgc ttcacaacac caacctgacc | 2340 |
| cgggaagtca ggccactctc cgcctcgcag ccctcgctgc ccatgaggt gcccactctg | 2400 |
| atttccagac ctcatcccac tgtgggcgag tccctggcct ccatcccctca acccgtgacg | 2460 |
| gcggtccccg gaacgggcct tcaggcaggg ggcaggagca ctgtcccgca gcgcgtcacc | 2520 |
| ctcttccgac agatgtcgtc gggagccatc ccccccgaacc gaggagtccc tccagcaccc | 2580 |
| cctccaccag cagctgctct tccaagagaa tcttcctcag tcttaaacac agacccagac | 2640 |
| gcagaaaagc cacgatttgc ttcaaattta tga | 2673 |

<210> SEQ ID NO 2
<211> LENGTH: 2670
<212> TYPE: DNA
<213> ORGANISM: Homo Sapiens
<220> FEATURE:
<221> NAME/KEY: gene
<222> LOCATION: (1)..(2670)
<223> OTHER INFORMATION: Hyperpolarization Activated Cyclic
       Nucleotide-Gated Potassium Channel 2 (HCN2) (Accession: NM_001194)

<400> SEQUENCE: 2

| | |
|---|---|
| atggacgcgc gcggggcgg cgggcggccc gggagagcc cgggcgcgac cccgcgccg | 60 |
| gggccgccgc cgccgccgcc gcccgcgccc ccccaacagc agccgccgcc gccgccgccg | 120 |
| cccgcgcccc cccggggccc cgggcccgcg cccccccagc accgcccccg ggccgaggcg | 180 |
| ttgcccccgg aggcggcgga tgagggcggc ccgcggggcc ggctccgcag ccgcgacagc | 240 |
| tcgtgcggcc gccccggcac cccgggcgcg gcgagcacgg ccaagggcag cccgaacggc | 300 |
| gagtgcgggc gcggcgagcc gcagtgcagc cccgcggggc ccgagggccc ggcgcggggg | 360 |
| cccaaggtgt cgttctcgtg ccgcggggcg gcctcgggc ccgcgccggg gcggggccg | 420 |
| gcggaggagg cgggcagcga ggaggcggc ccggcggggg agccgcgcgg cagccaggcc | 480 |
| agcttcatgc agcgccagtt cggcgcgctc ctgcagccgg gcgtcaacaa gttctcgctg | 540 |
| cggatgttcg gcagccagaa ggccgtggag cgcgagcagg agcgcgtcaa gtcggcgggg | 600 |
| gcctggatca tccacccgta cagcgacttc aggttctact gggacttcac catgctgctg | 660 |
| ttcatggtgg gaaacctcat catcatccca gtgggcatca ccttcttcaa ggatgagacc | 720 |

```
actgccccgt ggatcgtgtt caacgtggtc tcggacacct tcttcctcat ggacctggtg    780
ttgaacttcc gcaccggcat tgtgatcgag gacaacacgg agatcatcct ggaccccgag    840
aagatcaaga agaagtatct gcgcacgtgg ttcgtggtgg acttcgtgtc ctccatcccc    900
gtggactaca tcttccttat tgtggagaag ggcattgact ccgaggtcta caagacggca    960
cgcgccctgc gcatcgtgcg cttcaccaag atcctcagcc tcctgcggct gctgcgcctc   1020
tcacgcctga tccgctacat ccatcagtgg aggagatct tccacatgac ctatgacctg   1080
gccagcgcgg tgatgaggat ctgcaatctc atcagcatga tgctgctgct ctgccactgg   1140
gacggctgcc tgcagttcct ggtgcctatg ctgcaggact cccgcgcaa ctgctgggtg   1200 tccatcaatg gcatggtgaa ccactcgtgg agtgaactgt actccttcgc actcttcaag   1260
gccatgagcc acatgctgtg catcgggtac ggccggcagg cgcccgagag catgacggac   1320
atctggctga ccatgctcag catgattgtg ggtgccacct gctacgccat gttcatcggc   1380
cacgccactg ccctcatcca gtcgctggac tcctcgcggc gccagtacca ggagaagtac   1440
aagcaggtgg agcagtacat gtccttccac aagctgccag ctgacttccg ccagaagatc   1500
cacgactact atgagcaccg ttaccagggc aagatgtttg acgaggacag catcctgggc   1560
gagctcaacg ggcccctgcg ggaggagatc gtcaacttca actgccggaa gctggtggcc   1620
tccatgccgc tgttcgccaa cgccgacccc aacttcgtca cggccatgct gaccaagctc   1680
aagttcgagg tcttccagcc gggtgactac atcatccgcg aaggcaccat cgggaagaag   1740
atgtacttca tccagcacgg cgtggtcagc gtgctcacta agggcaacaa ggagatgaag   1800
ctgtccgatg gctcctactt cggggagatc tgcctgctca cccggggccg ccgcacggcg   1860
agcgtgcggg ccgacaccta ctgccgcctc tattcgctga gcgtggacaa cttcaacgag   1920
gtgctggagg agtaccccat gatgcggcgc gccttcgaga cggtggccat cgaccgcctg   1980
gaccgcatcg gcaagaagaa ttccatcctc ctgcacaagg tgcagcatga cctcaactcg   2040
ggcgtattca acaaccagga gaacgccatc atccaggaga tcgtcaagta cgaccgcgag   2100
atggtgcagc aggccgagct gggtcagcgc gtgggcctct cccgccgcc gccgccgccg   2160 ccgcaggtca cctcggccat cgccacgctg cagcaggcgg cggccatgag cttctgcccg   2220
caggtggcgc ggccgctcgt ggggccgctg gcgctcggct cgccgcgcct cgtgcgccgc   2280
ccgcccccgg ggcccgcacc tgccgccgcc tcacccgggc cccgccccc cgccagcccc   2340 ccgggcgcgc ccgccagccc ccgggcaccg cggacctcgc cctacggcgg cctgcccgcc   2400 gcccccttg ctgggcccgc cctgcccgcg cgccgcctga ccgcgcgtc gcgcccactg   2460 tccgcctcgc agccctcgct gcctcacggc gcccccggcc ccgcggcctc cacacgcccg   2520
gccagcagct ccacaccgcg cttgaggccc acgcccgctg cccgggccgc cgcgcccagc   2580
ccggaccgca gggactcggc ctcacccggc cgccggcg gcctggaccc ccaggactcc   2640
gcgcgctcgc gcctctcgtc caacttgtga                                   2670
```

<210> SEQ ID NO 3
<211> LENGTH: 2325
<212> TYPE: DNA
<213> ORGANISM: Homo Sapiens
<220> FEATURE:
<221> NAME/KEY: gene
<222> LOCATION: (1)..(2325)
<223> OTHER INFORMATION: Hyperpolarization Activated Cyclic
      Nucleotide-Gated Potassium Channel 3 (HCN3) (Accession: NM_020897)

```
<400> SEQUENCE: 3
atggaggcag agcagcggcc ggcggcgggg gccagcgaag gggcgacccc tggactggag    60
gcggtgcctc ccgttgctcc cccgcctgcg accgcggcct caggtccgat ccccaaatct   120
gggcctgagc ctaagaggag gcaccttggg acgctgctcc agcctacggt caacaagttc   180
tcccttcggg tgttcggcag ccacaaagca gtggaaatcg agcaggagcg ggtgaagtca   240
gcggggcct ggatcatcca ccctacagc gacttccggt tttactggga cctgatcatg    300
ctgctgctga tggtggggaa cctcatcgtc ctgcctgtgg gcatcacctt cttcaaggag   360
gagaactccc cgccttggat cgtcttcaac gtattgtctg atactttctt cctactggat   420
ctggtgctca acttccgaac gggcatcgtg gtggaggagg tgctgagat cctgctggca    480
ccgcgggcca tccgcacgcg ctacctgcgc acctggttcc tggttgacct catctcttct   540
atccctgtgg attacatctt cctagtggtg gagctggagc cacggttgga cgctgaggtc   600
tacaaaacgg cacgggccct acgcatcgtt cgcttcacca agatcctaag cctgctgagg   660
ctgctccgcc tctcccgcct catccgctac atacaccagt gggaggagat ctttcacatg   720
acctatgacc tggccagtgc tgtggttcgc atcttcaacc tcattgggat gatgctgctg   780
ctatgtcact gggatggctg tctgcagttc ctggtgccca tgctgcagga cttccctccc   840
gactgctggg tctccatcaa ccacatggtg aaccactcgt ggggccgcca gtattcccat   900
gccctgttca aggccatgag ccacatgctg tgcattggct atgggcagca ggcacctgta   960
ggcatgcccg acgtctggct caccatgctc agcatgatcg taggtgccac atgctacgcc  1020
atgttcatcg ccatgccac ggcactcatc cagtccctgg actcttcccg cgtcagtac   1080
caggagaagt acaagcaggt ggagcagtac atgtccttcc acaagctgcc agcagacacg  1140
cggcagcgca tccacgagta ctatgagcac cgctaccagg gcaagatgtt cgatgaggaa  1200
agcatcctgg gcgagctgag cgagccgctt cgcgaggaga tcattaactt cacctgtcgg  1260
ggcctggtgg cccacatgcc gctgtttgcc catgccgacc cagcttcgt cactgcagtt   1320
ctcaccaagc tgcgctttga ggtcttccag ccggggggatc tcgtggtgcg tgagggctcc  1380
gtggggagga agatgtactt catccagcat gggctgctca gtgtgctggc ccgcggcgcc  1440
cgggacacac gcctcaccga tggatcctac tttggggaga tctgcctgct aactagggc   1500
cggcgcacag ccagtgttcg ggctgacacc tactgccgcc tttactcact cagcgtggac  1560
catttcaatg ctgtgcttga ggagttcccc atgatgcgcc gggcctttga gactgtggcc  1620
atggatcggc tgctccgcat cggcaagaag aattccatac tgcagcggaa gcgctccgag  1680
ccaagtccag gcagcagtgg tggcatcatg gagcagcact tggtgcaaca tgacagagac  1740
atggctcggg gtgttcgggg tcgggccccg agcacaggag ctcagcttag tggaaagcca  1800
gtactgtggg agccactggt acatgcgccc cttcaggcag ctgctgtgac ctccaatgtg  1860
gccattgccc tgactcatca gcggggcct ctgcccctct ccctgactc tccagccacc   1920
ctccttgctc gctctgcttg gcgctcagca ggctctccag cttccccgct ggtgcccgtc  1980
cgagctggcc catgggcatc cacctcccgc ctgcccgccc cacctgcccg aaccctgcac  2040
gccagcctat cccgggcagg gcgctcccag gtctccctgc tgggtccccc tccaggagga  2100
ggtggacggc ggctaggacc tcggggccgc ccactctcag cctcccaacc ctctctgcct  2160
cagcgggcaa caggcgatgg ctctcctggg cgtaagggat caggaagtga gcggctgcct  2220
ccctcagggc tcctggccaa acctccaagg acagcccagc cccccaggcc accagtgcct  2280
gagccagcca caccccgggg tctccagctt tctgccaaca tgtaa                  2325
```

<210> SEQ ID NO 4
<211> LENGTH: 3612
<212> TYPE: DNA
<213> ORGANISM: Homo Sapiens
<220> FEATURE:
<221> NAME/KEY: gene
<222> LOCATION: (1)..(3612)
<223> OTHER INFORMATION: Hyperpolarization Activated Cyclic
      Nucleotide-Gated Potassium Channel 4 (HCN4) (Accession: NM_005477)

<400> SEQUENCE: 4

| | | | | | | |
|---|---|---|---|---|---|---|
| atggacaagc | tgccgccgtc | catgcgcaag | cggctctaca | gcctcccgca | gcaggtgggg | 60 |
| gccaaggcgt | ggatcatgga | cgaggaagag | gacgccgagg | aggaggggc | cggggggccgc | 120 |
| caagaccccca | gccgcaggag | catccggctg | cggccactgc | cctcgccctc | ccctcggcg | 180 |
| gccgcgggtg | gcacggagtc | ccggagctcg | gccctcgggg | cagcggacag | cgaagggccg | 240 |
| gcccgcggcg | cgggcaagtc | cagcacgaac | ggcgactgca | ggcgcttccg | cgggagcctg | 300 |
| gcctcgctgg | gcagccgggg | cggcggcagc | ggcggcacgg | ggagcggcag | cagtcacgga | 360 |
| cacctgcatg | actccgcgga | ggagcggcgg | ctcatcgccg | agggcgacgc | gtccccggc | 420 |
| gaggacagga | cgccccagg | cctggcggcc | gagcccgagc | gccccggcgc | ctcggcgcag | 480 |
| cccgcagcct | cgccgccgcc | gccccagcag | ccaccgcagc | cggcctccgc | ctcctgcgag | 540 |
| cagccctcgg | tggacaccgc | tatcaaagtg | agggaggcg | cggctgccgg | cgaccagatc | 600 |
| ctcccggagg | ccgaggtgcg | cctgggccag | gccggcttca | tgcagcgcca | gttcggggcc | 660 |
| atgctccaac | ccggggtcaa | caaattctcc | ctaaggatgt | tcggcagcca | gaaagccgtg | 720 |
| gagcgcgaac | aggagagggt | caagtcggcc | ggattttgga | ttatccaccc | ctacagtgac | 780 |
| ttcagatttt | actgggacct | gaccatgctg | ctgctgatgg | tgggaaacct | gattatcatt | 840 |
| cctgtgggca | tcaccttctt | caaggatgag | aacaccacac | cctggattgt | cttcaatgtg | 900 |
| gtgtcagaca | cattcttcct | catcgacttg | gtcctcaact | tccgcacagg | gatcgtggtg | 960 |
| gaggacaaca | cagagatcat | cctggacccg | cagcggatta | aaatgaagta | cctgaaaagc | 1020 |
| tggttcatgg | tagatttcat | ttcctccatc | ccgtgggact | acatcttcct | cattgtggag | 1080 |
| acacgcatcg | actcggaggt | ctacaagact | gcccgggccc | tgcgcattgt | ccgcttcacg | 1140 |
| aagatcctca | gcctcttacg | cctgttacgc | ctctcccgcc | tcattcgata | tattcaccag | 1200 |
| tgggaagaga | tcttccacat | gacctacgac | ctggccagcg | ccgtggtgcg | catcgtgaac | 1260 |
| ctcatcggca | tgatgctcct | gctctgccac | tgggacggct | gctgcagtt | cctggtaccc | 1320 |
| atgctacagg | acttccctga | cgactgctgg | gtgtccatca | caacatggt | gaacaactcc | 1380 |
| tgggggaagc | agtactccta | cgcgctcttc | aaggccatga | ccacatgct | gtgcatcggc | 1440 |
| tacgggcggc | aggcgcccgt | gggcatgtcc | gacgtctggc | tcaccatgct | cagcatgatc | 1500 |
| gtgggtgcca | cctgctacgc | catgttcatt | ggccacgcca | tgccctcat | ccagtccctg | 1560 |
| gactcctccc | ggcgccagta | ccaggaaaag | tacaagcagg | tggagcagta | catgtccttt | 1620 |
| cacaagctcc | cgccgacac | ccggcagcgc | atccacgact | actacgagca | ccgctaccag | 1680 |
| ggcaagatgt | tcgacgagga | gagcatcctg | ggcgagctaa | gcgagcccct | gcgggaggag | 1740 |
| atcatcaact | taactgtcg | gaagctggtg | gcctccatgc | cactgtttgc | caatgcggac | 1800 |
| cccaacttcg | tgacgtccat | gctgaccaag | ctgcgtttcg | aggtcttcca | gcctgggac | 1860 |
| tacatcatcc | gggaaggcac | cattggcaag | aagatgtact | tcatccagca | tggcgtggtc | 1920 |
| agcgtgctca | ccaagggcaa | caaggagacc | aagctggccg | acggctccta | ctttggagag | 1980 |

| | |
|---|---|
| atctgcctgc tgacccgggg ccggcgcaca gccagcgtga gggccgacac ctactgccgc | 2040 |
| ctctactcgc tgagcgtgga caacttcaat gaggtgctgg aggagtaccc catgatgcga | 2100 |
| agggccttcg agaccgtggc gctggaccgc ctggaccgca ttggcaagaa gaactccatc | 2160 |
| ctcctccaca aagtccagca cgacctcaac tccggcgtct tcaactacca ggagaatgag | 2220 |
| atcatccagc agattgtgca gcatgaccgg gagatggccc actgcgcgca ccgcgtccag | 2280 |
| gctgctgcct ctgccacccc aacccccacg cccgtcatct ggaccccgct gatccaggca | 2340 |
| ccactgcagg ctgccgctgc caccacttct gtggccatag ccctcaccca ccaccctcgc | 2400 |
| ctgcctgctg ccatcttccg ccctcccccca ggatctgggc tgggcaacct cggtgccggg | 2460 |
| cagacgccaa ggcacctgaa acggctgcag tccctgatcc cttctgcgct gggctccgcc | 2520 |
| tcgcccgcca gcagcccgtc ccaggtggac acaccgtctt catcctcctt ccacatccaa | 2580 |
| cagctggctg gattctctgc ccccgctgga ctgagcccac tcctgccctc atccagctcc | 2640 |
| tccccacccc ccgggggcctg tggctccccc tcggctccca ccatcagc tggcgtagcc | 2700 |
| gccaccacca tagccgggtt tggccacttc acaaggcgc tgggtggctc cctgtcctcc | 2760 |
| tccgactctc ccctgctcac cccgctgcag ccaggcgccc gctccccgca ggctgcccag | 2820 |
| ccatctcccg cgccacccgg ggcccgggga ggcctgggac tcccggagca cttcctgcca | 2880 |
| cccccaccct catccagatc cccgtcatct agccccgggc agctgggcca gcctcccggg | 2940 |
| gagttgtccc taggtctggc cactggccca ctgagcacgc cagagacacc cccacggcag | 3000 |
| cctgagccgc cgtcccttgt ggcaggggcc tctgggggg cttccctgt aggctttact | 3060 |
| ccccgaggag gtctcagccc ccctggccac agcccaggcc cccaagaac cttcccgagt | 3120 |
| gccccgcccc gggcctctgg ctcccacgga tccttgctcc tgccacctgc atccagcccc | 3180 |
| ccaccacccc aggtccccca cgccggggc acacccccgc tcaccccgg ccgcctcacc | 3240 |
| caggacctca agctcatctc cgcgtctcag ccagccctgc ctcaggacgg ggcgcagact | 3300 |
| ctccgcagag cctcccccgca ctcctcaggg gagtccatgg ctgccttccc gctcttcccc | 3360 |
| agggctgggg gtggcagcgg gggcagtggg agcagcgggg gcctcggtcc ccctgggagg | 3420 |
| ccctatggtg ccatccccgg ccagcacgtc actctgcctc ggaagacatc ctcaggttct | 3480 |
| ttgccacccc ctctgtcttt gtttggggca agagccacct cttctggggg gccccctctg | 3540 |
| actgctggac cccagaggga acctggggcc aggcctgagc cagtgcgctc caaactgcca | 3600 |
| tccaatctat ga | 3612 |

<210> SEQ ID NO 5
<211> LENGTH: 1434
<212> TYPE: DNA
<213> ORGANISM: Homo Sapiens
<220> FEATURE:
<221> NAME/KEY: gene
<222> LOCATION: (1)..(1434)
<223> OTHER INFORMATION: beta-1 adrenergic receptor, coding sequence
      (Accession: NM 000684)

<400> SEQUENCE: 5

| | |
|---|---|
| atgggcgcgg ggtgctcgt cctgggcgcc tccgagcccg gtaacctgtc gtcggccgca | 60 |
| ccgctccccg acggcgcggc caccgcggcg cggctgctgg tgcccgcgtc gccgcccgcc | 120 |
| tcgttgctgc ctcccgccag cgaaagcccc gagccgctgt tcagcagtg gacagcgggc | 180 |
| atgggtctgt tgatggcgct catcgtgctg ctcatcgtgg cgggcaatgt gctggtgatc | 240 |
| gtggccatcg ccaagacgcc gcggctgcag acgctcacca acctcttcat catgtccctg | 300 |

-continued

```
gccagcgccg acctggtcat ggggctgctg gtggtgccgt tcgggccac catcgtggtg      360 tggggccgct gggagtacgg ctccttcttc tgcgagctgt ggacctcagt ggacgtgctg      420
tgcgtgacgg ccagcatcga gaccctgtgt gtcattgccc tggaccgcta cctcgccatc      480
acctcgccct tccgctacca gagcctgctg acgcgcgcgc gggcgcgggg cctcgtgtgc      540
accgtgtggg ccatctcggc cctggtgtcc ttcctgccca tcctcatgca ctggtggcgg      600
gcggagagcg acgaggcgcg ccgctgctac aacgacccca agtgctgcga cttcgtcacc      660
aaccgggcct acgccatcgc ctcgtccgta gtctccttct acgtgcccct gtgcatcatg      720
gccttcgtgt acctgcgggt gttccgcgag gcccagaagc aggtgaagaa gatcgacagc      780
tgcgagcgcc gtttcctcgg cggcccagcg cggccgccct cgcctcgcc ctcgcccgtc       840 cccgcgcccg cgccgccgcc cggacccccg cgccccgccg ccgccgccgc caccgccccg      900
ctggccaacg ggcgtgcggg taagcggcgg ccctcgcgcc tcgtggccct acgcgagcag      960
aaggcgctca agacgctggg catcatcatg ggcgtcttca cgctctgctg gctgcccttc     1020
ttcctggcca acgtggtgaa ggccttccac cgcgagctgg tgcccgaccg cctcttcgtc     1080
ttcttcaact ggctgggcta cgccaactcg gccttcaacc ccatcatcta ctgccgcagc     1140
cccgacttcc gcaaggcctt ccagggactg ctctgctgcg cgcgcagggc tgcccgccgg     1200
cgccacgcga cccacggaga ccggccgcgc gcctcgggct gtctggcccg gcccggaccc     1260
ccgccatcgc ccggggccgc ctcggacgac gacgacgacg atgtcgtcgg ggccacgccg     1320
cccgcgcgcc tgctggagcc ctgggccggc tgcaacggcg gggcggcggc ggacagcgac     1380
tcgagcctgg acgagccgtg ccgccccggc ttcgcctcgg aatccaaggt gtag            1434
```

<210> SEQ ID NO 6
<211> LENGTH: 1242
<212> TYPE: DNA
<213> ORGANISM: Homo Sapiens
<220> FEATURE:
<221> NAME/KEY: gene
<222> LOCATION: (1)..(1242)
<223> OTHER INFORMATION: beta-2 adrenergic receptor, coding sequence
      (Accession: NM 000024)

<400> SEQUENCE: 6

```
atggggcaac ccgggaacgg cagcgccttc ttgctggcac ccaatagaag ccatgcgccg       60
gaccacgacg tcacgcagca aagggacgag gtgtgggtgg tgggcatggg catcgtcatg      120
tctctcatcg tcctggccat cgtgtttggc aatgtgctgg tcatcacagc cattgccaag      180
ttcgagcgtc tgcagacggt caccaactac ttcatcactt cactggcctg tgctgatctg      240
gtcatgggcc tggcagtggt gcccttgggg gccgcccata ttcttatgaa aatgtggact      300
tttggcaact tctggtgcga gttttggact tccattgatg tgctgtgcgt cacggccagc      360
attgagaccc tgtgcgtgat cgcagtggat cgctactttg ccattacttc acctttcaag      420
taccagagcc tgctgaccaa gaataaggcc cgggtgatca ttctgatggt gtggattgtg      480
tcaggcctta cctccttctt gcccattcag atgcactggt accgggccac ccaccaggaa      540
gccatcaact gctatgccaa tgagacctgc tgtgacttct tcacgaacca agcctatgcc      600
attgcctctt ccatcgtgtc cttctacgtt cccctggtga tcatggtctt cgtctactcc      660
agggtctttc aggaggccaa aaggcagctc cagaagattg acaaatctga gggccgcttc      720
catgtccaga accttagcca ggtggagcag gatgggcgga cggggcatgg actccgcaga      780
tcttccaagt tctgcttgaa ggagcacaaa gccctcaaga cgttaggcat catcatgggc      840
```

| actttcaccc | tctgctggct | gcccttcttc | atcgttaaca | ttgtgcatgt | gatccaggat | 900 |
| aacctcatcc | gtaaggaagt | ttacatcctc | ctaaattgga | taggctatgt | caattctggt | 960 |
| ttcaatcccc | ttatctactg | ccggagccca | gatttcagga | ttgccttcca | ggagcttctg | 1020 |
| tgcctgcgca | ggtcttcttt | gaaggcctat | gggaatggct | actccagcaa | cggcaacaca | 1080 |
| ggggagcaga | gtggatatca | cgtggaacag | gagaaagaaa | ataaactgct | gtgtgaagac | 1140 |
| ctcccaggca | cggaagactt | tgtgggccat | caaggtactg | tgcctagcga | taacattgat | 1200 |
| tcacaaggga | ggaattgtag | tacaaatgac | tcactgctgt | aa | | 1242 |

<210> SEQ ID NO 7
<211> LENGTH: 7062
<212> TYPE: DNA
<213> ORGANISM: Homo Sapiens
<220> FEATURE:
<221> NAME/KEY: gene
<222> LOCATION: (1)..(7062)
<223> OTHER INFORMATION: T-type calcium channel alpha 1H subunit (CACNA1H), mRNA (Accession: AF051946)

<400> SEQUENCE: 7

| atgaccgagg | gcgcacgggc | cgccgacgag | gtccgggtgc | ccctgggcgc | gccgcccct | 60 |
| ggccctgcgg | cgttggtggg | ggcgtccccg | gagagccccg | gggcgccggg | acgcgaggcg | 120 |
| gagcgggggt | ccgagctcgg | cgtgtcaccc | tccgagagcc | cggcggccga | gcgcggcgcg | 180 |
| gagctgggtg | ccgacgagga | gcagcgcgtc | ccgtacccgg | ccttggcggc | cacggtcttc | 240 |
| ttctgcctcg | gtcagaccac | gcggccgcgc | agctggtgcc | tccggctggt | ctgcaaccca | 300 |
| tggttcgagc | acgtgagcat | gctggtaatc | atgctcaact | gcgtgaccct | gggcatgttc | 360 |
| cggccctgtg | aggacgttga | gtgcggctcc | gagcgctgca | acatcctgga | ggcctttgac | 420 |
| gccttcattt | tcgcctttt | tgcggtggag | atggtcatca | agatggtggc | cttggggctg | 480 |
| ttcgggcaga | agtgttacct | gggtgacacg | tggaatttctt | catcgtcgtg | | 540 |
| gcgggcatga | tggagtactc | gttggacgga | cacaacgtga | gcctctcggc | tatcaggacc | 600 |
| gtgcgggtgc | tgcggccccct | ccgcgccatc | aaccgcgtgc | ctagcatgcg | gatcctggtc | 660 |
| actctgctgc | tggatacgct | gcccatgctc | gggaacgtcc | ttctgctgtg | cttcttcgtc | 720 |
| ttcttcattt | tcggcatcgt | tggcgtccag | ctctgggctg | gcctcctgcg | gaaccgctgc | 780 |
| ttcctggaca | gtgcctttgt | caggaacaac | aacctgacct | tcctgcggcc | gtactaccag | 840 |
| acggaggagg | gcgaggagaa | cccgttcatc | tgctcctcac | gccgagacaa | cggcatgcag | 900 |
| aagtgctcgc | acatccccgg | ccgccgcgag | ctgcgcatgc | cctgcaccct | gggctgggag | 960 |
| gcctacacgc | agccgcaggc | cgaggggggtg | ggcgctgcac | gcaacgcctg | catcaactgg | 1020 |
| aaccagtact | acaacgtgtg | ccgctcgggt | gactccaacc | cccacaacgg | tgccatcaac | 1080 |
| ttcgacaaca | tcggctacgc | ctggatcgcg | atcttccagg | tgatcacgct | ggaaggctgg | 1140 |
| gtggacatca | tgtactacgt | catggacgcc | cactcattct | acaacttcat | ctatttcatc | 1200 |
| ctgctcatca | tcgtgggctc | cttcttcatg | atcaacctgt | gcctggtggt | gattgccacg | 1260 |
| cagttctcgg | agacgaagca | gcgggagagt | cagctgatgc | gggagcagcg | ggcacgccac | 1320 |
| ctgtccaacg | acagcacgct | ggccagcttc | tccgagcctg | gcagctgcta | cgaagagctg | 1380 |
| ctgaagtacg | tgggccacat | attccgcaag | gtcaagcggc | gcagcttgcg | cctctacgcc | 1440 |
| cgctggcaga | gccgctggcg | caagaaggtg | gaccccagtg | ctgtgcaagg | ccagggtccc | 1500 |
| gggcaccgcc | agcgccgggc | aggcaggcac | acagcctcgg | tgcaccacct | ggtctaccac | 1560 |

```
caccatcacc accaccacca ccactaccat ttcagccatg cagccccccg caggcccggc      1620
cccgagccag gcgcctgcga caccaggctg gtccgagctg gcgcgccccc ctcgccacct      1680
tccccaggcc gcggaccccc cgacgcagag tctgtgcaca gcatctacca tgccgactgc      1740
cacatagagg ggccgcagga gagggccegg gtggcacatg ccgcagccac tgctgctgcc      1800
agcctcaggc tggccacagg gctgggcacc atgaactacc ccacgatcct gccctcaggg      1860
gtgggcagcg gcaaaggcag caccagcccc ggacccaagg ggaagtgggc cggtggaccg      1920
ccaggcaccg gggggcacgg cccgttgagc ttgaacagcc ctgatcccta cgagaagatc      1980
ccgcatgtgg ccggggagca tggactgggc caagcccctg ccatctgtc  gggcctcagt      2040 gtgccctgcc ccctgcccag cccccagcg  ggcacactga cctgtgagct gaagagctgc      2100
ccgtactgca cccgtgccct ggaggacccg gagggtgagc tcagcggctc ggaaagtgga      2160
gactcagatg gccgtggcgt ctatgaattc acgcaggacg tccggcacgg tgaccgctgg      2220
gaccccacgc gaccaccccg tgcgacggac acaccaggcc caggcccagg cagcccccag      2280
cggcgggcac agcagagggc agccccgggc gagccaggct ggatgggccg cctctgggtt      2340
accttcagcg gcaagctgcg ccgcatcgtg gacagcaagt acttcagccg tggcatcatg      2400
atggccatcc ttgtcaacac gctgagcatg ggcgtggagt accatgagca gcccgaggag      2460
ctgactaatg ctctggagat cagcaacatc gtgttcacca gcatgtttgc cctggagatg      2520
ctgctgaagc tgctggcctg cggccctctg ggctacatcc ggaacccgta caacatcttc      2580
gacggcatca tcgtggtcat cagcgtctgg gagatcgtgg ggcaggcgga cggtggcttg      2640
tctgtgctgc gcaccttccg gctgctgcgt gtgctgaagc tggtgcgctt tctgccagcc      2700
ctgcggcgcc agtcgtggt  gctggtgaag accatggaca acgtggctac cttctgcacg      2760
ctgctcatgc tcttcatttt catcttcagc atcctgggca tgcacctttt cggctgcaag      2820
ttcagcctga agacagacac cggagacacc gtgcctgaca ggaagaactt cgactccctg      2880
ctgtgggcca tcgtcaccgt gttccagatc ctgacccagg aggactggaa cgtggtcctg      2940
tacaacggca tggcctccac ctcctcctgg gccgccctct acttcgtggc cctcatgacc      3000
ttcggcaact atgtgctctt caacctgctg gtggccatcc tcgtggaggg cttccaggcg      3060
gagggcgatg ccaacagatc cgacacggac gaggacaaga cgtcggtcca cttcgaggag      3120
gacttccaca agctcagaga actccagacc acagagctga agatgttcc  cctggccgtg      3180 accccccaacg ggcacctgga gggacgaggc agcctgtccc ctcccctcat catgtgcaca      3240
gctgccacgc ccatgcctac ccccaagagc tcaccattcc tggatgcagc ccccagcctc      3300
ccagactctc ggcgtggcag cagcagctcc ggggacccgc cactgggaga ccagaagcct      3360
ccggccagcc tccgaagttc tccctgtgcc cctggggcc  ccagtggcgc ctggagcagc      3420
cggcgctcca gctggagcag cctgggccgt gccccagcc  tcaagcgccg cggccagtgt      3480
ggggaacgtg agtccctgct gtctggcgag ggcaagggca gcaccgacga cgaagctgag      3540
gacggcaggg ccgcgcccgg ggcccgtgcc accccactgc ggcgggccga gtccctggac      3600
ccacggcccc tgcggccggc cgccctcccg cctaccaagt gccgcgatcg cgacgggcag      3660
gtggtggccc tgcccagcga cttcttcctg cgcatcgaca gccaccgtga ggatgcagcc      3720
gagcttgacg acgactcgga ggacagctgc tgcctccgcc tgcataaagt gctggagccc      3780
tacaagcccc agtggtgccg gagccgcgag ggctgggccc tctacctctt ctccccacag      3840
aaccggttcc gcgtctcctg ccagaaggtc atcacacaca agatgtttga tcacgtggtc      3900
```

```
ctcgtcttca tcttcctcaa ctgcgtcacc atcgccctgg agaggcctga cattgatccc    3960
ggcagcaccg agcgggtctt cctcagcgtc tccaattaca tcttcacggc catcttcgtg    4020
gcggagatga tggtgaaggt ggtggccctg ggctgctgt ccggcgagca cgcctacctg     4080
cagagcagct ggaacctgct ggatgggctg ctggtgctgg tgtccctggt ggacattgtc    4140
gtggccatgg cctcggctgg tggcgccaag atcctgggtg ttctgcgcgt gctgcgtctg    4200
ctgcggaccc tgcggcctct gagggtcatc agccgggccc cgggcctcaa gctggtggtg    4260
gagacgctga tatcatcact caggcccatt ggaacatcg tcctcatctg ctgcgccttc     4320
ttcatcattt ttggcatttt gggtgtgcag ctcttcaaag ggaagttcta ctactgcgag    4380
ggccccgaca ccaggaacat ctccaccaag gcacagtgcc gggccgccca ctaccgctgg    4440
gtgcgacgca agtacaactt cgacaacctg ggccaggccc tgatgtcgct gttcgtgctg    4500
tcatccaagg atggatgggt gaacatcatg tacgacgggc tggatgccgt gggtgtcgac    4560
cagcagcctg tgcagaacca caaccctgg atgctgctgt acttcatctc cttcctgctc     4620
atcgtcagct tcttcgtgct caacatgttc gtgggcgtcg tggtcgagaa cttccacaag    4680
tgccggcagc accaggaggc ggaggaggcg cggcggcgag aggagaagcg gctgcggcgc    4740
ctagagagga ggcgcaggag cactttcccc agcccagagg cccagcgccg gccctactat    4800
gccgactact cgcccacgcg ccgctccatt cactcgctgt gcaccagcca ctatctcgac    4860
ctcttcatca ccttcatcat ctgtgtcaac gtcatcacca tgtccatgga gcactataac    4920
caacccaagt cgctggacga ggccctcaag tactgcaact acgtcttcac catcgtgttt    4980
gtcttcgagg ctgcactgaa gctggtagca tttgggttcc gtcggttctt caaggacagg    5040
tggaaccagc tggacctggc catcgtgctg ctgtcactca tgggcatcac gctggaggag    5100
atagagatga gcgccgcgct gcccatcaac cccaccatca tccgcatcat gcgcgtgctt    5160
cgcattgccc gtgtgctgaa gctgctgaag atggctacgg gcatgcgcgc cctgctggac    5220
actgtggtgc aagctctccc ccaggtgggg aacctgggcc ttcttttcat gctcctgttt    5280
tttatctatg ctgcgctggg agtggagctg ttcgggaggc tggagtgcag tgaagacaac    5340
ccctgcgagg gcctgagcag gcacgccacc ttcagcaact tcggcatggc cttcctcacg    5400
ctgttccgcg tgtccacggg ggacaactgg aacgggatca tgaaggacac gctgcgcgag    5460
tgctcccgtg aggacaagca ctgcctgagc tacctgccgg ccctgtcgcc cgtctacttc    5520
gtgaccttcg tgctggtggc ccagttcgtg ctggtgaacg tggtggtggc cgtgctcatg    5580
aagcacctgg aggagagcaa caaggaggca cgggaggatg cggagctgga cgccgagatc    5640
gagctggaga tggcgcaggg ccccgggagt gcacgccggg tggacgcgga caggcctccc    5700
ttgccccagg agagtccggg cgccagggat gccccaaacc tggttgcacg caaggtgtcc    5760
gtgtccagga tgctctcgct gcccaacgac agctacatgt tcaggcccgt ggtgcctgcc    5820
tcggcgcccc accccgccc gctgcaggag gtggagatgg agacctatgg ggccggcacc    5880
cccttgggct ccgttgcctc tgtgcactct ccgcccgcag agtcctgtgc ctccctccag    5940
atcccactgg ctgtgtcgtc cccagccagg agcggcgagc ccctccacgc cctgtcccct    6000
cggggcacag cccgctcccc cagtctcagc cggctgctct gcagacagga ggctgtgcac    6060
accgattcct tggaagggaa gattgacagc cctagggaca ccctggatcc tgcagagcct    6120
ggtgagaaaa ccccggtgag gccggtgacc cagggggggct ccctgcagtc cccaccacgc    6180
tccccacggc ccgccagcgt ccgcactcgt aagcatacct tcgacagcgc ctgcgtctcc    6240
agccggccgg cggccccagg cggagaggag gccgaggcct cggacccagc cgacgaggag    6300
```

| | |
|---|---|
| gtcagccaca tcaccagctc cgcctgcccc tggcagccca cagccgagcc ccatggcccc | 6360 |
| gaagcctctc cggtggccgg cggcgagcgg gacctgcgca ggctctacag cgtggatgct | 6420 |
| cagggcttcc tggacaagcc gggccgggca gacgagcagt ggcggccctc ggcggagctg | 6480 |
| ggcagcgggg agcctgggga ggcgaaggcc tggggccctg aggccgagcc cgctctgggt | 6540 |
| gcgcgcagaa agaagaagat gagcccccc tgcatctcgg tggaaccccc tgcggaggac | 6600 |
| gagggctctg cgcggccctc cgcggcagag ggcggcagca ccacactgag cgcaggacc | 6660 |
| ccgtcctgtg aggccacgcc tcacagggac tccctggagc ccacagaggg ctcaggcgcc | 6720 |
| gggggggacc ctgcagccaa gggggagcgc tggggccagg cctcctgccg ggctgagcac | 6780 |
| ctgaccgtcc ccagctttgc ctttgagccg ctggacctcg gggtcccag tggagaccct | 6840 |
| ttcttggacg gtagccacag tgtgacccca gaatccagag cttcctcttc aggggccata | 6900 |
| gtgcccctgg aaccccaga atcagagcct ccatgcccg tcggtgaccc ccagagaag | 6960 |
| aggcgggggc tgtacctcac agtccccag tgtcctctgg agaaaccagg gtcccctca | 7020 |
| gccacccctg ccccaggggg tggtgcagat gaccccgtgt ag | 7062 |

<210> SEQ ID NO 8
<211> LENGTH: 6417
<212> TYPE: DNA
<213> ORGANISM: Homo Sapiens
<220> FEATURE:
<221> NAME/KEY: gene
<222> LOCATION: (1)..(6417)
<223> OTHER INFORMATION: T-type calcium channel alpha 1H subunit
      (CACNA1H), mRNA (Accession: NM 000719)

<400> SEQUENCE: 8

| | |
|---|---|
| atggtcaatg agaatacgag gatgtacatt ccagaggaaa accaccaagg ttccaactat | 60 |
| gggagcccac gccccgccca tgccaacatg aatgccaatg cggcagcggg gctggcccct | 120 |
| gagcacatcc ccaccccggg ggctgccctg tcgtggcagg cggccatcga cgcagcccgg | 180 |
| caggctaagc tgatgggcag cgctggcaat gcgaccatct ccacagtcag ctccacgcag | 240 |
| cggaagcggc agcaatatgg gaaacccaag aagcagggca gcaccacggc cacacgcccg | 300 |
| ccccgagccc tgctctgcct gaccctgaag aaccccatcc ggagggcctg catcagcatt | 360 |
| gtcgaatgga aaccatttga ataattatt ttactgacta tttttgccaa ttgtgtggcc | 420 |
| ttagcgatct atattcccct tccagaagat gattccaacg ccaccaattc caacctggaa | 480 |
| cgagtggaat atctctttct cataattttt acggtggaag cgttttaaa agtaatcgcc | 540 |
| tatggactcc tctttcaccc caatgcctac ctccgcaacg gctggaacct actagatttt | 600 |
| ataattgtgg ttgtgggct ttttagtgca attttagaac aagcaaccaa agcagatggg | 660 |
| gcaaacgctc tcggagggaa aggggccgga tttgatgtga aggcgctgag ggccttccgc | 720 |
| gtgctgcgcc cctgcggct ggtgtccgga gtcccaagtc tccaggtggt cctgaattcc | 780 |
| atcatcaagg ccatggtccc cctgctgcac atcgccctgc ttgtgctgtt tgtcatcatc | 840 |
| atctacgcca tcatcggctt ggagctcttc atggggaaga tgcacaagac ctgctacaac | 900 |
| caggagggca tagcagatgt tccagcagaa gatgacccct cccttgtgc gctggaaacg | 960 |
| ggccacgggc ggcagtgcca gaacggcacg gtgtgcaagc ccggctggga tggtcccaag | 1020 |
| cacggcatca ccaactttga caactttgcc ttcgccatgc tcacggtgtt ccagtgcatc | 1080 |
| accatggagg gctggacgga cgtgctgtac tgggtcaatg atgccgtagg aagggactgg | 1140 |
| ccctggatct attttgttac actaatcatc ataggtcat tttttgtact taactggtt | 1200 |

```
ctcggtgtgc ttagcggaga gttttccaaa gagagggaga aggccaaggc ccggggagat    1260
ttccagaagc tgcgggagaa gcagcagcta gaagaggatc tcaaaggcta cctggattgg    1320
atcactcagg ccgaagacat cgatcctgag aatgaggacg aaggcatgga tgaggagaag    1380
ccccgaaaca tgagcatgcc caccagtgag accgagtccg tcaacaccga aaacgtggct    1440
ggaggtgaca tcgagggaga aaactgcggg gccaggctgg cccaccggat ctccaagtca    1500
aagttcagcc gctactggcg ccggtggaat cggttctgca gaaggaagtg ccgcgccgca    1560
gtcaagtcta atgtcttcta ctggctggtg attttcctgg tgttcctcaa cacgctcacc    1620
attgcctctg agcactacaa ccagcccaac tggctcacag aagtccaaga cacggcaaac    1680
aaggccctgc tggccctgtt cacggcagag atgctcctga agatgtacag cctgggcctg    1740
caggcctact tcgtgtccct cttcaaccgc tttgactgct tcgtcgtgtg tggcggcatc    1800
ctggagacca tcctggtgga gaccaagatc atgtccccac tgggcatctc cgtgctcaga    1860
tgcgtccggc tgctgaggat tttcaagatc acgaggtact ggaactcctt gagcaacctg    1920
gtggcatcct tgctgaactc tgtgcgctcc atcgcctccc tgctccttct cctcttcctc    1980
ttcatcatca tcttctccct cctggggatg cagctctttg gaggaaagtt caactttgat    2040
gagatgcaga cccggaggag cacattcgat aacttccccc agtccctcct cactgtgttt    2100
cagatcctga ccggggagga ctggaattcg gtgatgtatg atgggatcat ggcttatggc    2160 ggccctctt ttccagggat gttagtctgt atttacttca tcatcctctt catctgtgga    2220
aactatatcc tactgaatgt gttcttggcc attgctgtgg acaacctggc tgatgctgag    2280
agcctcacat ctgcccaaaa ggaggaggaa gaggagaagg agagaaagaa gctggccagg    2340
actgccagcc cagagaagaa acaagagttg gtggagaagc cggcagtggg ggaatccaag    2400
gaggagaaga ttgagctgaa atccatcacg gctgacggag agtctccacc cgccaccaag    2460
atcaacatgg atgacctcca gcccaatgaa aatgaggata gagccccta ccccaaccca    2520 gaaactacag gagaagagga tgaggaggag ccagagatgc ctgtcggccc tcgcccacga    2580
ccactctctg agcttcacct taaggaaaag gcagtgccca tgccagaagc cagcgcgttt    2640
ttcatcttca gctctaacaa caggtttcgc ctccagtgcc accgcattgt caatgacacg    2700
atcttcacca acctgatcct cttcttcatt ctgctcagca gcatttccct ggctgctgag    2760
gacccggtcc agcacacctc cttcaggaac catattctgt tttattttga tattgttttt    2820
accaccattt tcaccattga aattgctctg aagatgactg cttatggggc tttcttgcac    2880
aagggttctt tctgccggaa ctacttcaac atcctggacc tgctggtggt cagcgtgtcc    2940
ctcatctcct ttggcatcca gtccagtgca atcaatgtcg tgaagatctt gcgagtcctg    3000
cgagtactca ggccctgag ggccatcaac agggccaagg ggctaaagca tgtggttcag    3060
tgtgtgtttg tcgccatccg gaccatcggg aacatcgtga ttgtcaccac cctgctgcag    3120
ttcatgtttg cctgcatcgg ggtccagctc ttcaagggaa agctgtacac ctgttcagac    3180
agttccaagc agacagaggc ggaatgcaag ggcaactaca tcacgtacaa agacggggag    3240
gttgaccacc ccatcatcca accccgcagc tgggagaaca gcaagtttga ctttgacaat    3300
gttctggcag ccatgatggc cctcttcacc gtctccacct tcgaagggtg ccagagctgc    3360
ctgtaccgct ccatcgactc ccacacggaa acaagggcc ccatctacaa ctaccgtgtg    3420
gagatctcca tcttcttcat catctacatc atcatcatcg ccttcttcat gatgaacatc    3480
ttcgtgggct tcgtcatcgt cacctttcag gagcagggg agcaggagta caagaactgt    3540
```

```
gagctggaca agaaccagcg acagtgcgtg aatacgccc tcaaggcccg gcccctgcgg      3600
aggtacatcc ccaagaacca gcaccagtac aaagtgtggt acgtggtcaa ctccacctac      3660
ttcgagtacc tgatgttcgt cctcatcctg ctcaacacca tctgcctggc catgcagcac      3720
tacggccaga gctgcctgtt caaaatcgcc atgaacatcc tcaacatgct cttcactggc      3780
ctcttcaccg tggagatgat cctgaagctc attgccttca acccaagca ctatttctgt       3840 gatgcatgga atacatttga cgccttgatt gttgtgggta gcattgttga tatagcaatc      3900
accgaggtaa acccagctga acatacccaa tgctctccct ctatgaacgc agaggaaaac      3960
tcccgcatct ccatcaccttt cttccgcctg ttccgggtca tgcgtctggt gaagctgctg     4020
agccgtgggg agggcatccg gacgctgctg tggaccttca tcaagtcctt ccaggccctg     4080
ccctatgtgg ccctcctgat cgtgatgctg ttcttcatct acgcggtgat cgggatgcag     4140
gtgtttggga aaattgccct gaatgatacc acagagatca accggaacaa caactttcag    4200
accttccccc aggccgtgct gctcctcttc aggtgtgcca ccggggaggc ctggcaggac    4260
atcatgctgg cctgcatgcc aggcaagaag tgtgccccag agtccgagcc cagcaacagc    4320
acggagggtg aaacaccctg tggtagcagc tttgctgtct tctacttcat cagcttctac     4380
atgctctgtg ccttcctgat catcaacctc tttgtagctg tcatcatgga caactttgac    4440
tacctgacaa gggactggtc catccttggt ccccaccacc tggatgagtt taaaagaatc    4500
tgggcagagt atgaccctga agccaagggg cgtatcaaac acctggatgt ggtgaccctc    4560
ctccggcgga ttcagccgcc actaggttttt gggaagctgt gccctcaccg cgtggcttgc    4620
aaacgcctgg tctccatgaa catgcctctg aacagcgacg ggacagtcat gttcaatgcc    4680
accctgtttg ccctggtcag gacggccctg aggatcaaaa cagaagggaa cctagaacaa    4740
gccaatgagg agctgcgggc gatcatcaag aagatctgga gcggaccag catgaagctg    4800 ctggaccagg tggtgccccc tgcaggtgat gatgaggtca ccgttggcaa gttctacgcc    4860
acgttcctga tccaggagta cttccggaag ttcaagaagc gcaaagagca gggccttgtg    4920
ggcaagccct cccagaggaa cgcgctgtct ctgcaggctg gcttgcgcac actgcatgac    4980
atcgggcctg agatccgacg ggccatctct ggagatctca ccgctgagga ggagctggac    5040
aaggccatga aggaggctgt gtccgctgct tctgaagatg acatcttcag gagggccggt    5100
ggcctgttcg gcaaccacgt cagctactac caaagcgacg gccggagcgc cttcccccag    5160
accttcacca ctcagcgccc gctgcacatc aacaaggcgg gcagcagcca gggcgacact    5220
gagtcgccat cccacgagaa gctggtggac tccaccttca cccccgagcag ctactcgtcc    5280 accggctcca acgccaacat caacaacgcc aacaacaccg cctgggtcg cctccctcgc    5340 cccgccggct accccagcac agtcagcact gtggagggcc acgggccccc cttgtccccct    5400 gccatccggg tgcaggaggt ggcgtggaag ctcagctcca acaggtgcca ctcccgggag    5460
agccaggcag ccatggcggg tcaggaggag acgtctcagg atgagaccta tgaagtgaag    5520
atgaaccatg acacgaggc ctgcagtgag cccagcctgc tctccacaga gatgctctcc    5580
taccaggatg acgaaaatcg gcaactgacg ctcccagagg aggacaagag ggacatccgg    5640
caatctccga agagggttt cctccgctct gcctcactag gtcgaagggc ctccttccac    5700
ctggaatgtc tgaagcgaca gaaggaccga ggggagaca tctctcagaa gacagtcctg     5760
cccttgcatc tggttcatca tcaggcattg gcagtggcag gcctgagccc cctcctccag    5820
agaagccatt cccctgcctc attccctagg ccttttgcca cccaccagc cacacctggc    5880 agccgaggct ggcccccaca gcccgtcccc accctgcggc ttgagggggt cgagtccagt    5940
```

```
gagaaactca acagcagctt cccatccatc cactgcggct cctgggctga gaccacccc     6000 ggtggcgggg gcagcagcgc cgcccggaga gtccggcccg tctccctcat ggtgcccagc    6060
caggctgggg ccccagggag gcagttccac ggcagtgcca gcagcctggt ggaagcggtc    6120
ttgatttcag aaggactggg gcagtttgct caagatccca agttcatcga ggtcaccacc    6180
caggagctgg ccgacgcctg cgacatgacc atagaggaga tggagagcgc ggccgacaac    6240
atcctcagcg ggggcgcccc acagagcccc aatggcgccc tcttacccct tgtgaactgc    6300
agggacgcgg ggcaggaccg agccgggggc gaagaggacg cgggctgtgt gcgcgcgcgg    6360
ggtcgaccga gtgaggagga gctccaggac agcagggtct acgtcagcag cctgtag       6417

<210> SEQ ID NO 9
<211> LENGTH: 215
<212> TYPE: DNA
<213> ORGANISM: Rabbit
<220> FEATURE:
<221> NAME/KEY: gene
<222> LOCATION: (1)..(215)
<223> OTHER INFORMATION: K+/pacemaker channel beta subunit mirp1
      (mink-related peptide, HCN channel subunit, KCNE2) mRNA (partial
      coding sequence)

<400> SEQUENCE: 9
atgcggagaa cttctactat gtcatcctct acctcatggt gatgattggc atgttctcct      60
tcatcatcgt ggccatcctg gtgagcacgg tgaagtccaa gaggcgggaa cactccaacg     120 accccctacca ccagtacatc gtggaggact ggcaggaaaa gtacaaaagc cagattttgc    180
atttcgaaga agccaaggcc accatccatg agaac                                215

<210> SEQ ID NO 10
<211> LENGTH: 372
<212> TYPE: DNA
<213> ORGANISM: Homo Sapiens
<220> FEATURE:
<221> NAME/KEY: gene
<222> LOCATION: (1)..(372)
<223> OTHER INFORMATION: potassium voltage-gated channel, Isk-related
      family, member 2 (KCNE2), mRNA. Complete on 3' end (3 prime).
      (Assession: NM 172201)

<400> SEQUENCE: 10
atgtctactt tatccaattt cacacagacg ctggaagacg tcttccgaag gattttttatt     60 acttatatgg acaattggcg ccagaacaca acagctgagc aagaggccct ccaagccaaa    120
gttgatgctg agaacttcta ctatgtcatc ctgtacctca tggtgatgat tggaatgttc    180
tctttcatca tcgtggccat cctggtgagc actgtgaaat ccaagagacg ggaacactcc    240
aatgacccct accaccagta cattgtagag gactggcagg aaaagtacaa gagccaaatc    300
ttgaatctag aagaatcgaa ggccaccatc catgagaaca ttggtgcggc tgggttcaaa    360 atgtcccct ga                                                         372

<210> SEQ ID NO 11
<211> LENGTH: 1401
<212> TYPE: DNA
<213> ORGANISM: Homo Sapiens
<220> FEATURE:
<221> NAME/KEY: gene
<222> LOCATION: (1)..(1401)
<223> OTHER INFORMATION: cholinergic receptor, muscarinic 2 (CHRM2),
      mRNA. (Accession: NM 000739)

<400> SEQUENCE: 11
```

```
atgaataact caacaaactc ctctaacaat agcctggctc ttacaagtcc ttataagaca      60
tttgaagtgg tgtttattgt cctggtggct ggatccctca gtttggtgac cattatcggg     120
aacatcctag tcatggtttc cattaaagtc aaccgccacc tccagaccgt caacaattac     180
tttttattca gcttggcctg tgctgacctt atcataggtg ttttctccat gaacttgtac     240
accctctaca ctgtgattgg ttactggcct ttgggacctg tggtgtgtga cctttggcta     300
gccctggact atgtggtcag caatgcctca gttatgaatc tgctcatcat cagctttgac     360
aggtacttct gtgtcacaaa acctctgacc tacccagtca agcggaccac aaaaatggca     420
ggtatgatga ttgcagctgc ctgggtcctc tctttcatcc tctgggctcc agccattctc     480
ttctggcagt tcattgtagg ggtgagaact gtggaggatg gggagtgcta cattcagttt     540
ttttccaatg ctgctgtcac ctttggtacg gctattgcag ccttctattt gccagtgatc     600
atcatgactg tgctatattg gcacatatcc cgagccagca gagcaggat aaagaaggac      660 aagaaggagc tgttgccaa ccaagacccc gtttctccaa gtctggtaca aggaaggata     720
gtgaagccaa acaataacaa catgcccagc agtgacgatg gcctggagca acaaaaatc      780 cagaatggca agcccccag ggatcctgtg actgaaaact gtgttcaggg agaggagaag      840
gagagctcca atgactccac ctcagtcagt gctgttgcct ctaatatgag agatgatgaa     900
ataacccagg atgaaaacac agtttccact tccctgggcc attccaaaga tgagaactct     960
aagcaaacat gcatcagaat tggcaccaag accccaaaaa gtgactcatg taccccaact    1020
aataccaccg tggaggtagt gggtcttca ggtcagaatg agatgaaaa gcagaatatt     1080 gtagccc gca agattgtgaa gatgactaag cagcctgcaa aaaagaagcc tcctccttcc    1140
cgggaaaaga agtcaccag acaatcttg gctattctgt ggctttcat catcacttgg      1200 gcccc cataca atgtcatggt gctcattaac acctttgtg caccttgcat ccccaacact    1260
gtgtggacaa ttggttactg gctttgttac atcaacagca ctatcaaccc tgcctgctat    1320
gcactttgca atgccacctt caagaagacc tttaaacacc ttctcatgtg tcattataag    1380
aacataggcg ctacaaggta a                                              1401
```

<210> SEQ ID NO 12
<211> LENGTH: 1773
<212> TYPE: DNA
<213> ORGANISM: Homo Sapiens
<220> FEATURE:
<221> NAME/KEY: gene
<222> LOCATION: (1)..(1773)
<223> OTHER INFORMATION: cholinergic receptor, muscarinic 3 (CHRM3), mRNA. (Accession: NM 000740)

<400> SEQUENCE: 12

```
atgaccttgc acaataacag tacaacctcg cctttgtttc aaacatcag ctcctcctgg       60 atacacagcc cctccgatgc agggctgccc ccgggaaccg tcactcattt cggcagctac     120
aatgtttctc gagcagctgg caatttctcc tctccagacg gtaccaccga tgaccctctg     180
ggaggtcata ccgtctggca agtggtcttc atcgctttct aacgggcat cctggccttg      240 gtgaccatca tcggcaacat cctggtaatt gtgtcattta aggtcaacaa gcagctgaag     300
acggtcaaca actacttcct cttaagcctg gcctgtgccg atctgattat cggggtcatt    360
tcaatgaatc tgtttacgac ctacatcatc atgaatcgat gggccttagg gaacttggcc    420
tgtgacctct ggcttgccat tgactacgta gccagcaatg cctctgttat gaatcttctg    480
gtcatcagct ttgacagata cttttccatc acgaggccgc tcacgtaccg agccaaacga    540
```

-continued

```
acaacaaaga gagccggtgt gatgatcggt ctggcttggg tcatctcctt tgtcctttgg      600
gctcctgcca tcttgttctg gcaatacttt gttggaaaga gaactgtgcc tccgggagag      660
tgcttcattc agttcctcag tgagcccacc attacttttg cacagccat cgctgctttt       720 tatatgcctg tcaccattat gactatttta tactggagga tctataagga aactgaaaag      780
cgtaccaaag agcttgctgg cctgcaagcc tctgggacag aggcagagac agaaaacttt      840
gtccacccca cgggcagttc tcgaagctgc agcagttacg aacttcaaca gcaaagcatg      900
aaacgctcca acaggaggaa gtatggccgc tgccacttct ggttcacaac caagagctgg      960
aaacccagct ccgagcagat ggaccaagac cacagcagca gtgacagttg aacaacaat     1020 gatgctgctg cctccctgga gaactccgcc tcctccgacg aggaggacat ggctccgag     1080 acgagagcca tctactccat cgtgctcaag cttccgggtc acagcaccat cctcaactcc    1140
accaagttac cctcatcgga caacctgcag gtgcctgagg aggagctggg gatggtggac    1200
ttggagagga aagccgacaa gctgcaggcc cagaagagcg tggacgatgg aggcagtttt    1260
ccaaaaagct tctccaagct tcccatccag ctagagtcag ccgtggacac agctaagact    1320
tctgacgtca actcctcagt gggtaagagc acggccactc tacctctgtc cttcaaggaa    1380
gccactctgg ccaagaggtt tgctctgaag accagaagtc agatcactaa gcggaaaagg    1440
atgtccctgg tcaaggagaa gaaagcggcc cagaccctca gtgcgatctt gcttgccttc    1500
atcatcactt ggacccccata caacatcatg gttctggtga cacctttttg tgacagctgc    1560
atcccaaaaa ccttttggaa tctgggctac tggctgtgct acatcaacag caccgtgaac    1620
cccgtgtgct atgctctgtg caacaaaaca ttcagaacca ctttcaagat gctgctgctg    1680
tgccagtgtg acaaaaaaaa gaggcgcaag cagcagtacc agcagagaca gtcggtcatt    1740
tttcacaagc gcgcacccga gcaggccttg tag                                  1773
```

<210> SEQ ID NO 13
<211> LENGTH: 1284
<212> TYPE: DNA
<213> ORGANISM: Homo Sapiens
<220> FEATURE:
<221> NAME/KEY: gene
<222> LOCATION: (1)..(1284)
<223> OTHER INFORMATION: potassium inwardly-rectifying channel,
      subfamily J, member 2 (KCNJ2) (Accession: NM 000891)

<400> SEQUENCE: 13

```
atgggcagtg tgcgaaccaa ccgctacagc atcgtctctt cagaagaaga cggtatgaag       60
ttggccacca tggcagttgc aaatggcttt gggaacggga agagtaaagt ccacacccga      120
caacagtgca ggagccgctt tgtgaagaaa gatggccact gtaatgttca gttcatcaat      180
gtgggtgaga aggggcaacg gtacctcgca gacatcttca ccacgtgtgt ggacattcgc      240
tggcggtgga tgctggttat cttctgcctg gctttcgtcc tgtcatggct gttttttggc      300
tgtgtgtttt ggttgatagc tctgctccat ggggacctgg atgcatccaa agagggcaaa      360
gcttgtgtgt ccgaggtcaa cagcttcacg gctgccttcc tcttctccat tgagacccag      420
acaaccatag ctatggtttt cagatgtgtc acggatgaat gcccaattgc tgtttttcatg      480 gtggtgttcc agtcaatcgt gggctgcatc atcgatgctt tcatcattgg cgcagtcatg      540
gccaagatgg caaagccaaa gaagagaaac gagactcttg tcttcagtca caatgccgtg      600
attgccatga gagacggcaa gctgtgtttg atgtggcgag tggcaatcct tcggaaaagc      660
cacttggtgg aagctcatgt tcgagcacag ctcctcaaat ccagaattac ttctgaaggg      720
```

-continued

```
gagtatatcc ctctggatca aatagacatc aatgttgggt ttgacagtgg aatcgatcgt      780
atatttctgg tgtccccaat cactatagtc catgaaatag atgaagacag tcctttatat      840
gatttgagta acaggacatt tgacaacgca gactttgaaa tcgtggtcat actggaaggc      900
atggtggaag ccactgccat gacgacacag tgccgtagct cttatctagc aaatgaaatc      960
ctgtggggcc accgctatga gcctgtgctc tttgaagaga agcactacta caaagtggac     1020
tattccaggt tccacaaaac ttacgaagtc cccaacactc ccctttgtag tgccagagac     1080
ttagcagaaa agaaatatat cctctcaaat gcaaattcat tttgctatga aaatgaagtt     1140
gccctcacaa gcaaagagga agacgacagt gaaaatggag ttccagaaag cactagtacg     1200
gacacgcccc ctgacataga ccttcacaac caggcaagtg tacctctaga gcccaggccc     1260
ttacggcgag agtcggagat atga                                            1284
```

<210> SEQ ID NO 14
<211> LENGTH: 1968
<212> TYPE: DNA
<213> ORGANISM: Homo Sapiens
<220> FEATURE:
<221> NAME/KEY: gene
<222> LOCATION: (1)..(1968)
<223> OTHER INFORMATION: potassium voltage-gated channel, Shal-related
      subfamily, member 3 (KCND3), transcript variant 1. (Accession:
      NM 004980)

<400> SEQUENCE: 14

```
atggcggccg gagttgcggc ctggctgcct tttgcccggg ctgcggccat cgggtggatg       60
ccggtggcca actgccccat gcccctggcc ccggccgaca gaacaagcg gcaggatgag      120 ctgattgtcc tcaacgtgag tgggcggagg ttccagacct ggaggaccac gctggagcgc      180
tacccggaca ccctgctggg cagcacggag aaggagttct tcttcaacga ggacaccaag      240
gagtacttct tcgaccggga ccccgaggtg ttccgctgcg tgctcaactt ctaccgcacg      300
gggaagctgc actacccgcg ctacgagtgc atctctgcct acgacgacga gctggccttc      360
tacggcatcc tcccggagat catcggggac tgctgctacg aggagtacaa ggaccgcaag      420
agggagaacg ccgagcggct catggacgac aacgactcgg agaacaacca ggagtccatg      480
ccctcgctca gcttccgcca gaccatgtgg cgggccttcg agaacccccca caccagcacg      540 ctggccctgg tcttctacta cgtgactggc ttcttcatcg ctgtctcggt catcaccaac      600
gtggtggaga cggtgccgtg cggcacggtc ccgggcagca aggagctgcc gtgcggggag      660
cgctactcgg tggccttctt ctgcctggac acggcgtgcg tcatgatctt caccgtggag      720
tacctcctgc ggctcttcgc ggctcccagc cgctaccgct tcatccgcag cgtcatgagc      780
atcatcgacg tggtggccat catgccctac tacatcggtc tggtcatgac caacaacgag      840
gacgtgtccg gcgccttcgt cacgctccgg gtcttccgcg tcttcaggat cttcaagttt      900
tcccgccact cccagggcct gcggatcctg gctacacac tgaagagctg tgcctccgaa      960
ctgggctttc ttctcttctc cctcaccatg gccatcatca tctttgccac tgtgatgttt     1020
tatgccgaga agggctcctc ggccagcaag ttcacaagca tccctgcctc gttttggtac     1080
accattgtca ccatgaccac actggggtac ggagacatgt gcctaagac gattgcaggg     1140 aagatcttcg gctccatctg ctccttgagt ggcgtcctgg tcattgccct gccagtccct     1200
gtgattgttt ccaactttag ccggatttac caccagaatc agagagctga taacgcagg     1260 gcacaaaaga aggcccgcct tgccaggatc cgtgtggcca aaacaggcag ttcgaatgca     1320
```

```
tacctgcaca gcaagcgcaa cgggctcctc aacgaggcgc tggagctgac gggcacccca    1380
gaagaggagc acatgggcaa gaccacctca ctcatcgaga gccagcatca tcacctgctg    1440
cactgcctgg aaaaaaccac tgggttgtcc tatcttgtgg atgatcccct gttatctgta    1500
cgaacctcca ccatcaagaa ccacgagttt attgatgagc agatgtttga gcagaactgc    1560
atggagagtt caatgcagaa ctacccatcc acaagaagtc cctcactgtc cagccaccca    1620
ggcctcacta ccacctgctg ctcccgtcgt agtaagaaga ccacacacct gcccaattct    1680
aacctgccag ctactcgcct gcgcagcatg caagagctca gcacgatcca tcccagggc     1740 agtgagcagc cctccctcac aaccagtcgc tccagcctta atttgaaagc agacgacgga    1800
ctgagaccaa actgcaaaac atcccagatc accacagcca tcatcagcat ccccactccc    1860
ccagcgctaa ccccagaggg ggaaagtcgg ccaccccctg ccagcccagg ccccaacacg    1920
aacattcctt ccatagccag caatgttgtc aaggtctccg ccttgtaa                 1968
```

<210> SEQ ID NO 15
<211> LENGTH: 759
<212> TYPE: DNA
<213> ORGANISM: Homo Sapiens
<220> FEATURE:
<221> NAME/KEY: gene
<222> LOCATION: (1)..(759)
<223> OTHER INFORMATION: Kv channel interacting protein 2. (Accession: BC034685)

<400> SEQUENCE: 15

```
atgcggggcc agggccgcaa ggagagtttg tccgattccc gagacctgga cggctcctac    60
gaccagctca cgggccaccc tccagggccc actaaaaaag cgctgaagca gcgattcctc    120
aagctgctgc cgtgctgcgg gccccaagcc ctgccctcag tcagtgaaaa cagcgtggac    180
gatgaatttg aattgtccac cgtgtgtcac cggcctgagg gtctggagca gctgcaggag    240
caaaccaaat tcacgcgcaa ggagttgcag gtcctgtacc ggggcttcaa gaacgaatgt    300
cccagcggaa ttgtcaatga ggagaacttc aagcagattt actcccagtt ctttcctcaa    360
ggagactcca gcacctatgc cacttttctc ttcaatgcct tgacaccaa ccatgatggc    420 tcggtcagtt ttgaggactt tgtggctggt ttgtccgtga ttcttcgggg aactgtagat    480
gacaggctta attgggcctt caacctgtat gaccttaaca aggacggctg catcaccaag    540
gaggaaatgc ttgacatcat gaagtccatc tatgacatga tgggcaagta cacgtaccct    600
gcactccggg aggaggcccc aagggaacac gtggagagct tcttccagaa gatggacaga    660
aacaaggatg gtgtggtgac cattgaggaa ttcattgagt cttgtcaaaa ggatgagaac    720
atcatgaggt ccatgcagct ctttgacaat gtcatctag                           759
```

<210> SEQ ID NO 16
<211> LENGTH: 2733
<212> TYPE: DNA
<213> ORGANISM: Rattus norvegicus
<220> FEATURE:
<221> NAME/KEY: gene
<222> LOCATION: (1)..(2733)
<223> OTHER INFORMATION: hyperpolarization-activated, cyclic nucleotide-gated potassium channel 1 HCN1. (Accession: NM 053375)

<400> SEQUENCE: 16

```
atggaaggcg gcggcaagcc caactccgct tccaacagcc gcgacgatgg caacagcgtc    60 taccccctcca aggcgcccgc gacggggccg cggcggccg acaagcgcct ggggaccccg    120
ccggggggcg gcgcggccgg gaaggaacac ggcaactccg tgtgcttcaa ggtggacggc    180
```

```
ggcggaggag aggagccggc gggcagcttc gaggatgccg aggggccccg gcgacagtac    240
ggtttcatgc agaggcagtt cacctccatg ctgcagcctg ggtcaacaa attctccctc     300 cgcatgttcg ggagccagaa ggcggtggag aaggagcagg aaagggttaa aactgcaggc    360
ttctggatta tccatccgta cagtgacttc aggttttatt gggatttaat aatgcttata    420
atgatggttg gaaatttggt catcatacca gttggaatca cattcttcac agagcaaaca    480
acaacaccgt ggattatttt caatgtggca tcagatacag ttttcctgtt ggacctaatc    540 atgaattta ggactgggac tgtcaacgaa dacagctctg aaatcatcct ggaccctaaa     600
gtaatcaaga tgaattattt aaaaagctgg ttcgtggtgg acttcatctc ctcgatcccg    660
gtggattata tctttcttat tgtagagaaa ggaatggatt cggaagttta caagaccgcc    720
agagcacttc ggatcgtgag gtttacaaaa attctcagtc tcttgcgttt attacgcctt    780
tcaaggttaa ttagatacat acaccagtgg gaagagatat tccacatgac atatgatctc    840
gccagtgcag tggtgagaat cttcaacctc attggcatga tgctgctcct gtgtcactgg    900
gatggctgtc ttcagtttct ggtccccctg ctgcaggact tcccaccgga ttgctgggtt    960
tctctaaatg aaatggttaa tgattcatgg gggaaacagt attcctacgc actcttcaaa   1020
gctatgagtc acatgctgtg cattggttat ggcgcccagg cccccgtcag catgtctgac   1080
ctctggatta ccatgctgag catgattgtt ggggccacct gctatgccat gtttgtcggc   1140
catgccacag ctttgatcca gtctctggat tcttcaagga ggcagtatca agagaagtac   1200
aagcaagtag agcaatacat gtcattccac aagttaccag ctgacatgcg ccagaagata   1260
catgattact atgagcaccg ataccaaggc aagatcttcg atgaggaaaa tattctcagt   1320
gaacttaatg atcctctgag agaggaaata gtcaacttca actgccggaa actggtggcc   1380
accatgcctc tctttgctaa cgcggatccc aatttcgtga cggccatgct gagcaagctg   1440
agatttgagg tgttccagcc cggagactat atcattcgag aaggagctgt ggggaagaaa   1500
atgtatttca tccagcatgg tgtggctggt gtcatcacca agtccagtaa agaaatgaag   1560
ttgacagacg gctcttactt tggagaaata tgcctgctga ccaagggccg cgcactgcc    1620 agtgttcgag ctgatacata ctgtcgcctt tactcccttt cggtggacaa tttcaacgag   1680
gtcttggagg aatatccaat gatgagaaga gcctttgaga cagttgctat tgaccgacta   1740
gatcggatag gcaagaaaaa ctctattctc ctgcagaagt tccagaagga tctgaacact   1800
ggtgttttca caaccagga gaatgagatc ctgaagcaga ttgtgaagca tgacagagag    1860
atggtacaag cgatccctcc aatcaactat cctcaaatga cagccctgaa ttgcacatct   1920
tcaaccacca ccccaacgtc gcgcatgagg acccaatctc caccagtcta cacagcgacc   1980
agcctctctc acagcaacct gcactcaccc agccccagca cacagacgcc tcaaccctca   2040 gccatcctt cacccctgctc ctacaccaca gcagtctgca gtcctcctat acagagcccc   2100
ctggccacgc gaacttttcca ttatgcctct cccactgcat cccaattgtc actcatgcag   2160
cagcctcagc cgcagctaca gcaatcccag gtacagcaga ctcagactca gactcagcag   2220
cagcagcagc aacagcagcc gcagccgcag ccgcagcagc cgcaacagca acaacagcag   2280
caacagcagc agcagcagca gcagcaacaa cagcagcagc aacagccaca gacacctggt   2340
agttccacac cgaaaaatga agtgcacaag agcactcaag ctcttcataa caccacctg    2400 accagagaag tcaggcccct ctctgcctcg cagccttcgc tgcccatga ggtctccact     2460 atgatctcca gaccgcatcc cactgtgggc gagtccctgg cttccatccc tcaacccgtg   2520
```

-continued

| | |
|---|---|
| gcaacagtcc acagcactgg ccttcaggca gggagcagga gcaccgtgcc acagcgtgtc | 2580 |
| accttgttca gacagatgtc ctcgggagcc attcccccca accgaggagt gcctccagca | 2640 |
| cccccgccac cagcagctgt gcagagagag tctccctcag tcttaaataa agacccagat | 2700 |
| gcagaaaaac cccgttttgc ttcgaattta tga | 2733 |

<210> SEQ ID NO 17
<211> LENGTH: 2871
<212> TYPE: DNA
<213> ORGANISM: Rattus norvegicus
<220> FEATURE:
<221> NAME/KEY: gene
<222> LOCATION: (1)..(2871)
<223> OTHER INFORMATION: hyperpolarization activated cyclic
      nucleotide-gated potassium channel 2 (Norway Rat) HCN2 (Accession:
      XM 343170)
<220> FEATURE:
<221> NAME/KEY: misc_feature
<222> LOCATION: (306)..(355)
<223> OTHER INFORMATION: n is a, c, g, or t

<400> SEQUENCE: 17

| | |
|---|---|
| atggcagccc tgagccagtc acttactgaa tatcgagaaa aaataaaaaa cccactgaag | 60 |
| cagggtgaac atgaaagatc ccccttcatc tggaacaggc atgtgccctg ggtggggaca | 120 |
| caatctggca ctgtcaactg taatgttcaa aagtggaaac cagaggggtg ccaggggcag | 180 |
| ctccggagtc cccagggtca gggcagccca tctgtgtcag atgaggacat gcagctggca | 240 |
| aggcacatcc aacaccatgg aacacctact ggtgggggtg gctcaggtgg aggcggggct | 300 |
| cccgcnnnnn nnnnnnnnnn nnnnnnnnnn nnnnnnnnnn nnnnnnnnnn nnnnncgccg | 360 |
| ccgcccgcgc ccctcagccc tcagccacca cccgcgccac cccgaaccc cacgaccccc | 420 |
| tcgcacccga gtcggcgga cgagcccggc ccgcgctccc ggctctgcag ccgcgacagc | 480 |
| tcctgcactc ctggcgcggc caagggcggc gcgaatggcg agtgcgggcg cggggagccg | 540 |
| cagtgcagcc ccgagggccc ccgcgcggcg cccaaggttt cgttctcatg tcgcggggcg | 600 |
| gcctcggggc ccgcggcggc cgaggaggcg ggcagcgagg aggcgggccc ggcgggtgag | 660 |
| ccgcgcggca gccaggccag cttcctgcag cgccaattcg gggcgctcct gcagccgggc | 720 |
| gtcaacaagt tctccctgcg gatgtttggc agccagaagg ccgtggagcg cgagcaggaa | 780 |
| cgcgtgaagt cggcggggc ctggatcatc caccccctaca gcgacttcag gttctactgg | 840 |
| gacttcacca tgctgttgtt catggtggga atctcatca tcatccctgt gggcatcact | 900 |
| ttcttcaagg acgagaccac ggcgccctgg atcgtcttca cgtggtctc ggacacttc | 960 |
| ttcctcatgg acttggtgct gaactttcgc accggcattg ttattgagga caacacggag | 1020 |
| atcatcctgg accccgaaaa gataaagaaa agtacctgc gtacgtggtt cgtggtagac | 1080 |
| ttcgtgtcat ccatcccggt ggactacatc ttcctcatcg tggagaaggg aatcgactcc | 1140 |
| gaggtctaca agacgcccg tgcactacg atcgtgcgtt tcaccaagat cctcagtctg | 1200 |
| ctgcggttgc tgcggctatc ccggctcatc cgatatatcc accaatggga ggagattttc | 1260 |
| cacatgacct acgacctggc aagcgcggtg atgcgcatct gtaacctgat cagcatgatg | 1320 |
| ctgctgctct gccactggga cggctgcctg cagttcctgg tgcccatgct gcaagacttc | 1380 |
| cccagcgact gctgggtgtc catcaacaac atggtgaacc actcgtggag cgaactctat | 1440 |
| tcgttcgcgc tcttcaaggc catgagccac atgctctgta ttggctacgg gcggcaggct | 1500 |
| cccgagagca tgacggacat ctggctcacc atgctcagca tgatcgtggg cgccacctgc | 1560 |
| tacgctatgt tcattgggca cgccacggcg cttatccagt ccctggactc gtcacggcgc | 1620 |

```
cagtaccagg agaagtacaa gcaagtggag cagtacatgt ccttccacaa actgccggct    1680
gacttccgcc agaagatcca cgattactat gaacaccggt accaggggaa gatgtttgac    1740
gaggacagca tcctggggga actcaacggc ccactgcgtg aggagattgt gaacttcaac    1800
tgccggaagc tggtggcttc catgccgttg tttgccaacg cagaccccaa cttcgtcacc    1860
gccatgctga caaagctcaa atttgaggtc ttccagcctg agactacat catccgagag    1920 gggaccatcg ggaagaagat gtacttcatc cagcacgggg tggtgagcgt gctcaccaag    1980
ggcaacaagg agatgaagct gtcagatggc tcctattttg gggagatctg cctgctcacg    2040
aggggccggc gcacagccag tgtgcgggct gacacctact gtcgcctcta ctcactgagc    2100
gtggacaact tcaacgaggt gctggaggag taccccatga tgcggcgtgc ctttgagacc    2160
gtggccattg accgcctgga ccgcataggc aagaagaact ccatcttgct acacaaggtt    2220
cagcatgatc tcagctcggg tgtgttcaac aaccaggaga acgccatcat ccaggagatt    2280
gtcaaatatg accgtgagat ggtgcagcag gcagagctgg ccagcgtgt ggggctcttc    2340 ccaccaccgc caccaccgca ggtcacgtcg gccatcgcca cgctgcagca ggccgtggcc    2400
atgagcttct gcccgcaggt ggcccgcccg ctcgtggggc cctggcgct agggtcccca    2460 cgcctcgtgc gccgcgcgcc cccagggcct ctgcctcctg cagcctcacc agggccaccc    2520
gcagcgagcc ccccggctgc accctcgagc cctcggcac cgcggacctc acctacggt    2580 gtgcctggct ctccggcaac gcgtgtgggg cccgcattgc ccgcacgccg cctgagccgc    2640
gcctcgcgcc cactgtccgc ctcgcagccc tcgctgcccc acggcgcgcc cgcacccagc    2700
cccgcggcct ctgcgcgccc ggccagcagc tccacccgc gtctgggacc cgcacccacc    2760
acccggaccg cggcacccag tccggaccgc agggactcag cctcgccggg cgctgccagt    2820
ggcctcgacc cactggactc tgcgcgctcg cgcctctctt ccaacttgtg a              2871
```

<210> SEQ ID NO 18
<211> LENGTH: 2343
<212> TYPE: DNA
<213> ORGANISM: Rattus norvegicus
<220> FEATURE:
<221> NAME/KEY: gene
<222> LOCATION: (1)..(2343)
<223> OTHER INFORMATION: hyperpolarization-activated, cyclic
      nucleotide-gated potassium channel 3 (Norway Rat) HCN3 (Accession:
      NM 053685)

<400> SEQUENCE: 18

```
atggaggagg aggcgcggcc ggcggtgggg gacggggaag cggcgactcc tgcacgcgag     60
acgcctcctg cggctcccgc ccaggcccgc gcggcctcag gtggggtgcc agagtctgcg    120
cccgagccga agaggcggca gctcgggacg ctgctgcagc cgaccgtcaa caagttctct    180
ctccgggtct tcggcagcca caagcggtg gaaatcgagc aggagagggt gaagtccgcc    240
ggggcctgga tcatccaccc ctacagcgac ttccggtttt actggacct gatcatgctg    300 ctgctgatgg tggggaacct catagtactg cccgtgggca tcactttctt caaggaggag    360 aactcccccac cctggatcgt cttcaatgtc ctctcggaca ctttcttcct gctggatctg    420
gtgctcaact tccgaactgg catcgtggtg gaggaaggtg cggagatcct gttggcgccc    480
agggctatcc gcacgcgtta cctgcgcacc tggttcctgg tggacctgat ttcctccatc    540
cctgtggatt acatcttcct agtggtagag ctggagccac gactgagcgc tgaggtctac    600
aaaacggcac gggccctgcg catcgttaga ttcaccaaga tccttagcct gctgcggctg    660
```

-continued

| | |
|---|---|
| ctccgcctct cccgcctcat ccgatacatg caccagtggg aggagatctt tcacatgacc | 720 |
| tacgacctgg ccagtgcagt ggttcgcatc ttcaacctca ttggaatgat gttgctgctg | 780 |
| tgtcactggg atggctgtct gcagttcctg gtccctatgc tgcaggactt cccttccgac | 840 |
| tgctgggtct ccatgaaccg catggtgaac cactcgtggg gccgccagta ctcccacgcc | 900 |
| ctgttcaagg ccatgagtca catgctgtgc attggctacg gcagcaggc accagtaggc | 960 |
| atgcctgacg tctggctcac catgctcagc atgattgtgg gcgccacctg ctatgccatg | 1020 |
| ttcatcggcc acgccaccgc cctcatccag tccctggact cgtcccggcg ccagtaccag | 1080 |
| gagaagtaca agcaggtgga gcagtacatg tccttccaca agctgccagc cgacacacgg | 1140 |
| cagcgcatcc acgagtacta cgagcatcgg taccaggca agatgttcga tgaagagagc | 1200 |
| atcctggggg agctgagcga gccgcttcgg gaggagatta ttaacttcac ctgccggggc | 1260 |
| ctggtggccc acatgccgct gtttgctcat gctgacccca gtttcgtcac cgcagtactc | 1320 |
| accaagctcc gttttgaggt cttccaacct ggggatctgg tggtgcgtga gggctccgtg | 1380 |
| ggcaggaaga tgtacttcat ccagcatggg ctgctcagtg tgttggcacg gggcgcccgg | 1440 |
| gacactcgcc tcactgacgg atcctacttt ggggagatct gcctgctgac tcgaggtcgg | 1500 |
| agaacagcca gtgtaagggc tgacacctac tgtcgcctct actcactcag cgtggaccac | 1560 |
| ttcaatgcag tgcttgagga gttcccgatg atgcgcaggg cttttgagac tgtggccatg | 1620 |
| gaccggcttc ggcgcatcgg caaaaagaat tcgatattgc agcggaaacg ctctgagccg | 1680 |
| agtccaggca gcagcagtgg tggcgtcatg gagcagcatt tggtacaaca cgacagagac | 1740 |
| atggctcgtg gtattcgggg tctggctccg ggcacaggag ctcgcctcag tggaaagcca | 1800 |
| gtgctgtggg aaccactggt acacgcacct ctgcaggcag ctgctgtgac ctccaacgtg | 1860 |
| gccatagcct tgactcatca gcgaggccct ctgcccctct cccctgattc tccagccacc | 1920 |
| ctcctggctc gatctgctag acgctcagca ggctccccag cctccccact ggtgcctgtc | 1980 |
| cgagcaggtc ctctgctggc ccggggaccc tgggcgtcca cttctcgcct gcctgctcca | 2040 |
| cctgcccgaa ccctccatgc cagcctatcc ggacagggc gttcccaggt gtctctgttg | 2100 |
| ggccctcccc caggaggagg tggtcggagg ctaggacctc ggggccgccc actctctgcc | 2160 |
| tctcaaccct ctctgcctca gcgagccacg ggggatggct ctcctaggcg caaaggctct | 2220 |
| ggaagtgagc gtctgccccc ctcggggctc ctggccaagc ctccagggac tgtccagcca | 2280 |
| tccaggtcat cagtgcctga ccagttacc cccagaggtc cccaaatttc tgccaacatg | 2340 |
| tga | 2343 |

<210> SEQ ID NO 19
<211> LENGTH: 3597
<212> TYPE: DNA
<213> ORGANISM: Rattus norvegicus
<220> FEATURE:
<221> NAME/KEY: gene
<222> LOCATION: (1)..(3597)
<223> OTHER INFORMATION: hyperpolarization-activated, cyclic
      nucleotide-gated K+ 4 (Norway Rat) HCN4 (Accession: NM 021658)

<400> SEQUENCE: 19

| | |
|---|---|
| atggacaagc tgccgccgtc catgcgcaag cggctctaca gccttccgca gcaggtgggg | 60 |
| gccaaggcgt ggatcatgga cgaggaagag gatggtgagg aagaggggc ggggggcctc | 120 |
| caggacccaa gccgaaggag cattcggctg cggccgctgc cctcgccctc gcctcggtg | 180 |
| gccgccggct gctccgagtc ccggggtgcg gccctcgggg cggcagacag cgaggggccg | 240 |

```
ggccgcagcg ccggcaagtc cagcaccaac ggtgactgca ggcgcttccg cgggagtctg      300
gcctcgctgg gcagccgggg cggcggcagt ggtggagcag ggggcggcag cagtctcggg      360
cacctgcatg actccgcgga ggagcggcgg ctcatcgccg ctgagggcga tgcgtccccc      420
ggcgaggaca ggacgccccc gggcctggcg accgagcccg agcgcccggg cgccgcggca      480
caacccgcag cctcgccgcc gccccaacag ccgccgcagc cggcctccgc ctcctgcgag      540
cagccctcgg cggacacagc tatcaaagtg gaaggaggcg cggccgccag cgaccagatc      600
ctccctgagg ccgaggtgcg cctgggccag agcggcttca tgcagcgcca gttcggtgcc      660
atgctgcaac ctggggtcaa caaattctcg ctaaggatgt tcggcagcca gaaagcagtg      720
gagcgtgagc aggagagggt taagtcagct gggttttgga ttatccaccc ctacagcgac      780
ttcagatttt actgggacct gacgatgctg ttgctgatgg tggggaatct gatcatcatc      840
cctgtgggca tcaccttctt caaggatgag aacaccaccc cctggatcgt cttcaacgtg      900
gtgtcagaca cattcttcct cattgacttg gtcctcaact tccgcacggg gatcgtggtg      960
gaggacaaca cagaaatcat ccttgaccca cagcggatca agatgaagta cctgaaaagc     1020
tggtttgtgg tggacttcat ctcctccatc cccgtggact acatcttcct tatagtggag     1080
actcgcattg actcggaggt ctacaaaacc gccaggctc tgcgcattgt ccgcttcacg     1140
aagatcctca gcctcctgcg cctcctgcgg ctttcccgcc tcattcggta cattcaccag     1200
tgggaagaga tcttccacat gacctacgac ctggccagtg ccgtggtacg catcgtgaac     1260
ctcattggca tgatgcttct gctttgccac tgggatggct gcctgcagtt cctggtgccc     1320
atgctgcagg acttccccca tgactgctgg gtgtccatca acggcatggt gaataactcc     1380
tgggggaagc agtactccta tgccctcttc aaggccatga gccacatgct gtgtattggg     1440 tacgacggc aggcacccgt aggcatgtct gacgtctggc tcaccatgct cagcatgatc     1500
gtgggcgcca cctgctatgc catgttcatc gggcacgcca ctgccctcat ccagtcgctg     1560
gactcctccc ggcgccagta ccaggagaag tacaagcagg tggagcagta catgtccttc     1620
cacaagctcc cgcctgacac caggcagcgc atccacgact actacgaaca ccgctaccag     1680
ggcaagatgt ttgacgagga aagcatcctg ggtgagctga gtgagccgct tcgagaggag     1740
atcatcaact ttaactgccg gaagctggtg gcatccatgc cactgttcgc caatgcagac     1800
cccaactttg tgacgtctat gctgaccaag ttgcgttttg aggtctttca gcctggggac     1860
tacatcatcc gtgaaggcac catcggcaag aagatgtact ttatccagca cggcgtggtc     1920
agtgtgctca ctaagggcaa caaggagacc aagctggctg atggctccta ttttggagag     1980
atctgcttgc tgacccgagg ccgtcgcaca gcgagcgtga gggcggatac ttactgccgc     2040
ctctactcac tgagcgtgga caacttcaac gaggtgctgg aggagtatcc catgatgcgc     2100
agggctttcg agacggttgc gctggaccgt ctggaccgca taggcaagaa gaactccatc     2160
ctcctccaca aggtgcagca cgacctcaac tcaggcgtct tcaactacca agagaacgag     2220
atcatccagc agatcgtgcg gcatgaccgt gagatggccc actgtgctca ccgcgtccag     2280
gctgctgcct cagccacccc aacccaacg cctgtcatat ggaccccact gatccaggca     2340
ccactgcagg ctgctgctgc tactacttcg gtggccatag ccctcacaca ccaccccgc      2400 ctgccagccg ctatcttccg gccccctccc ggacctgggc tgggtaacct gggggctgga     2460
cagacaccga ggcacccaag gaggttgcag tccttgatcc cttcagcgct aggctctgct     2520
tcaccagcca gcagccccctc acaggtggac acaccgtctt catcttcctt ccacatccaa     2580
cagctggctg gattctctgc acctcctgga ttgagtcctc tcttgccctc ctctagctct     2640
```

-continued

```
tccccacctc caggagcctg cagttctccc ccagccccca ctccatccac ctccactgct    2700
gccaccacca ccgggttcgg ccactttcat aaggcgctag gtggctccct gtcttcctct    2760
gattccccgc tgctcacccc actgcaaccg ggcgctcgct ctccacaggc tgcccagccg    2820 ccaccccac tgcctggggc ccgaggaggc ctgggactcc tggagcactt cttgccgccc     2880
ccaccttcgt cccggtcacc atcatctagc cctgggcagc tgggccagcc tcctggagag    2940
ttgtccccag gtctggcagc tggtccacca agtacaccag agacaccccc gcggcccgaa    3000
cggccatcct ttatggcagg ggcctctggg ggggcttctc ctgtagcctt tacccccga    3060 ggaggcctca gccctccggg ccacagccca ggaccccaa gaactttccc gagtgcccca    3120
ccccgggcct ctggctccca tggttccctg ctcctgccac ctgcatccag ccctccgcct    3180
ccccaggtcc cacagcgcag gggcacacca ccctcaccc ccggccgcct cacacaggac    3240
ctgaagctca tctcagcctc tcagccagcc ctcccccagg atggggcaca gactctacgc    3300
agggcctctc ctcactcctc aggggagtcg atggctgcct tctcactcta ccccagagct    3360
gggggtggca gtgggagcag tggggccctt gggcctcctg gaaggccata tggtgccatc    3420
ccaggccagc atgtcacttt gcctcggaag acatcctcag gttctttgcc accccacttt    3480
tctttgtttg gggcaagagc cgcctcttct ggagggcccc ctctgactgc tgcacccag    3540 agggaacctg cgctaggtc cgagccagta cgctccaaac tgccgtctaa tttatga      3597
```

<210> SEQ ID NO 20
<211> LENGTH: 2733
<212> TYPE: DNA
<213> ORGANISM: Mus musculus
<220> FEATURE:
<221> NAME/KEY: gene
<222> LOCATION: (1)..(2733)
<223> OTHER INFORMATION: hyperpolarization-activated, cyclic
      nucleotide-gated K+ 1 (house mouse) HCN1 (Accession: NM 010408)

<400> SEQUENCE: 20

```
atggaaggcg gcggcaaacc caactccgcg tccaacagcc gcgacgatgg caacagcgtc    60
ttcccctcca aggcgcccgc gacggggccg gtggcggccg acaagcgcct ggggaccccg    120
ccgaggggcg gcgcggccgg gaaggaacat ggcaactccg tgtgcttcaa ggtggacggc    180
ggcggaggag aggagccggc gggcagcttc gaggatgccg aggggccccg gcggcagtat    240
ggtttcatgc agaggcagtt cacctccatg ctgcagcctg gggtcaacaa attctccctc    300
cgcatgtttg ggagccagaa gcggtggag aaggagcagg aaagggttaa aactgcaggc    360
ttctggatta tccatccgta cagtgacttc aggttttatt gggatttaat catgcttata    420
atgatggttg gaaatttggt catcatacca gttggaatca cgttcttcac agagcagacg    480
acaacaccgt ggattatttt caacgtggca tccgatactg ttttcctgtt ggacttaatc    540
atgaatttta ggactgggac tgtcaatgaa gacagctcgg aaatcatcct ggaccctaaa    600
gtgatcaaga tgaattattt aaaaagctgg tttgtggtgg acttcatctc atcgatcccg    660
gtggattata tctttctcat tgtagagaaa gggatggact cagaagttta caagacagcc    720
agagcacttc gtatcgtgag gtttacaaaa attctcagtc tcttgcggtt attacgcctt    780
tcaaggttaa tcagatacat acaccagtgg gaagagatat ccacatgac ctatgacctc    840 gccagtgctg tggtgaggat cttcaacctc attggcatga tgctgcttct gtgccactgg    900
gatggctgtc ttcagttcct ggttcccctg ctgcaggact cccaccagaa ttgctgggtt    960
tctctgaatg aaatggttaa tgattcctgg ggaaaacaat attcctacgc actcttcaaa    1020
```

```
gctatgagtc acatgctgtg cattggttat ggcgcccaag cccctgtcag catgtctgac    1080
ctctggatta ccatgctgag catgattgtg ggcgccacct gctacgcaat gtttgttggc    1140
catgccacag ctttgatcca gtctttggac tcttcaagga ggcagtatca agagaagtat    1200
aagcaagtag agcaatacat gtcattccac aagttaccag ctgacatgcg ccagaagata    1260
catgattact atgagcaccg ataccaaggc aagatcttcg atgaagaaaa tattctcagt    1320
gagcttaatg atcctctgag agaggaaata gtcaacttca actgccggaa actggtggct    1380
actatgcctc tttttgctaa cgccgatccc aatttcgtga cggccatgct gagcaagctg    1440
agatttgagg tgttccagcc cggagactat atcattcgag aaggagctgt ggggaagaaa    1500
atgtatttca tccagcacgg tgttgctggc gttatcacca agtccagtaa agaaatgaag    1560
ctgacagatg gctcttactt cggagagata tgcctgctga ccaagggccg cgcactgcc     1620 agtgtccgag ctgataccta ctgtcgtctt tactcccttt cggtggacaa tttcaatgag    1680
gtcttggagg aatatccaat gatgagaaga gcctttgaga cagttgctat tgaccgactc    1740
gatcggatag gcaagaaaaa ctctattctc ctgcagaagt tccagaagga tctaaacact    1800
ggtgttttca acaaccagga gaacgagatc ctgaagcaga tcgtgaagca tgaccgagag    1860
atggtacaag ctatccctcc aatcaactat cctcaaatga cagccctcaa ctgcacatct    1920
tcaaccacca ccccaacctc ccgcatgagg acccaatctc cgccagtcta caccgcaacc    1980
agcctgtctc acagcaatct gcactcaccc agtcccagca cacagacgcc ccaaccctca    2040
gccatccttt cacctgctc ctataccaca gcagtctgca gtcctcctat acagagcccc      2100
ctggccacac gaactttcca ttatgcctct cccactgcgt cccagctgtc actcatgcag    2160
cagcctcagc agcaactacc gcagtccag gtacagcaga ctcagactca gactcagcag      2220
cagcagcagc aacagcagca gcagcagcag cagcaacagc aacaacagca gcagcagcag    2280
cagcagcagc agcagcagca gcagcagcag cagcagcagc agcagccaca gacacctggt    2340
agctccacac cgaaaaatga agtgcacaag agcacacaag cccttcataa caccaacctg    2400
accaaagaag tcaggcccct ttccgcctcg cagccttctc tgccccatga ggtctccact    2460
ttgatctcca gacctcatcc cactgtgggc gaatccctgg cctctatccc tcaacccgtg    2520
gcagcagtcc acagcactgg ccttcaggca gggagcagga gcacagtgcc acaacgtgtc    2580
accttgttcc gacagatgtc ctcgggagcc atcccccca accgaggagt gcctccagca     2640 cccctccac cagcagctgt gcagagagag tctcccctcag tcctaaatac agacccagat    2700
gcagaaaaac cccgttttgc ttcgaattta tga                                 2733
```

<210> SEQ ID NO 21
<211> LENGTH: 2592
<212> TYPE: DNA
<213> ORGANISM: Mus musculus
<220> FEATURE:
<221> NAME/KEY: gene
<222> LOCATION: (1)..(2592)
<223> OTHER INFORMATION: hyperpolarization-activated, cyclic
      nucleotide-gated K+ 2 (House Mouse) HCN2 (Accession: NM 008226)

<400> SEQUENCE: 21

```
atggatgcgc gcgggggcgg cggcggccg ggcgatagtc cgggcacgac ccctgcgccg        60
gggccgccgc caccgccgcc gccgccgcg cccctcagc ctcagccacc acccgcgcca        120
cccccgaacc ccacgacccc ctcgcacccg gagtcggcgg acgagcccgg cccgcgcgcc      180
cggctctgca gccgcgacag cgcctgcacc cctggcgcgg ccaagggcgg cgcgaatggc      240
```

| | |
|---|---|
| gagtgcgggc gcggggagcc gcagtgcagc cccgagggcc ccgcgcgcgg ccccaaggtt | 300 |
| tcgttctcat gccgcggggc ggcctccggg ccctcggcgg ccgaggaggc gggcagcgag | 360 |
| gaggcgggcc cggcgggtga gccgcgcggc agccaggcta gcttcctgca gcgccaattc | 420 |
| ggggcgcttc tgcagcccgg cgtcaacaag ttctccctgc ggatgttcgg cagccagaag | 480 |
| gccgtggagc gcgagcagga acgcgtgaag tcggcggggg cctggatcat ccaccccstac | 540 |
| agcgacttca ggttctactg ggacttcacc atgctgttgt tcatggtggg aaatctcatt | 600 |
| atcattcccg tgggcatcac tttcttcaag gacgagacca ccgcgccctg atcgtcttc | 660 |
| aacgtggtct cggacacttt cttcctcatg gacttggtgt tgaacttccg caccggcatt | 720 |
| gttattgagg acaacacgga gatcatcctg accccgaga agataaagaa gaagtacttg | 780 |
| cgtacgtggt tcgtggtgga cttcgtgtca tccatcccgg tggactacat cttcctcata | 840 |
| gtggagaagg gaatcgactc cgaggtctac aagacagcgc gtgctctgcg catcgtgcgc | 900 |
| ttcaccaaga tcctcagtct gctgcggctg ctgcggctat cacggctcat ccgatatatc | 960 |
| caccagtggg aagagatttt ccacatgacc tacgacctgg caagtgcagt gatgcgcatc | 1020 |
| tgtaacctga tcagcatgat gctactgctc tgccactggg acggttgcct gcagttcctg | 1080 |
| gtgcccatgc tgcaagactt ccccagcgac tgctgggtgt ccatcaacaa catggtgaac | 1140 |
| cactcgtgga gcgagctcta ctcgttcgcg ctcttcaagg ccatgagcca catgctgtgc | 1200 |
| atcggctacg gcggcaggc gcccgagagc atgacagaca tctggctgac catgctcagc | 1260 |
| atgatcgtag gcgccacctg ctatgccatg ttcattgggc acgccactgc gctcatccag | 1320 |
| tccctggatt cgtcacggcg ccaataccag gagaagtaca agcaagtaga gcaatacatg | 1380 |
| tccttccaca aactgcccgc tgacttccgc cagaagatcc acgattacta tgaacaccgg | 1440 |
| taccaaggga agatgtttga tgaggacagc atccttgggg aactcaacgg gccactgcgt | 1500 |
| gaggagattg tgaacttcaa ctgccggaag ctggtggctt ccatgccgct gtttgccaat | 1560 |
| gcagacccca acttcgtcac agccatgctg acaaagctca aatttgaggt cttccagcct | 1620 |
| ggagattaca tcatccgaga ggggaccatc gggaagaaga tgtacttcat ccagcatggg | 1680 |
| gtggtgagcg tgctcaccaa gggcaacaag gagatgaagc tgtcggatgg ctcctatttc | 1740 |
| ggggagatct gcttgctcac gaggggccgg cgtacggcca gcgtgcgagc tgacacctac | 1800 |
| tgtcgcctct actcactgag tgtggacaat ttcaacgagg tgctggagga ataccccatg | 1860 |
| atgcggcgtg cctttgagac tgtggctatt gaccggctag atcgcatagg caagaagaac | 1920 |
| tccatcttgc tgcacaaggt tcagcatgat ctcagctcag gtgtgttcaa caaccaggag | 1980 |
| aatgccatca tccaggagat tgtcaaatat gaccgtgaga tggtgcagca ggcagagctt | 2040 |
| ggccagcgtg tgggctctt cccaccaccg ccaccaccgc aggtcacatc ggccattgcc | 2100 |
| accctacagc aggctgtggc catgagcttc tgcccgcagg tggcccgccc gctcgtgggg | 2160 |
| cccctggcgc taggctcccc acgcctagtg cgccgcgcgc cccagggcc tctgcctcct | 2220 |
| gcagcctcgc cagggccacc cgcagcaagc ccccggctg caccctcgag ccctcgggca | 2280 |
| ccgcggacct caccctacgg tgtgcctggc tctccggcaa cgcgcgtggg gcccgcattg | 2340 |
| cccgcacgtc gcctgagccg cgcctcgcgc ccactgtccg cctcgcagcc ctcgctgccc | 2400 |
| catggcgtgc ccgcgcccag ccccgcggcc tctgcgcgcc cggcagcag ctccacgccg | 2460 |
| cgcctgggac ccgcacccac cgcccggacc ccgcgcgccca gtccggaccg cagggactca | 2520 |
| gcctcgccgg gcgctgccag tggcctcgac ccactggact ctgcgcgctc gcgcctctct | 2580 | tccaacttgt ga                                                2592

<210> SEQ ID NO 22
<211> LENGTH: 2340
<212> TYPE: DNA
<213> ORGANISM: Mus musculus
<220> FEATURE:
<221> NAME/KEY: gene
<222> LOCATION: (1)..(2340)
<223> OTHER INFORMATION: hyperpolarization-activated, cyclic
      nucleotide-gated K+ 3 (House Mouse) HCN3 (Accession: NM 008227)

<400> SEQUENCE: 22

| | | | | | |
|---|---|---|---|---|---|
| atggaggagg | aggcgcggcc | ggcggcgggg | gccggcgaag | cggcgacccc | tgcacgcgag | 60 |
| acgcctcctg | cggctccggc | ccaggcccgc | gcggcctcag | gtggggtgcc | ggagtctgcg | 120 |
| cccgagccga | agaggcggca | gctcgggacg | ctgctgcagc | cgacggtcaa | caagttctct | 180 |
| ctccgggtct | tcggcagcca | caaagcagta | gaaatcgagc | aggagagggt | gaagtccgcc | 240 |
| ggggcctgga | tcatccaccc | ctacagcgac | ttccggtttt | actgggatct | catcatgctg | 300 |
| ctgctgatgg | tggggaacct | catagttctg | cctgtgggta | tcactttctt | caaggaggag | 360 |
| aactctccac | cctggatcgt | cttcaatgtc | ctctctgaca | ctttcttcct | gctggatctg | 420 |
| gtgctcaact | tccgaactgg | catcgtggtg | gaggaaggtg | ccgagatcct | gctggcgcca | 480 |
| agggccatcc | gaacgcgtta | cctgcgcacc | tggttcctgg | ttgatctgat | ctcctccatc | 540 |
| cctgtggatt | atatcttcct | agtggtggag | ctggagccac | gactagatgc | tgaggtctac | 600 |
| aaaacggcac | gggccctgcg | catcgttaga | ttcaccaaga | tccttagcct | gctgcggctg | 660 |
| ctccgcctct | cccgcctcat | ccgctacata | caccagtggg | aggagatctt | tcacatgacc | 720 |
| tacgacctgg | ccagtgcagt | ggttcgcatc | ttcaacctca | ttggaatgat | gttgctgctg | 780 |
| tgtcactggg | acggctgtct | gcagtttctg | gtccctatgc | tgcaggactt | cccgtccgac | 840 |
| tgctgggtct | ccatgaaccg | catggtgaac | cactcgtggg | gccgccagta | ttcccacgcc | 900 |
| ctgttcaagg | ccatgagtca | catgctatgc | attggctatg | ggcagcaggc | accggtaggc | 960 |
| atgcctgacg | tctggctcac | catgctcagt | atgattgtgg | gcgccacgtg | ttatgccatg | 1020 |
| ttcatcggtc | acgccaccgc | cctcatccag | tccctggact | cttcccggcg | acagtaccag | 1080 |
| gagaagtaca | agcaggtgga | gcagtacatg | tccttccaca | agctgcccgc | tgacacccgg | 1140 |
| cagcgcatcc | acgagtacta | cgagcatcgc | taccagggca | agatgtttga | tgaagagagc | 1200 |
| atcctggggg | agctgagcga | gccacttcgg | gaggagatta | ttaacttcac | ctgccggggc | 1260 |
| ctggtggccc | acatgccgct | gttttgctcat | gctgacccca | gcttcgtcac | cgcagtgctc | 1320 |
| accaagctcc | gttttgaggt | cttccaacca | ggggacctgg | tggtgcgtga | gggctccgtg | 1380 |
| ggcaggaaga | tgtacttcat | ccagcacggg | ctgctgagtg | tgctggcacg | tggcgcccgc | 1440 |
| gacacccgcc | tcactgatgg | atcctacttt | ggggagatct | gcctgctgac | tcgaggtcgg | 1500 |
| agaacagcca | gtgtaagggc | tgacacctat | tgtcgcctct | actcgctcag | cgtgaccac | 1560 |
| ttcaatgcgg | tgcttgagga | gttcccaatg | atgcgcaggg | cttttgagac | ggtggccatg | 1620 |
| gaccggcttc | ggcgcatcgg | caaaaagaat | tcgatactgc | agcggaaacg | ctctgagccg | 1680 |
| agtccaggca | gcagcgtgg | cgtcatggag | cagcatttgg | tacaacacga | cagagacatg | 1740 |
| gctcgtggtg | ttcggggcct | ggctcctggt | acaggagctc | gactcagtgg | aaagccagtg | 1800 |
| ctgtgggaac | cactggtgca | cgcccctctg | caggcagctg | ctgtgacctc | caacgtggcc | 1860 |
| atagccttga | ctcaccagcg | aggccctctg | cccctctccc | ctgattctcc | agccaccctc | 1920 |

| | | | | |
|---|---|---|---|---|
| ctagctcgat | ctgctagacg | ctcagcaggc | tccccagcct | ccccactggt gcctgtccga | 1980 |
| gcaggtcctc | tgctggcccg | gggaccctgg | gcgtccactt | ctcgcctgcc tgctccacct | 2040 |
| gcccgaaccc | tccatgccag | cctatcccgg | acagggcgtt | cccaggtatc tctgttgggc | 2100 |
| cctcccccag | gaggaggtgc | tcggaggcta | ggacctcggg | gccgcccact ttctgcctcg | 2160 |
| caaccctctc | tgcctcagcg | agcaacaggg | gatggctctc | ctaggcgtaa aggctctgga | 2220 |
| agtgagcgcc | tgccccccctc | tgggctcttg | gccaaacctc | cagggacagt ccagccaccc | 2280 |
| aggtcatcag | tgcctgagcc | agttaccccc | agaggtcccc | aaatttctgc caacatgtga | 2340 |

<210> SEQ ID NO 23
<211> LENGTH: 3606
<212> TYPE: DNA
<213> ORGANISM: Mus musculus
<220> FEATURE:
<221> NAME/KEY: gene
<222> LOCATION: (1)..(3606)
<223> OTHER INFORMATION: similar to hyperpolarization-activated, cyclic
    nucleotide-gated K+ 4; hyperpolarization-activated, cyclic
    nucleotide-gated potassium channel 4 (House Mouse) HCN4
    (Accession: XM 287905)

<400> SEQUENCE: 23

| | | | | |
|---|---|---|---|---|
| atggacaagc | tgccgccgtc | catgcgcaag | cggctctaca | gccttccgca gcaggtgggg | 60 |
| gccaaggcgt | ggatcatgga | cgaggaagag | gatggtgagg | aagaaggggc cggggccgc | 120 |
| caggacccca | gccgaaggag | catccggctg | cggccgctgc | cctcgccctc tccctcggtg | 180 |
| gctgcgggct | gctcggagtc | ccggggtgcg | gccctcgggg | cgacagagag cgaggggccg | 240 |
| ggccgcagcg | ccggcaagtc | cagcaccaac | ggtgactgca | ggcgcttccg cgggagtctg | 300 |
| gcctcgctgg | gcagccgggg | cggcggcagt | ggtggagcag | gggcggcag cagtctcggg | 360 |
| cacctgcatg | actccgcgga | ggaacggcgg | ctcatcgccg | ctgagggcga tgcgtccccc | 420 |
| ggcgaggaca | ggacgccccc | gggcctggcg | accgaacccg | agcgcccggc caccgcggca | 480 |
| caacccgcag | cctcgccgcc | gccccagcag | ccgccgcagc | cggcctctgc ctcctgcgag | 540 |
| cagcccctcgg | cggacaccgc | tatcaaagtg | gagggaggcg | cggccgccag cgaccagatc | 600 |
| ctccccgagg | ccgaggtgcg | cctgggccag | agcggcttca | tgcagcgcca gttcggtgcc | 660 |
| atgctgcaac | tgggggtcaa | caaattctcc | ctaaggatgt | tcggcagcca gaaagcggtg | 720 |
| gagcgcgagc | aggagagggt | taagtcagca | gggttttgga | ttatccaccc ctacagtgac | 780 |
| ttcagatttt | actgggacct | gacgatgctg | ttgctgatgg | tggggaatct gatcatcata | 840 |
| cccgtgggca | tcaccttctt | caaggatgag | aacaccacac | cctggatcgt cttcaatgtg | 900 |
| gtgtcagaca | cattcttcct | cattgacttg | gtcctcaact | tccgcacggg gatcgtggtg | 960 |
| gaggacaaca | cagaaatcat | ccttgacccg | cagaggatca | agatgaagta cctgaaaagc | 1020 |
| tggtttgtgg | tagatttcat | ctcctccatc | cctgtcgact | acatcttcct tatagtggag | 1080 |
| actcgcattg | actcggaggt | ctacaaaacc | gctagggctc | tgcgcattgt ccgtttcact | 1140 |
| aagatcctca | gcctcctgcg | cctcttgagg | cttttcccgcc | tcattcgata cattcatcag | 1200 |
| tgggaagaga | tcttccacat | gacctatgac | ctggccagcg | ccgtggtacg catcgtgaac | 1260 |
| ctcattggca | tgatgcttct | gctgtgtcac | tgggatggcc | gcctgcagtt cctagtgccc | 1320 |
| atgctgcagg | acttcccccca | tgactgctgg | gtgtccatca | atggcatggt gaataactcc | 1380 |
| tgggggaagc | agtattccta | cgccctcttc | aaggccatga | gccacatgct gtgcattggg | 1440 |
| tatggacggc | aggcacccgt | aggcatgtct | gacgtctggg | tcaccatgct cagcatgatc | 1500 |

```
gtgggggcca cctgctatgc catgttcatc ggccacgcca ctgccctcat ccagtcgcta    1560
gactcctccc ggcgccagta ccaggagaag tataaacagg tggagcagta catgtccttc    1620
cacaagctcc cgcctgacac ccgacagcgc atccatgact actatgaaca ccgctaccaa    1680
ggcaagatgt ttgatgagga aagcatcctg ggtgagctga gtgagccact tcgagaggag    1740
atcatcaact ttaactgccg aaagctggtg gcatccatgc cactgtttgc caacgcagat    1800
cccaactttg tgacatccat gctgaccaag ttgcgtttcg aggtcttcca gcctggggat    1860
tacatcatcc gcgaaggcac catcggcaag aagatgtact ttatccagca cggcgtggtc    1920
agcgtgctca ctaagggcaa caaagagacc aagctggctg atggctccta ttttggagag    1980
atctgcttgc tgacccgggg tcggcgcaca gccagcgtca gagcggatac ttattgccgc    2040
ctctactcac tgagcgtgga caacttcaat gaggtgctgg aggagtatcc catgatgcgg    2100
agggccttcg agacggttgc gctggaccgc ctggaccgca taggcaagaa gaactccatc    2160
ctcctccaca aggtgcagca cgacctcaac tcaggcgtct tcaactacca agagaacgag    2220
atcatccagc agatcgtgcg gcatgaccgt gagatggccc actgtgctca ccgcgtccag    2280
gctgccgcct cagccacccc aaccccccacg cctgttatat ggaccccgct gatccaggcg    2340
ccactgcagg ctgctgctgc tactacttcg gtggccatag ccctcacaca ccaccccgc    2400 ctgcccgccg ccatcttccg gccccctccc ggacctgggc tgggcaacct tggggctgga    2460
cagacaccga ggcacccaag gaggctgcag tccttgatcc cttcagctct gggctctgct    2520
tcacccgcca gcagcccctc acaggtggac acaccgtctt catcctcctt ccacatccaa    2580
cagctggctg gattctctgc acctcctgga ttgagccctc cctgccctc ctctagctct    2640 tccccacctc caggagcctg cggttcccca ccagccccca caccctccac ctccactgcc    2700
gccgccgcct ccaccactgg gttcggccac tttcacaagg cgctgggtgg ctccctgtca    2760
tcctctgact ccccgctgct caccccactg caaccaggcg ctcgctctcc acaggctgcc    2820
cagccaccac ccccactgcc tggggcccga ggaggtctgg gactcctgga gcacttcttg    2880
ccgcccccac cctcctccag gtcaccatca tccagccctg ggcagctggg ccagcctcct    2940
ggagagttgt ccctaggtct ggcagctggt ccatcaagta caccagagac accccacgg    3000 cctgagcgac catccttcat ggcaggggcc tctggagggg cttctcctgt agcctttacc    3060
ccccgaggag gcctcagtcc tccgggccac agcccggggc ccccaagaac tttcccgagt    3120
gccccacccc gggcctctgg ctcccatggt tccctgctcc tgccacctgc atccagccct    3180
ccacctcccc aggtcccaca gcgcagggc acaccacccc tcacccctgg ccgcctcaca    3240
caggacctga agctcatctc agcctctcag ccagccctcc cccaggatgg ggcacagact    3300
ctccgcaggg cctcgcctca ctcctcaggg gagtcggtgg ctgccttctc actctacccc    3360
agagctgggg gtggcagtgg gagtagtggg ggccttgggc ctcctggaag gccatatggt    3420
gccatcccag gccaacatgt cactttgcct cggaagacat cctcaggttc tttgccaccc    3480
ccactttctt tgtttggggc aagagccgcc tcttctggag ggccccctct gactactgct    3540
gcaccccaga gggaacctgg cgctaggtct gagccagtac gctccaaact gccgtctaat    3600
ttatga                                                              3606
```

<210> SEQ ID NO 24
<211> LENGTH: 2469
<212> TYPE: DNA
<213> ORGANISM: Oryctolagus cuniculus
<220> FEATURE:
<221> NAME/KEY: gene
<222> LOCATION: (1)..(2469)
<223> OTHER INFORMATION: uORF and hyperpolarization-activated cyclic
nucleotide-gated channel 1 (Rabbit) HCN1 (Accession: AF 168122)

<400> SEQUENCE: 24

```
atggcaacag cgtcttcccc gccaaggcgc ccgcgacggg cgcggggcct ggaggacgct      60
gaggggccgc ggcggcagta cggcttcatg cagcgacagt tcacctccat gctgcagccc     120
ggggtcaaca aattctccct ccgcatgttc gggagccaga aggcggtgga gaaggagcag     180
gaaagggtta aaactgcagg cttctggatt atccacccct acagcgattt caggttttat     240
tgggatttaa taatgcttat aatgatggtt ggaaatctag tcatcatacc agttggaatc     300
acattcttta cagaacagac aacaacacca tggattattt tcaatgtggc atcagataca     360
gttttttctat tggacttgat catgaatttt aggactggga ctgtcaatga agacagttct     420
gaaatcatcc tggaccctaa agtaatcaag atgaattatt taaaaagctg gtttgtggtt     480
gacttcatct catcaatccc agtggattat atctttctta ttgtagaaaa aggaatggat     540
tcagaagttt acaagacagc cagggcactt cgcattgtga ggtttacaaa aattctcagt     600
ctcttgcgtt tattacgact ttcaagatta attagataca tacatcagtg gaagagata      660
tttcatatga cgtatgatct tgccagtgcg gtggtgagga ttttttaatct catcggcatg     720
atgctgctct tgtgtcactg ggatggttgt ctgcagttct tggtcccact attgcaggat     780
ttcccaccag attgctgggt gtccctcaat gaaatggtta atgattcctg gggaaagcag     840
tattcatacg cgctcttcaa agctatgagt cacatgctgt gcattgggta tggagcccaa     900
gccccagtca gcatgtctga cctctggatt accatgttga catgattgt cggggccacc      960
tgctacgcca tgtttgttgg ccatgccact gctttaatcc aatctttgga ttcttcaagg    1020
cggcagtatc aagagaagta taagcaagta gaacaataca tgtcattcca taagttacca    1080
gctgatatgc gtcagaagat acatgattac tatgaacaca gatatcaagg caaaatcttt    1140
gatgaggaaa atattctcaa tgaactgaat gatcctctga gagaggagat agtcaacttc    1200
aactgtcgga aactagtggc tacaatgcct ctttttgcta acgcagatcc gaattttgtg    1260
actgccatgc tgagcaagtt gagatttgag gtatttcaac ctggagatta tatcatacga    1320
gaaggagctg tagggaaaaa aatgtatttc attcagcatg tgtggcggg tgtcatcaca    1380
aagtcaagta agaaatgaa gctgacagat ggctcttact ttggagagat tgtttgctg     1440
actaaaggac gccgcacagc tagtgttcga gctgatacct attgtcgtct ttattcccctt   1500
tcggtggaca atttcaatga ggtcctggaa gaataccata tgatgagaag agcctttgag   1560
actgttgcta ttgaccgact agatcgaata ggaaagaaaa actccattct tctgcaaaag   1620
ttccagaagg atctgaacac tggtgttttt aacaaccagg agaatgagat cctgaagcag   1680
attgtgaaac atgacaggga gatggtgcag gcgatcgctc ccatcagtta tcctcaaatg   1740
acagccctga ttccaccctc gtccactgct accccgacct cacgcatgag gaccagtct    1800
ccaccggtgt acacagcaac cagcctgtct cacagcaacc tgcactcccc cagccccagc   1860
actcagaccc ccagccttc tgccatcctc tcgccctgct cctacaccac tgcggtctgc    1920
agtcctcctg tacagagccc gctggccact cgaactttcc actacgcctc ccccactgcc   1980
tcccagttgt cactcatgcc tcagcagcag cagcagcccc aggcacctca gactcagccg   2040
cagcagccgc cccagcagcc gcagacgccc ggcagcgcca cgccgaagaa cgaagtgcac   2100
cggagcacgc aggcgcttcc taataccagc ctgaccaggg aggtcaggcc cctgtccgcc   2160
tcgcagcctt cgctgccgca cgaggtttcc actctgatt ccagacctca tcccactgtg   2220
```

-continued

```
ggcgagtccc tggcctccat cccccagccc gtggcagctg tccacagcgc gggcctccag    2280
gcagcgggca ggagcactgt ccctcagcga gtcaccctgt ttcgacagat gtcctccgga    2340
gccattcccc ccaaccgagg agtgcctccg gcaccccctc caccagcagc cctcttcag     2400 agagaggctt cctcagtctt aaacacagac ccggaggcag aaaagccacg atttgcttcg    2460
aatttatga                                                            2469
```

<210> SEQ ID NO 25
<211> LENGTH: 2817
<212> TYPE: DNA
<213> ORGANISM: Oncorhynchus mykiss (Rainbow Trout)
<220> FEATURE:
<221> NAME/KEY: gene
<222> LOCATION: (1)..(2817)
<223> OTHER INFORMATION: hyperpolarization-activated cyclic
   nucleotide-gated cation channel 1 HCN1 (Accession: AF 421883)

<400> SEQUENCE: 25

```
atggaagata aatcaaattc gttctccagc aacaaagaag gggagaaagc agatgggaat     60
aatgtatttc aaaggcaaga ctcgatacag aagaataata tggggagcca gaacatgaaa    120
ggaggggacc atggaaactc ggtgggcttc aaggggggacc gggaggaagc cttggtcggg    180
ttcgacgata tagacgggtc cggaaaccga catggcttta tgcagcggca atttggagcg    240
atgatgcagc ccggcgtcaa taagttctcc ctgcgaatgt tcggcagtca gaaagccgtt    300
gagaaagagc aagaaagggt ccagacggct ggatactgga tcattcatcc ctatagcgat    360
tttaggttct actgggactt ggtaatgctg gtcatgatga tggggaacct gatcatcatt    420
cctgtaggaa taaccttctt ctcggagcag accaccacca cctggctaat attcaacgtc    480
gcatcagaca ccatcttcct cgtggatctg gtcatgaact tccgcacggg gatcgtcaac    540
gaggagagct ctgagatcat cctggacccc aaggtcataa agatgaacta cctgaagagc    600
tggtttgtgg tcgacttcct ctcgtccata ccagtggatt atatatttct aatagtggaa    660
aaggggtttg actcagaggt gtacaagacg gcgagggcgc tgaggatcgt gaggtttact    720
aagattctgt ctcttctgag gctactgaga cttccccggc tcatcagata catacaccag    780
tgggaggaga ttttccatat gacgtatgac ctggccagtg ctgtggtaag aatatttaat    840 ctgatagga tgatgctact gctgtgccac tgggacggtt gtctgcagtt cctggtccca     900
ctcctacaag atttccctca agattgttgg gtgtcgctaa acggtatggt taatgactcg    960
tggggtaagc agtactcgta cgcactcttc aaggccatga gtcacatgct gtgtatcggg   1020
tacggcgccc gggcccccgt cagcatgtcc gacctgtgga tcaccatgct cagtatgatc   1080
gtgggcgcca cctgctacgc catgttcgtg ggtcacgcca ccgctctcat ccaatcactg   1140
gactcctccc gcaggcagta ccaagagaag tataaacaag tggagcagta catgtcgttc   1200
cacaagctcc ccgcagacat gcggcagaag atccatgatt actatgagca tcgttatcag   1260
ggcaagatct ttgacgagga caatatcctg agtgagctca cgacccgct caaagaggaa   1320 attgtgaact tcaactgtcg gaagctggtg ctaccatgc cgctgttcgc caacgcggac   1380
cccaacttcg tgacgggcat gttgagcaag ctgaagttcg aggtgttcca gcccaacgat   1440
tacatcatca gggagggcac cgtgggcaag aagatgtatt tcattcaaca tggtgtggcc   1500
agtgtcatca ccaagcttaa caaagagatg aagctgacgg atggctctta ctttggagag   1560
atctgtctgc tgacgaaggg gagacgcacg gcgagcgttc gcgctgacac ctactgccgt   1620
ctcttctccc tctctgtgga tcacttcaac gaggtgttgg aagagtaccc tatgatgcgc   1680
```

```
cgcgctttcg agaccgtagc catcgaccgc ctggaccgca tcgggaagaa gaacagcctg   1740
ctcctccaga agttccagaa ggatctgaac gctggggtgt tcaacacgca ggagaacgaa   1800
atactgaagc agataatccg tcaggacagg gagatggtga tgatggtgga ccgcaagcag   1860
tcggtcacag ggatgtcggt cacagggatg tcggtcacag ggatgaacac cacccgata    1920 tctggaaact ccatcattaa ctcgccggct cagccgccct acaccactgc cctgggcaac   1980
aaccagttcc agcagtcagc cacctctttg acctacagcg cttcggccgt caccgctccc   2040
tcctccgcag ccaccgcccg catcctgcct gcctcggcgc agggtgtcta tcccgtcccc   2100
agcgtcatcc acggcaacct gaactcatcc tcgcccgtcc cccagactcc cctctctctc   2160
catcagcaag ggtccatcat gtccccggta tccttcacca cggcggtgtg cagtccaccc   2220
gtgcagaccc ctgggctggc gggccgcagc ttccagtacg gctcgcccac cgcctcccag   2280
ctctccctta tccagcagcc gctgcctact gccctaccac cgcagcaacc actaccacag   2340
ccacagcaac caggaggagc agcggcctcc tcagcaacac aacaaccaca acaacagcag   2400
caagtcccgt cacctcagag gagtgacagc ctccacaagg ccagccatgc tctccagtcg   2460
ggaagcctga gtcgagacgt gcgccacctc tctgcctccc agccctccct gccccacgac   2520
acgtccctgg ggccccgagc gcaccctgca gcgtccgggg actccctggc ctccattgcc   2580
ccgccggtgg ctgcggtcca gggtatgggt atacagagcg gtctccgcac cacagtgccc   2640
cagagggtca acctgttccg ccagatgtca tcaggagcgt tgcctccggt gcgagcggtg   2700
tcctctgcag cccagcacag ggattccact ggttctagga gagattctag aagagattct   2760
accttaagca gtacagagac tgagcaagat aagatgcggt tcgcatcaaa tttatga      2817
```

<210> SEQ ID NO 26
<211> LENGTH: 2160
<212> TYPE: DNA
<213> ORGANISM: Homo Sapiens
<220> FEATURE:
<221> NAME/KEY: gene
<222> LOCATION: (1)..(2160)
<223> OTHER INFORMATION: hyperpolarization-activated, cyclic
    nucleotide-gated potassium channel 2 (HCN2) (partial coding
    sequence)

<400> SEQUENCE: 26

```
atggacgcgc gcgggggcgg cgggcggccc ggggagagcc cgggcgcgac ccccgcgccg     60
gggccgccgc cgccgccgcc gcccgcgccc ccccaacagc agccgccgcc gccgccgccg    120
cccgcgcccc cccggggccc cgggcccgcg ccccccagc acccgcccccg gccgaggcg    180 ttgccccccgg aggcggcgga tgagggcggc ccgcggggcc ggctccgcag ccgcgacagc    240
tcgtgcggcc gccccggcac cccgggcgcg gcgagcacgg ccaagggcag cccgaacggc    300
gagtgcgggc gcggcgagcc gcagtgcagc cccgcggggc ccgagggccc ggcgcggggg    360
cccaaggtgt cgttctcgtg ccgcggggcg gcctcggggc ccgcgccggg gccggggccg    420
gcggaggagg cgggcagcga ggaggcgggc ccggcggggg agccgcgcgg cagccaggcc    480
agcttcatgc agcgccagtt cggcgcgctc ctgcagccgg gcgtcaacaa gttctcgctg    540
cggatgttcg gcagccagaa ggccgtggag cgcgagcagg agcgcgtcaa gtcggcgggg    600
gcctggatca tccacccgta cagcgacttc aggttctact gggacttcac catgctgctg    660
ttcatggtgg aaaacctcat catcatccca gtgggcatca ccttcttcaa ggatgagacc    720
actgccccgt ggatcgtgtt caacgtggtc tcggacacct tcttcctcat ggacctggtg    780
```

| | |
|---|---|
| ttgaacttcc gcaccggcat tgtgatcgag acaacacgg agatcatcct ggaccccgag | 840 |
| aagatcaaga gaagtatct gcgcacgtgg ttcgtggtgg acttcgtgtc ctccatcccc | 900 |
| gtggactaca tcttccttat tgtggagaag ggcattgact ccgaggtcta caagacggca | 960 |
| cgcgccctgc gcatcgtgcg cttcaccaag atcctcagcc tcctgcggct gctgcgcctc | 1020 |
| tcacgcctga tccgctacat ccatcagtgg gaggagatct tccacatgac ctatgacctg | 1080 |
| gccagcgcgg tgatgaggat ctgcaatctc atcagcatga tgctgctgct tgccactgg | 1140 |
| gacggctgcc tgcagttcct ggtgcctatg ctgcaggact cccgcgcaa ctgctgggtg | 1200 |
| tccatcaatg gcatggtgaa ccactcgtgg agtgaactgt actccttcgc actcttcaag | 1260 |
| gccatgagcc acatgctgtg catcgggtac ggccggcagg cgcccgagag catgacggac | 1320 |
| atctggctga ccatgctcag catgattgtg ggtgccacct gctacgccat gttcatcggc | 1380 |
| cacgccactg ccctcatcca gtcgctggac tcctcgcggc gccagtacca ggagaagtac | 1440 |
| aagcaggtgg agcagtacat gtccttccac aagctgccag ctgacttccg ccagaagatc | 1500 |
| cacgactact atgagcaccg ttaccagggc aagatgtttg acgaggacag catcctgggc | 1560 |
| gagctcaacg ggcccctgcg ggaggagatc gtcaacttca actgccggaa gctggtggcc | 1620 |
| tccatgccgc tgttcgccaa cgccgacccc aacttcgtca cggccatgct gaccaagctc | 1680 |
| aagttcgagg tcttccagcc gggtgactac atcatccgcg aaggcaccat cgggaagaag | 1740 |
| atgtacttca tccagcacgg cgtggtcagc gtgctcacta agggcaacaa ggagatgaag | 1800 |
| ctgtccgatg gctcctactt cggggagatc tgcctgctca ccggggccg ccgcacggcg | 1860 |
| agcgtgcggg ccgacaccta ctgccgcctc tattcgctga gcgtggacaa cttcaacgag | 1920 |
| gtgctggagg agtaccccat gatgcggcgc gccttcgaga cggtggccat cgaccgcctg | 1980 |
| gaccgcatcg gcaagaagaa ttccatcctc ctgcacaagg tgcagcatga cctcaactcg | 2040 |
| ggcgtattca caaccagga gaacgccatc atccaggaga tcgtcaagta cgaccgcgag | 2100 |
| atggtgcagc aggccgagct gggtcagcgc gtgggcctct cccgccgcc gccgccgccg | 2160 |

<210> SEQ ID NO 27
<211> LENGTH: 1812
<212> TYPE: DNA
<213> ORGANISM: Homo Sapiens
<220> FEATURE:
<221> NAME/KEY: gene
<222> LOCATION: (1)..(1812)
<223> OTHER INFORMATION: hyperpolarization-activated, cyclic
     nucleotide-gated potassium channel 3 (HCN3) (partial coding
     sequence)

<400> SEQUENCE: 27

| | |
|---|---|
| atggaggcag agcagcggcc ggcggcgggg gccagcgaag gggcgacccc tggactggag | 60 |
| gcggtgcctc ccgttgctcc cccgcctgcg accgcggcct caggtccgat ccccaaatct | 120 |
| gggcctgagc ctaagaggag gcaccttggg acgctgctcc agcctacggt caacaagttc | 180 |
| tcccttcggg tgttcggcag ccacaaagca gtggaaatcg agcaggagcg ggtgaagtca | 240 |
| gcgggggcct ggatcatcca ccctacagc gacttccggt tttactggga cctgatcatg | 300 |
| ctgctgctga tggtggggaa cctcatcgtc ctgcctgtgg catcaccttt cttcaaggag | 360 |
| gagaactccc cgccttggat cgtcttcaac gtattgtctg atactttctt cctactggat | 420 |
| ctggtgctca acttccgaac gggcatcgtg tggaggagg tgctgagat cctgctggca | 480 |
| ccgcgggcca tccgcacgcg ctacctgcgc acctggttcc tggttgacct catctcttct | 540 |
| atccctgtgg attacatctt cctagtggtg gagctggagc cacggttgga cgctgaggtc | 600 |

```
tacaaaacgg cacgggccct acgcatcgtt cgcttcacca agatcctaag cctgctgagg      660
ctgctccgcc tctcccgcct catccgctac atacaccagt gggaggagat ctttcacatg      720
acctatgacc tggccagtgc tgtggttcgc atcttcaacc tcattgggat gatgctgctg      780
ctatgtcact gggatggctg tctgcagttc ctggtgccca tgctgcagga cttccctccc      840
gactgctggg tctccatcaa ccacatggtg aaccactcgt ggggccgcca gtattcccat      900
gccctgttca aggccatgag ccacatgctg tgcattggct atgggcagca ggcacctgta      960
ggcatgcccg acgtctggct caccatgctc agcatgatcg taggtgccac atgctacgcc     1020
atgttcatcg gccatgccac ggcactcatc cagtccctgg actcttcccg cgtcagtac      1080
caggagaagt acaagcaggt ggagcagtac atgtccttcc acaagctgcc agcagacacg     1140
cggcagcgca tccacgagta ctatgagcac cgctaccagg gcaagatgtt cgatgaggaa     1200
agcatcctgg gcgagctgag cgagccgctt cgcgaggaga tcattaactt cacctgtcgg     1260
ggcctggtgg cccacatgcc gctgtttgcc catgccgacc ccagcttcgt cactgcagtt     1320
ctcaccaagc tgcgctttga ggtcttccag ccgggggatc tcgtggtgcg tgagggctcc     1380
gtggggagga agatgtactt catccagcat gggctgctca gtgtgctggc ccgcggcgcc     1440
cgggacacac gcctcaccga tggatcctac tttggggaga tctgcctgct aactaggggc     1500
cggcgcacag ccagtgttcg ggctgacacc tactgccgcc tttactcact cagcgtggac     1560
catttcaatg ctgtgcttga ggagttcccc atgatgcgcg gggcctttga gactgtggcc     1620
atggatcggc tgctccgcat cggcaagaag aattccatac tgcagcggaa cgcgctccga     1680
ccaagtccag gcagcagtgg tggcatcatg gagcagcact tggtgcaaca tgacagagac     1740
atggctcggg gtgttcgggg tcgggccccg agcacaggag ctcagcttag tggaaagcca     1800
gtactgtggg ag                                                          1812
```

<210> SEQ ID NO 28
<211> LENGTH: 2214
<212> TYPE: DNA
<213> ORGANISM: Homo Sapiens
<220> FEATURE:
<221> NAME/KEY: gene
<222> LOCATION: (1)..(2214)
<223> OTHER INFORMATION: Hyperpolarization Activated Cyclic
      Nucleotide-Gated Potassium Channel 4 (HCN4) (Partial Coding
      Sequence)

<400> SEQUENCE: 28

```
atggacaagc tgccgccgtc catgcgcaag cggctctaca gcctcccgca gcaggtgggg       60
gccaaggcgt ggatcatgga cgaggaagag gacgccgagg aggaggggc cggggccgc       120
caagacccca gccgcaggag catccggctg cggccactgc cctcgccctc ccctcggcg      180
gccgcgggtg gcacggagtc ccggagctcg gccctcgggg cagcggacag cgaagggccg     240
gcccgcggcg cgggcaagtc cagcacgaac ggcgactgca ggcgcttccg cgggagcctg     300
gcctcgctgg gcagccgggg cggcggcagc ggcggcacgg ggagcggcag cagtcacgga     360
cacctgcatg actccgcgga ggagcggcgg ctcatcgccg agggcgacgc gtccccggc      420
gaggacagga cgccccagg cctggcggcc gagcccgagc gccccggcgc ctcggcgcag     480
cccgcagcct cgccgccgcc gcccagcag ccaccgcagc cggcctccgc ctcctgcgag      540
cagccctcgg tggacaccgc tatcaaagtg gaggaggcg cggctgccgg cgaccagatc      600
ctcccggagg ccgaggtgcg cctgggccag gccggcttca tgcagcgcca gttcggggcc     660
```

-continued

| | |
|---|---|
| atgctccaac ccggggtcaa caaattctcc ctaaggatgt tcggcagcca gaaagccgtg | 720 |
| gagcgcgaac aggagagggt caagtcggcc ggattttgga ttatccaccc ctacagtgac | 780 |
| ttcagatttt actgggacct gaccatgctg ctgctgatgg tgggaaacct gattatcatt | 840 |
| cctgtgggca tcaccttctt caaggatgag aacaccacac cctggattgt cttcaatgtg | 900 |
| gtgtcagaca cattcttcct catcgacttg gtcctcaact tccgcacagg gatcgtggtg | 960 |
| gaggacaaca cagagatcat cctggacccg cagcggatta aaatgaagta cctgaaaagc | 1020 |
| tggttcatgg tagatttcat ttcctccatc cccgtggact acatcttcct cattgtggag | 1080 |
| acacgcatcg actcggaggt ctacaagact gcccgggccc tgcgcattgt ccgcttcacg | 1140 |
| aagatcctca gcctcttacg cctgttacgc ctctcccgcc tcattcgata tattcaccag | 1200 |
| tgggaagaga tcttccacat gacctacgac ctggccagcg ccgtggtgcg catcgtgaac | 1260 |
| ctcatcggca tgatgctcct gctctgccac tgggacggc gcctgcagtt cctggtaccc | 1320 |
| atgctacagg acttccctga cgactgctgg gtgtccatca caacatggt gaacaactcc | 1380 |
| tgggggaagc agtactccta cgcgctcttc aaggccatga ccacatgct gtgcatcggc | 1440 |
| tacgggcggc aggcgcccgt gggcatgtcc gacgtctggc tcaccatgct cagcatgatc | 1500 |
| gtgggtgcca cctgctacgc catgttcatt ggccacgcca ctgccctcat ccagtccctg | 1560 |
| gactcctccc ggcgccagta ccaggaaaag tacaagcagg tggagcagta catgtccttt | 1620 |
| cacaagctcc cgcccgacac ccggcagcgc atccacgact actacgagca ccgctaccag | 1680 |
| ggcaagatgt cgacgaggga gagcatcctg ggcgagctaa gcgagcccct gcgggaggag | 1740 |
| atcatcaact ttaactgtcg gaagctggtg gcctccatgc cactgtttgc caatgcggac | 1800 |
| cccaacttcg tgacgtccat gctgaccaag ctgcgtttcg aggtcttcca gcctggggac | 1860 |
| tacatcatcc gggaaggcac cattggcaag aagatgtact tcatccagca tggcgtggtc | 1920 |
| agcgtgctca ccaagggcaa caaggagacc aagctggccg acggctccta ctttggagag | 1980 |
| atctgcctgc tgacccgggg ccggcgcaca gccagcgtga gggccgacac ctactgccgc | 2040 |
| ctctactcgc tgagcgtgga caacttcaat gaggtgctgg aggagtaccc catgatgcga | 2100 |
| agggccttcg agaccgtggc gctggaccgc tggaccgca ttggcaagaa gaactccatc | 2160 |
| ctcctccaca aagtccagca cgacctcaac tccggcgtct caactacca ggag | 2214 |

<210> SEQ ID NO 29
<211> LENGTH: 2256
<212> TYPE: DNA
<213> ORGANISM: Homo Sapiens
<220> FEATURE:
<221> NAME/KEY: gene
<222> LOCATION: (1)..(2256)
<223> OTHER INFORMATION: Homo Sapiens Hyperpolarization Activated Cyclic
      Nucleotide-Gated Potassium Channel 4 (HCN4) partial coding
      sequence with c-myc partial coding sequence

<400> SEQUENCE: 29

| | |
|---|---|
| cgcctcgcca tggacaagct gccgccgtcc atgcgcaagc ggctctacag cctcccgcag | 60 |
| caggtggggg ccaaggcgtg gatcatggac gaggaagagg acgccgagga ggaggggcc | 120 |
| gggggccgcc aagaccccag ccgcaggagc atccggctgc ggccactgcc ctcgccctcc | 180 |
| ccctcggcgg ccgcgggtgg cacggagtcc cggagctcgg ccctcggggc agcggacagc | 240 |
| gaagggccgg cccgcggcgc gggcaagtcc agcacgaacg gcgactgcag gcgcttccgc | 300 |
| gggagcctgg cctcgctggg cagccggggc ggcagcgcg cggcacggg gagcggcagc | 360 |
| agtcacggac acctgcatga ctccgcggag gagcggcggc tcatcgccga ggcgacgcg | 420 |

```
tccccccggcg aggacaggac gcccccaggc ctggcggccg agcccgagcg ccccggcgcc    480
tcggcgcagc ccgcagcctc gccgccgccg ccccagcagc caccgcagcc ggcctccgcc    540
tcctgcgagc agccctcggt ggacaccgct atcaaagtgg agggaggcgc ggctgccggc    600
gaccagatcc tcccggaggc cgaggtgcgc ctgggccagg ccggcttcat gcagcgccag    660
ttcggggcca tgctccaacc cggggtcaac aaattctccc taaggatgtt cggcagccag    720
aaagccgtgg agcgcgaaca ggagagggtc aagtcggccg gattttggat tatccacccc    780
tacagtgact tcagattta ctgggacctg accatgctgc tgctgatggt gggaaacctg    840
attatcattc ctgtgggcat caccttcttc aaggatgaga acaccacacc ctggattgtc    900
ttcaatgtgg tgtcagacac attcttcctc atcgacttgg tcctcaactt ccgcacaggg    960
atcgtggtgg aggacaacac agagatcatc ctggacccgc agcggattaa aatgaagtac   1020
ctgaaaagct ggttcatggt agatttcatt tcctccatcc ccgtggacta catcttcctc   1080
attgtggaga cacgcatcga ctcggaggtc tacaagactg cccgggccct gcgcattgtc   1140
cgcttcacga agatcctcag cctcttacgc ctgttacgcc tctcccgcct cattcgatat   1200 attaccagt gggaagagat cttccacatg acctacgacc tggccagcgc cgtggtgcgc   1260
atcgtgaacc tcatcggcat gatgctcctg ctctgccact gggacggctg cctgcagttc   1320
ctggtaccca tgctacagga cttccctgac gactgctggg tgtccatcaa caacatggtg   1380
aacaactcct gggggaagca gtactcctac gcgctcttca aggccatgag ccacatgctg   1440
tgcatcggct acgggcggca ggcgcccgtg ggcatgtccg acgtctggct caccatgctc   1500
agcatgatcg tgggtgccac ctgctacgcc atgttcattg ccacgccac tgccctcatc   1560 cagtccctgg actcctcccg gcgccagtac caggaaaagt acaagcaggt ggagcagtac   1620
atgtcctttc acaagctccc gcccgacacc cggcagcgca tccacgacta ctacgagcac   1680
cgctaccagg gcaagatgtt cgacgaggag agcatcctgg gcgagctaag cgagcccctg   1740
cgggaggaga tcatcaactt taactgtcgg aagctggtgg cctccatgcc actgtttgcc   1800
aatgcggacc ccaacttcgt gacgtccatg ctgaccaagc tgcgtttcga ggtcttccag   1860
cctggggact acatcatccg ggaaggcacc attggcaaga gatgtactt catccagcat   1920 ggcgtggtca gcgtgctcac caagggcaac aaggagacca agctggccga cggctcctac   1980
tttggagaga tctgcctgct gacccggggc cggcgcacag ccagcgtgag ggccgacacc   2040
tactgccgcc tctactcgct gagcgtggac aacttcaatg aggtgctgga ggagtacccc   2100
atgatgcgaa gggccttcga gaccgtggcg ctggaccgcc tggaccgcat tggcaagaag   2160
aactccatcc tcctccacaa agtccagcac gacctcaact ccggcgtctt caactaccag   2220
gagcagaagc tgatctcaga ggaggacctg ctttga                              2256
```